United States Patent
Korman et al.

(10) Patent No.: US 9,296,822 B2
(45) Date of Patent: Mar. 29, 2016

(54) HUMAN MONOCLONAL ANTIBODIES TO O8E

(71) Applicant: E.R. Squibb & Sons, L.L.C., Princeton, NJ (US)

(72) Inventors: Alan J. Korman, Piedmont, CA (US); Mark J. Selby, San Francisco, CA (US); Li-Sheng Lu, Mountain View, CA (US); Alison J. Witte, Scotts Valley, CA (US); Haichun Huang, Fremont, CA (US)

(73) Assignee: E.R. SQUIBB & SONS, L.L.C., Princeton, NJ (US)

( * ) Notice: Subject to any disclaimer, the term of this patent is extended or adjusted under 35 U.S.C. 154(b) by 161 days.

(21) Appl. No.: 14/074,168

(22) Filed: Nov. 7, 2013

(65) Prior Publication Data

US 2014/0134180 A1    May 15, 2014

Related U.S. Application Data

(62) Division of application No. 12/092,866, filed as application No. PCT/US2006/061816 on Dec. 8, 2006, now Pat. No. 8,609,816.

(60) Provisional application No. 60/824,593, filed on Sep. 5, 2006, provisional application No. 60/748,914, filed on Dec. 8, 2005.

(51) Int. Cl.
| | |
|---|---|
| *A61K 39/395* | (2006.01) |
| *A61K 39/00* | (2006.01) |
| *C07K 16/30* | (2006.01) |
| *C07K 16/28* | (2006.01) |

(52) U.S. Cl.
CPC ............ *C07K 16/30* (2013.01); *C07K 16/2827* (2013.01); *A61K 2039/505* (2013.01); *C07K 2317/21* (2013.01); *C07K 2317/41* (2013.01); *C07K 2317/565* (2013.01); *C07K 2317/732* (2013.01); *C07K 2317/77* (2013.01); *C07K 2317/92* (2013.01); *C07K 2319/55* (2013.01)

(58) Field of Classification Search
None
See application file for complete search history.

(56) References Cited

U.S. PATENT DOCUMENTS

| | | | |
|---|---|---|---|
| 6,255,458 B1 | 7/2001 | Lonberg et al. |
| 6,429,303 B1 | 8/2002 | Green et al. |
| 6,468,546 B1 | 10/2002 | Mitcham et al. |
| 6,488,931 B1 | 12/2002 | Mitcham et al. |
| 6,528,253 B1 | 3/2003 | Mitcham et al. |
| 6,670,463 B1 | 12/2003 | Mitcham et al. |
| 6,699,664 B1 | 3/2004 | Mitcham et al. |
| 6,783,969 B1 | 8/2004 | Tang et al. |
| 6,808,710 B1 | 10/2004 | Wood et al. |
| 6,858,710 B2 | 2/2005 | Bangur et al. |
| 6,891,030 B2 | 5/2005 | Chen |
| 6,936,704 B1 | 8/2005 | Freeman et al. |
| 6,962,980 B2 | 11/2005 | Mitcham et al. |
| 6,965,018 B2 | 11/2005 | Mikesell et al. |
| 7,030,219 B2 | 4/2006 | Pardoll et al. |
| 7,038,013 B2 | 5/2006 | Freeman et al. |
| 7,052,694 B2 | 5/2006 | Pease et al. |
| 7,101,550 B2 | 9/2006 | Wood et al. |
| 7,189,507 B2 | 3/2007 | Mack et al. |
| 7,189,563 B2 | 3/2007 | Eaton et al. |
| 7,202,334 B1 | 4/2007 | Mitcham et al. |
| 7,279,567 B2 | 10/2007 | Mikesell et al. |
| 7,304,149 B2 | 12/2007 | Murphy et al. |
| 7,306,796 B2 | 12/2007 | Afar et al. |
| 7,358,354 B2 | 4/2008 | Mikesell et al. |
| 7,368,527 B2 | 5/2008 | Rosen et al. |
| 7,368,554 B2 | 5/2008 | Mikesell et al. |
| 7,390,888 B2 | 6/2008 | Pease et al. |
| 7,435,589 B2 | 10/2008 | Mack et al. |
| 7,482,325 B2 | 1/2009 | Yoshinaga et al. |
| 7,498,298 B2 | 3/2009 | Doronina et al. |
| 7,501,119 B2 | 3/2009 | Radhakrishnan et al. |
| 2002/0034749 A1 | 3/2002 | Billing-Medel et al. |
| 2003/0039653 A1 | 2/2003 | Chen et al. |
| 2003/0069394 A1 | 4/2003 | Eaton et al. |
| 2003/0124128 A1 | 7/2003 | Lillie et al. |
| 2003/0157109 A1 | 8/2003 | Corvalan et al. |
| 2003/0181668 A1 | 9/2003 | Eaton et al. |
| 2003/0208058 A1 | 11/2003 | Fiscella et al. |
| 2004/0005592 A1 | 1/2004 | Emtage et al. |
| 2004/0053250 A1 | 3/2004 | Tang et al. |

(Continued)

FOREIGN PATENT DOCUMENTS

| | | |
|---|---|---|
| EP | 1 109 937 | 11/2008 |
| JP | 2003-052374 | 2/2003 |

(Continued)

OTHER PUBLICATIONS

Cancer information from National Institute of Cancer, Apr. 29, 2010, pp. 1-2.*
Vogelstein et al., Nature Medicine, 2004, 10(8): 789-799.*
Zafir-Lavie et al., Oncogene 2007, 26:3714-3733.*
U.S. Appl. No. 12/092,866, Nov. 8, 2013 Issue Fee payment.
U.S. Appl. No. 12/092,866, Nov. 6, 2013 Amendment after Notice of Allowance.
U.S. Appl. No. 12/092,866, Aug. 9, 2013 Notice of Allowance.
U.S. Appl. No. 12/092,866, Aug. 4, 2011 Amendment and Request for Continued Examination (RCE).

(Continued)

*Primary Examiner* — Hong Sang
(74) *Attorney, Agent, or Firm* — Baker Botts L.L.P.

(57) ABSTRACT

The present disclosure provides isolated monoclonal antibodies, particularly human monoclonal antibodies that specifically bind to O8E with high affinity. Nucleic acid molecules encoding the antibodies of this disclosure, expression vectors, host cells and methods for expressing the antibodies of this disclosure are also provided. Immunoconjugates, bispecific molecules and pharmaceutical compositions comprising the antibodies of this disclosure are also provided. This disclosure also provides methods for treating cancer.

26 Claims, 25 Drawing Sheets

(56) References Cited

U.S. PATENT DOCUMENTS

| | | | |
|---|---|---|---|
| 2004/0076955 | A1 | 4/2004 | Mack et al. |
| 2004/0175380 | A1 | 9/2004 | Allison et al. |
| 2004/0259152 | A1 | 12/2004 | Murray et al. |
| 2005/0014700 | A1 | 1/2005 | Boger |
| 2005/0031634 | A1 | 2/2005 | Bangur et al. |
| 2005/0202536 | A1 | 9/2005 | Chen et al. |
| 2005/0214831 | A1 | 9/2005 | Monahan et al. |
| 2006/0008901 | A1 | 1/2006 | Eaton et al. |
| 2006/0073544 | A1 | 4/2006 | Baker et al. |
| 2006/0140944 | A1 | 6/2006 | Yoshinaga |
| 2006/0153841 | A1 | 7/2006 | Freeman et al. |
| 2006/0154313 | A1 | 7/2006 | Anderson et al. |
| 2006/0228705 | A1 | 10/2006 | Ebner et al. |
| 2006/0292593 | A1 | 12/2006 | Pardoll et al. |
| 2007/0059748 | A1 | 3/2007 | Afar et al. |
| 2007/0122378 | A1 | 5/2007 | Freeman et al. |
| 2007/0154886 | A1 | 7/2007 | Macina et al. |
| 2007/0161016 | A1 | 7/2007 | Afar et al. |
| 2007/0178101 | A1 | 8/2007 | Pilkington et al. |
| 2007/0202100 | A1 | 8/2007 | Wood et al. |
| 2007/0218032 | A1 | 9/2007 | Kwon et al. |
| 2008/0008706 | A1 | 1/2008 | Dong et al. |
| 2008/0025981 | A1 | 1/2008 | Young et al. |
| 2008/0193467 | A1 | 8/2008 | Pease et al. |
| 2008/0226662 | A1 | 9/2008 | Pardoll et al. |
| 2008/0241175 | A1 | 10/2008 | Pardoll et al. |
| 2008/0311573 | A1 | 12/2008 | Lillie et al. |
| 2009/0074660 | A1 | 3/2009 | Korman et al. |
| 2010/0145036 | A1 | 6/2010 | Sufi et al. |
| 2011/0085970 | A1 | 4/2011 | Terrett et al. |

FOREIGN PATENT DOCUMENTS

| | | |
|---|---|---|
| JP | 2003-245082 | 9/2003 |
| WO | WO 99/25877 | 5/1999 |
| WO | WO 99/63088 | 12/1999 |
| WO | WO 00/12758 | 3/2000 |
| WO | WO 00/46240 | 8/2000 |
| WO | WO 00/73454 | 12/2000 |
| WO | WO 00/76531 | 12/2000 |
| WO | WO 01/18204 | 3/2001 |
| WO | WO 01/40269 | 6/2001 |
| WO | WO 01/68848 | 9/2001 |
| WO | WO 01/83750 | 11/2001 |
| WO | WO 01/94641 | 12/2001 |
| WO | WO 02/02587 | 1/2002 |
| WO | WO 02/02624 | 1/2002 |
| WO | WO 02/06317 | 1/2002 |
| WO | WO 02/10187 | 2/2002 |
| WO | WO 02/43478 | 6/2002 |
| WO | WO 02/062203 | 8/2002 |
| WO | WO 02/070539 | 9/2002 |
| WO | WO 02/071928 | 9/2002 |
| WO | WO 02/097046 | 12/2002 |
| WO | WO 02/102235 | 12/2002 |
| WO | WO 03/004989 | 1/2003 |
| WO | WO 03/104399 | 12/2003 |
| WO | WO 04/000221 | 12/2003 |
| WO | WO 2004/053079 | 6/2004 |
| WO | WO 2004/071530 | 8/2004 |
| WO | WO 2004/078918 | 9/2004 |
| WO | WO 2004/101756 | 11/2004 |
| WO | WO 2004/113500 | 12/2004 |
| WO | WO 2005/027846 | 3/2005 |
| WO | WO 2005/051990 | 6/2005 |
| WO | WO 2005/059106 | 6/2005 |
| WO | WO 2005/112919 | 12/2005 |
| WO | WO 2006/053110 | 5/2006 |
| WO | WO 2006/066229 | 6/2006 |
| WO | WO 2006/074418 | 7/2006 |
| WO | WO 2006/098887 | 9/2006 |
| WO | WO 2006/104677 | 10/2006 |
| WO | WO 2006/121991 | 11/2006 |
| WO | WO 2006/124667 | 11/2006 |
| WO | WO 2006/133396 | 12/2006 |
| WO | WO 2006/138670 | 12/2006 |
| WO | WO 2007/038658 | 4/2007 |
| WO | WO 2007/041694 | 4/2007 |
| WO | WO 2007/067681 | 6/2007 |
| WO | WO 2007/067682 | 6/2007 |
| WO | WO 2007/067683 | 6/2007 |
| WO | WO 2007/067991 | 6/2007 |
| WO | WO 2007/082154 | 7/2007 |
| WO | WO 2007/109254 | 9/2007 |
| WO | WO 2007/147265 | 12/2007 |

OTHER PUBLICATIONS

U.S. Appl. No. 12/092,866, Jul. 20, 2011 Advisory Action.
U.S. Appl. No. 12/092,866, Jul. 5, 2011 Response to Final Office Action.
U.S. Appl. No. 12/092,866, May 5, 2011 Final Office Action.
U.S. Appl. No. 12/092,866, Feb. 23, 2011 Response to Non-Final Office Action.
U.S. Appl. No. 12/092,866, Oct. 29, 2010 Non-Final Office Action and Examiner's Interview Summary.
U.S. Appl. No. 12/092,866, Aug. 30, 2010 Response to Restriction Requirement.
U.S. Appl. No. 12/092,866, Jul. 28, 2010 Restriction Requirement.
U.S. Appl. No. 12/745,677, Aug. 15, 2012 Notice of Abandonment.
U.S. Appl. No. 12/745,677, Jan. 30, 2012 Non-Final Office Action.
U.S. Appl. No. 12/745,677, Jul. 7, 2011 Response to Restriction Requirement.
U.S. Appl. No. 12/745,677, Jun. 8, 2011 Restriction Requirement.
International Search Report for PCT/US2008/084923 mailed Oct. 14, 2009.
Bendig, umanization of Rodent Monoclonal Antibodies by CDR Grafting, *Method: A Comparison to Methods in Enzymology*, 8:83-93 (1995).
Bignotti, et al., "Differential Gene Expression Profiles between Tumor Biopsies and Short-term Primary Cultures of Ovarian Serous Carcinomas: Identification of Novel Molecular Biomarkers for Early Diagnosis and Therapy," *Gynecol Oneol*, 103:405-416 (2006).
Casset, et al., "A Peptide Mimetic of an Anti-CD4 monoclonal Antibody by Rational Design", *Biochemical and Biophysical Research Communications*, 307:198-205 (2003).
Carreno, et al., "The B7 Family of Ligands and Its Receptors: New Pathways for Costimulation and Inhibition of Immune Responses," *Ann Rev Immunol*, 20:29-53 (2002).
Carreno, et al., "BTLA: a New Inhibitory Receptor with a B7-like Ligand," *Trends Immunol*, 24:524-527 (2003).
Chen, et al., "Expression of the Novel Co-stimulating Molecule B7-H4 by Renal Tubular Epithelial cells," *Kidney Int*, 70(12):2092-2099 (2006).
Choi, et al., 2003, "Genomic Organization and Expression Analysis of B7-H4, an Immune Inhibitory Molecule of the B7 Family," *J. Immunol*, 171(9):4650-4654 (2003).
Colman, "Effects of Amino Acid Sequence Changes on Antibody-Antigen Interactions", *Research in Immunology*, 145:33-36 (1994).
Fishwild, et al., "High-avidity Human IgGκ Monoclonal Antibodies from a Novel Strain of Minilocus Transgenic Mice," *Nat Biotechnol*, 14(7):845-851 (1996).
Fundamental Immunology, William E. Paul, M.D., ed., 3rd Ed., 1993: 292-295.
Heintz, et al., "Carcinoma of the Ovary," *J Epidemiol Biostat*, 6:107-138 (2001).
Khoury, et al., "The Roles of the New Negative T Cell Costimulatory Pathways in Regulating Autoimmunity," *Immunity*, 20:529-538 (2004).
Kim, et al., "Antibody Engineering for the Development of Therapeutic Antibodies", *Molecules and Cells*, 20(1):17-29 (2005).
Krambeck, et al., "B7-H4 Expression in Renal Cell Carcinoma and Tumor Vasculature: Associations with Cancer Progression and Survival," *PNAS*, 103:10391-10396 (2006).
Kryczek, et al., "B7-H4 Expression Identifies a Novel Suppressive Macrophage Population in Human Ovarian Carcinoma," *J Exp Med*, 203(4):871-881 (2006).

(56) References Cited

OTHER PUBLICATIONS

Lonberg, "Human Antibodies from Transgenic Animals," *Nat Biothechnol,* 23(9):1117-1125 (2005).

MacCallum, et al., "Antibody-Antigen Interactions: Contact Analysis and Binding Site Topography", *J. Mol. Biol.,* 262: 732-745 (1996).

Prasad, et al., "B7S1, a Novel B7 Family Member that Negatively Regulates T Cell Activation," *Immunity,* 18(6):863-873 (2003).

Rudikoff, et al., "Single Amino Acid Substitution Altering Antigen-Binding Specificity", *PNAS,* 79(6):1979-1983 (1982).

Salceda, et al., "The Immunomodulatory Protein B7-H4 is Overespressed in Breast and Ovarian Cancers and Promotes Epithelial Cell Transformation," *Exp Cell Res,* 306(1):128-141 (2005).

Seidman, et al., Surface of Epithelial Tumors of Ovary, "Blaustein's Pathology of the Female Genital Tract," Chapter 18:791-904 (Kurman RJ, editor, 5th Edition) (2002).

Shields, et al., Lack of Fucose on Human IgG1 N-linked Oligosaccharide Improves Binding to Human FcγRIII and Antibody-dependent Cellular Toxicity, *J Biol Chem,* 227(30):26733-26740 (2002).

Sica, et al., "B7-H4, a Molecule of the B7 Family, Negatively Regulates T-Cell Immunity," *Immunity,* 18(6):849-861 (2003).

Simon, et al., "B7-H4 Is a Novel Membrane-Bound Protein and a Candidate Serum and Tissue Biomarker for Ovarian Cancer," *Cancer Res,* 66:1570-1575 (2006).

Smith, "New Drugs for Breast Cancer," *Lancet,* 360:790-792 (2002).

Sun, et al., "B7-H3 and B7-H4 Expression in Non-small-cell Lung Cancer," *Lung Cancer,* 53:143-151 (2006).

Tringler, et al., "B7-H4 is Highly Expressed in Ductal and Lobular Breast Cancer," *Clin Cancer Res.,* 11(5):1842-1848 (2005).

Tringler, et al., "B7-H4 Overexpression in Ovarian Tumors," *Gynecol Oncol,* 100(1):44-52 (2006).

Sequence Alignment, 2 pages (2012).

Wang, et al., "Co-signaling Molecules of the B7-CD28 Family in Positive and Negative Regulation of T Lymphocyte Responses," *Microbes Infect,* 6(8):759-766 (2004).

Wen-Tao, et al., "Growth inhibitory effect of adriamycin conjugated to single-chain antibody on human lung adenocarcinoma in vitro", *Database Biosis (Online) Biosciences Information Service,* 26(12):718-721 (2004) (English Abstract is included).

Zang, et al., "B7x: A Widely Expressed B7 Family Member that Inhibits T Cell Activation," *PNAS,* 100:10388-10392 (2003).

Zheng, et al., "Cell-ELISA using beta-galactosidase conjugated antibodies", *Journal of Immunological Methods,* 234(1-2):153-167 (2000).

\* cited by examiner

Anti-O8E 1G11VH
V-segment: 4-34
D-segment: D6-13
J-segment: JH4b

```
         Q   V   Q   L   Q   Q   W   G   A   G   L   L   K   P   S   E   T   L
  1      CAG GTG CAG CTA CAG CAG TGG GGC GCA GGA CTG TTG AAG CCT TCG GAG ACC CTG

CDR1
                                                             ------------------------
         S   L   T   C   A   V   Y   G   G   S   F   S   D   Y   F   W   T   W
 55      TCC CTC ACC TGC GCT GTC TAT GGT GGG TCC TTC AGT GAT TAC TTC TGG ACC TGG

CDR2
                                                                  -------------------
         I   R   Q   P   P   G   K   G   L   E   W   I   G   E   I   N   H   S
109      ATC CGC CAG CCC CCA GGG AAG GGC CTG GAG TGG ATT GGG GAA ATC AAT CAT AGT

CDR2
         ----------------------------------------
         G   T   T   N   Y   N   P   S   L   K   S   R   V   T   I   S   A   D
163      GGA ACC ACC AAC TAC AAC CCG TCC CTC AAG AGT CGA GTC ACC ATT TCA GCA GAC

T   S   K   N   Q   F   S   L   R   L   S   S   V   T   A   A   D   T
217      ACG TCC AAG AAC CAG TTC TCC CTG AGG CTG AGC TCT GTG ACC GCC GCG GAC ACG

CDR3
                                 -------------------------------------------------
         A   V   Y   Y   C   A   R   L   S   S   W   S   N   W   A   F   E   Y
271      GCT GTG TAT TAC TGT GCG AGA CTC AGC AGC TGG TCG AAC TGG GCC TTT GAG TAC
                                     |      D6-13/DN1         |          └─► JH4b

W   G   Q   G   T   L   V   T   V   S   S
325      TGG GGC CAG GGA ACC CTG GTC ACC GTC TCC TCA
```

Figure 1A

Anti-O8E 1G11VK

V-segement:    A27
    J-segment:     JK4

```
              E   I   V   L   T   Q   F   P   G   T   L   S   L   S   P   G   E   R
  1          GAA ATT GTG TTG ACG CAG TTT CCA GGC ACC CTG TCT TTG TCT CCA GGG GAA AGA
                                                                  CDR1
                                                        ~~~~~~~~~~~~~~~~~~~~~~~~~~~~~~~~~~~~~~
              A   T   L   S   C   R   A   S   Q   S   V   S   S   T   Y   L   A   W
 55          GCC ACC CTC TCC TGC AGG GCC AGT CAG AGT GTT AGC AGC ACC TAC TTA GCC TGG
                                                                                  CDR2
                                                                              ~~~~~~~~~~~~~~~~
              Y   Q   Q   K   P   G   Q   A   P   R   V   L   I   Y   G   A   S   R
109          TAC CAG CAG AAA CCT GGC CAG GCT CCC AGG GTC CTC ATC TAT GGT GCA TCC AGA
                 CDR2
             ~~~~~~~~~~~~~~~
              R   A   T   G   I   P   D   R   F   S   G   S   G   S   G   T   D   F
163          AGG GCC ACT GGC ATC CCA GAC AGG TTC AGT GGC AGT GGG TCT GGG ACA GAC TTC
                                                                                  CDR3
                                                                                  ~~~
              T   L   T   I   S   R   L   E   P   E   D   F   A   V   Y   Y   C   Q
217          ACT CTC ACC ATC AGC AGA CTG GAG CCT GAA GAT TTT GCA GTG TAT TAC TGT CAG
                  CDR3
             ~~~~~~~~~~~~~~~~~~~~~~~~~~~~
              Q   Y   G   S   S   P   L   T   F   G   G   G   T   K   V   E   I   K
271          CAG TAT GGT AGC TCA CCG CTC ACT TTC GGC GGA GGG ACC AAG GTG GAG ATC AAA
                               └─► JK4
```

Figure 1B

Anti-O8E 2A7VH
    V-segment:     3-53
    D-segment:     Not found
    J-segment:     JH6b

```
         E   V   Q   L   V   E   S   G   G   G   L   I   Q   P   G   G   S   L
  1     GAG GTG CAG CTG GTG GAG TCT GGA GGA GGC TTG ATC CAG CCT GGG GGG TCC CTG

CDR1
                                                              ~~~~~~~~~~~~~~~~~~
         R   L   S   C   A   A   S   G   F   T   V   S   S   N   Y   M   N   W
  55    AGA CTC TCC TGT GCA GCC TCT GGG TTC ACC GTC AGT AGC AAC TAC ATG AAC TGG

CDR2
                                                         ~~~~~~~~~~~~~~~~~~
         V   R   Q   A   P   G   K   G   L   E   W   V   S   V   I   Y   G   S
  109   GTC CGC CAG GCT CCA GGG AAG GGG CTG GAG TGG GTC TCA GTT ATT TAT GGC AGT

CDR2
         ~~~~~~~~~~~~~~~~~~~~~~~~~~~~~~~~~~~~~~~~~~~~~~~
         G   R   T   Y   Y   A   D   S   V   K   G   R   V   T   I   S   R   D
  163   GGT AGA ACA TAT TAC GCA GAC TCC GTG AAG GGC CGA GTC ACC ATC TCC AGA GAC

N   S   K   N   T   L   Y   L   Q   M   N   S   L   R   A   E   D   T
  217   AAT TCC AAG AAC ACG CTG TAT CTT CAA ATG AAC AGC CTG AGA GCC GAG GAC ACG

CDR3
                             ~~~~~~~~~~~~~~~~~~~~~~~~~~~~~~~~~
         A   V   Y   Y   C   A   R   D   T   Y   A   M   D   V   W   G   Q   G
  271   GCC GTG TAT TAC TGT GCG AGA GAT ACC TAC GCT ATG GAC GTC TGG GGC CAA GGG
                                         └──→ JH6b

T   T   V   T   V   S   S
  325   ACC ACG GTC ACC GTC TCC TCT
```

Figure 2A

Anti-O8E 2A7VK
　　　V-segment:　　A27
　　　J-segment:　　JK2

```
            E   I   V   L   T   Q   S   P   G   T   L   S   L   S   P   G   E   R
  1         GAA ATT GTG TTG ACG CAG TCT CCA GGC ACC CTG TCT TTG TCT CCA GGG GAA AGA
                                                          CDR1
                                          ~~~~~~~~~~~~~~~~~~~~~~~~~~~~~~~~~~~~~~~~
            A   T   L   S   C   R   A   S   Q   S   V   S   S   S   Y   L   A   W
 55         GCC ACC CTC TCC TGC AGG GCC AGT CAG AGT GTT AGC AGC AGC TAC TTA GCC TGG
                                                                          CDR2
                                                                  ~~~~~~~~~~~~~~~~
            Y   Q   Q   K   P   G   Q   A   P   R   L   L   I   Y   G   A   S   S
109         TAC CAG CAG AAA CCT GGC CAG GCT CCC AGG CTC CTC ATC TAT GGT GCA TCC AGC
                CDR2
            ~~~~~~~~~~~
            R   A   T   G   I   P   D   R   F   S   G   S   G   S   G   T   D   F
163         AGG GCC ACT GGC ATC CCA GAC AGG TTC AGT GGC AGT GGG TCT GGG ACA GAC TTC
                                                                              CDR3
                                                                              ~~~~
            T   L   T   I   S   R   L   E   P   E   D   F   A   V   Y   Y   C   Q
217         ACT CTC ACC ATC AGC AGA CTG GAG CCT GAA GAT TTT GCA GTG TAT TAC TGT CAG
                        CDR3
            ~~~~~~~~~~~~~~~~~~~~~~~~~~~~~~~~~~
            Q   Y   G   S   S   P   M   Y   T   F   G   Q   G   T   K   L   E   I
271         CAG TAT GGT AGC TCA CCC ATG TAC ACT TTT GGC CAG GGG ACC AAG CTG GAG ATC
                                            └──► JK2
            K
325         AAA
```

Figure 2B

Anti-O8E 2F9VH

V-segment: VH3-53
D-segment: D5-24
J-segment: JH6b

```
        E   V   Q   L   V   E   S   G   G   G   L   I   Q   P   G   G   S   L
  1     GAG GTG CAG TTG GTG GAG TCT GGA GGA GGC TTG ATC CAG CCT GGG GGG TCC CTG
                                                               CDR 1
                                                               ~~~~~~~~~~~~~~~~
        R   L   S   C   A   A   S   G   F   I   V   S   R   N   Y   M   N   W
  55    AGA CTC TCC TGT GCA GCC TCT GGG TTC ATC GTC AGT AGA AAC TAC ATG AAC TGG
                                                               CDR 2
                                                               ~~~~~~~~~~~~~~~~
        V   R   Q   A   P   G   K   G   L   E   W   V   S   V   I   Y   G   S
  109   GTC CGC CAG GCT CCA GGG AAG GGG CTG GAG TGG GTC TCA GTT ATT TAT GGC AGT
                    CDR 2
        ~~~~~~~~~~~~~~~~~~~~~~~~~~~~~~~~~~~~~~~~
        G   R   T   D   C   A   D   S   V   K   G   R   F   T   I   S   R   D
  163   GGT AGG ACA GAC TGC GCA GAC TCC GTG AAG GGC CGA TTC ACC ATC TCC AGA GAC

N   S   K   N   T   L   Y   L   Q   M   N   S   L   R   A   E   D   T
  217   AAT TCC AAG AAC ACG CTG TAT CTT CAA ATG AAC AGC CTG AGA GCC GAG GAC ACG
                                                       CDR 3
                                                       ~~~~~~~~~~~~~~~~~~~~~~~~
        A   V   Y   Y   C   A   R   D   G   D   Y   G   M   D   V   W   G   Q
  271   GCC GTG TAT TAC TGT GCG AGA GAT GGG GAC TAC GGT ATG GAC GTC TGG GGC AAA
                                    |    D5-24    |   └──→ JH6b

G   T   T   V   T   V   S   S
  325   GGG ACC ACG GTC ACC GTC TCC TCA
```

Figure 3A

Anti O8E 2F9VK

V-segment: A27
    J-segment: JK2

```
       E   I   V   L   T   Q   S   P   G   T   L   S   L   S   P   G   E   R
  1    GAA ATT GTG TTG ACG CAG TCT CCA GGC ACC CTG TCT TTG TCT CCA GGG GAA AGA
                                              CDR 1
                                       ~~~~~~~~~~~~~~~~~~~~~~~~~~~~~~~~~~~~~~
       A   T   L   S   C   R   A   S   Q   S   V   S   S   S   Y   L   A   W
 55    GCC ACC CTC TCC TGC AGG GCC AGT CAG AGT GTT AGC AGC AGC TAC TTA GCC TGG
                                                                     CDR 2
                                                                ~~~~~~~~~~~~~~
       Y   Q   Q   K   P   G   Q   A   P   R   L   L   I   Y   G   A   S   S
109    TAC CAG CAG AAA CCT GGC CAG GCT CCC AGG CTC CTC ATC TAT GGT GCA TCC AGC
          CDR 2
       ~~~~~~~~~~~
       R   A   T   G   I   P   D   R   F   S   G   S   G   S   G   T   D   F
163    AGG GCC ACT GGC ATC CCA GAC AGG TTC AGT GGC AGT GGG TCT GGG ACA GAC TTC
                                                                         CDR 3
                                                                         ~~~
       T   L   T   I   S   R   L   E   P   E   D   F   A   V   Y   Y   C   Q
217    ACT CTC ACC ATC AGC AGA CTG GAG CCT GAA GAT TTT GCA GTG TAT TAC TGT CAG
                 CDR 3
       ~~~~~~~~~~~~~~~~~~~~~~~~~~~~~~~~~~~~
       Q   Y   G   S   S   P   L   Y   T   F   G   Q   G   T   K   L   E   I
271    CAG TAT GGT AGC TCA CCT CTG TAC ACT TTT GGC CAG GGG ACC AAG CTG GAG ATC
                                   └─► JK2
       K
325    AAA
```

Figure 3B

Anti-O8E 12E1 VH

V segment:    3-9
    D segment:    3-10
    J segment:    JH6b

```
            E   V   Q   L   V   E   S   G   G   G   L   V   Q   P   G   R   S   L
   1        GAA GTG CAG CTG GTG GAG TCT GGG GCA GGC TTG GTA CAG CCT GGC AGG TCC CTG
                                                                CDR1
                                                                ------------------
            R   L   S   C   V   A   S   G   F   T   F   D   D   Y   A   M   H   W
  55        AGA CTC TCC TGT GTA GCC TCT GGA TTC ACC TTT GAT GAT TAT GCC ATG CAC TGG
                                                                            CDR2
                                                                            ------
            V   R   Q   A   P   G   K   G   L   E   W   V   S   G   I   S   W   N
 109        GTC CGG CAA GCT CCA GGG AAG GGC CTG GAG TGG GTC TCA GGT ATT AGT TGG AAT
                    CDR2
            ------------------------------------------
            S   G   S   I   G   Y   A   D   S   V   K   G   R   F   T   I   S   R
 163        AGT GGT AGC ATA GGC TAT GCG GAC TCT GTG AAG GGC CGA TTC ACC ATC TCC AGA

D   N   A   K   N   S   L   Y   L   Q   M   N   S   L   R   A   E   D
 217        GAC AAC GCC AAG AAC TCC CTG TAT CTG CAA ATG AAC AGT CTG AGA GCT GAG GAC
                                                                CDR3
                                                                ------------------
            T   A   L   Y   Y   C   T   K   A   L   Y   G   S   G   S   S   D   F
 271        ACG GCC TTG TAT TAC TGT ACA AAA GCC CTC TAT GGT TCG GGA AGT TCT GAC TTC
                                                                                 |
                                                                                 →
                                                                               JH6b
                    CDR3
            ------------------------
            Y   Y   Y   G   M   D   V   W   G   Q   G   T   T   V   A   V   S   S
 325        TAC TAC TAC GGT ATG GAC GTC TGG GGC CAA GGG ACC ACG GTC GCC GTC TCC TCA
```

Figure 4A

Anti-O8E 12E1 VK

V segment:    L6
    J segment:    JK1

```
       E   I   V   L   T   Q   S   P   A   T   L   S   L   S   P   G   E   R
  1    GAA ATT GTG TTG ACA CAG TCT CCA GCC ACC CTG TCT TTG CCT CCA GGG GAA AGA
                                              CDR1
                                  ------------------------------------------
       A   T   L   S   C   R   A   S   Q   S   V   S   S   Y   L   A   W   Y
 55    GCC ACC CTC TCC TGC AGG GCC AGT CAG AGT GTT AGC AGC TAC TTA GCC TGG TAC
                                                                      CDR2
                                                              -----------------
       Q   Q   K   P   G   Q   A   P   R   L   L   I   Y   D   A   S   N   R
109    CAA CAG AAA CCT GGC CAG GCT CCC AGG CTC CTC ATC TAT GAT GCA TCC AAC AGG
       CDR2
       -------
       A   T   G   I   P   A   R   F   S   G   S   G   S   G   T   D   F   T
163    GCC ACT GGC ATC CCA GCC AGG TTC AGT GGC AGT GGG TCT GGG ACA GAC TTC ACT
                                                                          CDR3
                                                                          -----
       L   T   I   S   S   L   E   P   E   D   F   A   V   Y   Y   C   Q   Q
217    CTC ACC ATC AGC AGC CTA GAG CCT GAA GAT TTT GCA GTT TAT TAC TGT CAG CAG

CDR3
       -------------
       R   R   T   F   G   Q   G   T   K   V   E   I   K
271    CGT AGG ACG TTC GGC CAA GGG ACC AAG GTG GAA ATC AAA
```

Figure 4B

Anti-O8E 13D12 VH

V segment:    4-34
    D segment:    3-9
    J segment:    JH6b

```
          Q   V   Q   L   Q   Q   W   G   A   G   L   L   K   P   S   E   T   L
   1      CAG GTG CAG CTA CAG CAG TGG GGC GCA GGA CTG TTG AAG CCT TCG GAG ACC CTG

CDR1
                                                          ~~~~~~~~~~~~~~~~~~~~~
          S   L   T   C   A   V   Y   G   G   S   F   S   G   Y   Y   W   S   W
   55     TCC CTC ACC TGC GCT GTC TAT GGT GGG TCC TTC AGT GGT TAC TAC TGG AGC TGG

CDR2
                                                                ~~~~~~~~~~~~~~~~
          I   R   Q   P   P   G   K   G   L   E   W   I   G   K   I   N   H   S
   109    ATC CGC CAG CCC CCA GGG AAG GGG CTG GAG TGG ATT GGG AAA ATC AAT CAT AGC

CDR2
          ~~~~~~~~~~~~~~~~~~~~~~~~~~~~~~~~~~~~~~~~~~~~~~~~~~
          G   S   T   N   Y   N   P   S   L   K   S   R   V   T   I   S   V   D
   163    GGA AGT ACC AAC TAC AAC CCG TCC CTC AAG AGT CGA GTC ACC ATA TCA GTA GAC

T   S   K   N   Q   F   S   L   K   L   N   S   V   T   A   A   D   T
   217    ACG TCC AAG AAC CAG TTC TCC CTG AAA CTA AAC TCT GTG ACC GCC GCG GAC ACG

CDR3
                                  ~~~~~~~~~~~~~~~~~~~~~~~~~~~~~~~~~~~~~~~~~~~~~
          A   V   Y   Y   C   A   R   E   L   R   Y   F   E   N   Y   Y   Y   G
   271    GCT GTG TAT TAC TGT GCG AGA GAA TTA CGA TAT TTT GAA AAC TAC TAC TAC GGT
                                                              └──► JH6b

CDR3
          ~~~~~~~~~~~~~
          M   D   V   W   G   Q   G   T   T   V   T   V   S   S
   325    ATG GAC GTC TGG GGC CAA GGG ACC ACG GTC ACC GTC TCC TCA
```

Figure 5A

Anti-O8E 13D12 VK

V segment:    A27
J segment:    JK1

```
       E   I   V   L   T   Q   S   P   G   T   L   S   L   S   P   G   E   R
  1   GAA ATT GTG TTG ACG CAG TCT CCA GGC ACC CTG TCT TTG TCT CCA GGG GAA AGA
                                          CDR1
                                          ~~~~~~~~~~~~~~~~~~~~~~~~~~~~~~~~~~~
       A   T   L   S   C   R   A   S   Q   S   V   S   S   S   Y   L   A   W
 55   GCC ACC CTC TCC TGC AGG GCC AGT CAG AGT GTT AGC AGC AGC TAC TTA GCC TGG
                                                                      CDR2
                                                                      ~~~~~~~
       Y   Q   Q   K   P   G   Q   A   P   R   L   L   I   Y   G   A   S   S
109   TAC CAG CAG AAA CCT GGC CAG GCT CCC AGG CTC CTC ATC TAT GGT GCA TCC AGC
           CDR2
      ~~~~~~~~~~
       R   A   T   G   I   P   D   R   F   S   G   S   G   S   G   T   D   F
163   AGG GCC ACT GGC ATC CCA GAC AGG TTC AGT GGC AGT GGG TCT GGG ACA GAC TTC
                                                                          CDR3
                                                                          ~~~~
       T   L   T   I   S   R   L   E   P   E   D   F   A   V   Y   Y   C   Q
217   ACT CTC ACC ATC AGC AGA CTG GAG CCT GAA GAT TTT GCA GTG TAT TAC TGT CAG
           CDR3
      ~~~~~~~~~~~~~~~~~~~~~~~~~~~~~~~~~
       Q   Y   G   S   S   P   R   T   F   G   Q   G   T   K   V   E   I   K
271   CAG TAT GGT AGC TCA CCT CGG ACG TTC GGC CAA GGG ACC AAG GTG GAA ATC AAA
```

Figure 5B

Anti-O8E 1G11 and 13D12 VH regions

```
                                                              CDR1
4-34 germline   Q V Q L Q Q W G A G L L K P S E T L S L T C A V Y G G S F S G Y Y W S W I R
1G11 VH         - - - - - - - - - - - - - - - - - - - - - - - - - - - - D - E - T - - - -
13D12 VH        - - - - - - - - - - - - - - - - - - - - - - - - - - - - - - - - - - - - - -

CDR2
4-34 germline   Q P P G K G L E W I G E I N H S G S T N Y N P S L K S R V T I S V D T S K N
1G11 VH         - - - - - - - - - - - - - - - - - - - - - - - - - - - - - - - - A - - - -
13D12 VH        - - - - - - - - - - - - - K - - - - - T - - - - - - - - - - - - - - - - -

CDR3
4-34 germline   Q F S L K L S S V T A A D T A V Y Y C A R
1G11 VH         - - - - - - - - - - - - - - - - - - - - * L S S W S N * * W A F E Y W G Q G T L
13D12 VH        - - - - - N - - - - - - - - - - - - - - E - R Y F E - Y Y Y G M D V - - - - T

1G11 VH:        V T V S S
13D12 VH:       - - - - -
```

Note: * = a gap and there is no aa at this position.

Figure 6

Anti-O8E 2A7 and 2F9 VH regions

```
                                                          CDR1
3-53 germline   E V Q L V E S G G G L I Q P G G S L R L S C A A S G F T V S S N Y M S W V R
2A7 VH          - - - - - - - - - - - - - - - - - - - - - - - - - H - - - R - - - - - - -
2F9 VH          - - - - - - - - - - - - - - - - - - - - - - - - - - - - - - - N - N - - -

CDR2
3-53 germline   Q A P G K G L E W V S V I Y S G G S T Y Y A D S V K G R F T I S R D N S K N
2A7 VH          - - - - - - - - - - - - - G S - R - - - - - - - - - V - - - - - - - - - -
2F9 VH          - - - - - - - - - - - - - G S - R - D C - - - - - - - - - - - - - - - - -

CDR3
3-53 germline   T L Y L Q M N S L R A E D T A V Y Y C A R
JH6b germline                                             Y G M D V W G Q G T T V T V S S
2A7 VH          - - - - - - - - - - - - - - - - - - - -   D T * - A - - - - - - - - - - -
2F9 VH          - - - - - - - - - - - - - - - - - - - -   D G D - - - - - - - - - - - - -
```

Note: * = a gap and there is no aa at this position.

Figure 7

Anti-O8E 12E1 VH Region

```
                                              CDR1
3-9 Germline:    E V Q L V E S G G G L V Q P G R S L R L S C A A S G F T F D D Y A M H
12E1 VH:                                         V CDR2
3-9 Germline:    W V R Q A P G K G L E W V S G I S W N S G S I G Y A D S V K G R F T I
12E1 VH:

CDR3
3-9 Germline:    S R D N A K N S L Y L Q M N S L R A E D T A L Y Y C A K D           Y G S G S
D 3-10 Germline:                                                       T   A L
12E1 VH:

CDR3
JH6b Germline:   Y Y Y Y Y G M D V W G Q G T T V T V S S    (JH6b)
12E1 VH:         S D F                             A
```

Figure 8

Anti-O8E 1G11, 2A7, 2F9, and 13D12 VK regions

```
                              CDR1
A27 germline  E I V L T Q S P G T L S L S P G E R A T L S C R A S Q S V S S S Y L A W
1G11 VK       - - - - - - - - - F - - - - - - - - - - - - - - - - - - - T - - - - -
2A7 VK        - - - - - - - - - - - - - - - - - - - - - - - - - - - - - - - - - - -
2F9 VK        - - - - - - - - - - - - - - - - - - - - - - - - - - - - - - - - - - -
13D12 VK:     - - - - - - - - - - - - - - - - - - - - - - - - - - - - - - - - - - -

CDR2
A27 germline  Y Q Q K P G Q A P R L L I Y G A S S R A T G I P D R F S G S G S G T D F
1G11 VK       - - - - - - - - - - - V - - - - - - R - - - - - - - - - - - - - - - -
2A7 VK        - - - - - - - - - - - - - - - - - - - - - - - - - - - - - - - - - - -
2F9 VK        - - - - - - - - - - - - - - - - - - - - - - - - - - - - - - - - - - -
13D12 VK:     - - - - - - - - - - - - - - - - - - - - - - - - - - - - - - - - - - -

CDR3
A27 germline  T L T I S R L E P E D F A V Y Y C Q Q Y G S S P L * T F G G G T K V E I K
1G11 VK       - - - - - - - - - - - - - - - - - - - - - - - - M Y - - - - - L - - - -
2A7 VK        - - - - - - - - - - - - - - - - - - - - - - - - - Y - - - - Q L - - - -
2F9 VK        - - - - - - - - - - - - - - - - - - - - - - - - - Y - - - - Q - - - - -
13D12 VK:     - - - - - - - - - - - - - - - - - - - - - - - - R * - - - - Q - - - - -
```

Note: * = a gap and there is no aa at this position.

Figure 9

Anti-O8E 12E1 VK Region

```
                                                  CDR1
L6 Germline:    E I V L T Q S P A T L S L S P G E R A T L S C R A S Q S V S S Y L A
12E1 VK:        - - - - - - - - - - - - - - - - - - - - - - - - - - - - - - - - -

CDR2
L6 Germline:    W Y Q Q K P G Q A P R L L I Y D A S N R A T G I P A R F S G G S G S G
12E1 VK:        - - - - - - - - - - - - - - - - - - - - - - - - - - - - - - - - -

CDR3
L6 Germline:    T D F T L T I S S L E P E D F A V Y Y C Q Q R S N W
JK1 Germline:                                                      - T F G Q G T K V
12E1 VK:        - - - - - - - - - - - - - - - - - - - - - R        -           -

JK1 Germline:   E I K
12E1 VK:        - - -
```

Mapping of O8E epitope(s) with HuMabs

SEQUENCE LISTING

<160> NUMBER OF SEQ ID NOS: 58

<210> SEQ ID NO 1
<211> LENGTH: 118
<212> TYPE: PRT
<213> ORGANISM: Homo sapiens

<400> SEQUENCE: 1

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Phe Trp Thr Trp Ile Arg Gln Pro Pro Gly Lys Gly Leu Glu Trp Ile
        35                  40                  45

Gly Glu Ile Asn His Ser Gly Thr Thr Asn Tyr Asn Pro Ser Leu Lys
    50                  55                  60

Ser Arg Val Thr Ile Ser Ala Asp Thr Ser Lys Asn Gln Phe Ser Arg
65                  70                  75                  80

Leu Ser Ser Val Thr Ala Ala Asp Thr Ala Val Tyr Tyr Cys Ala Arg
                85                  90                  95

Leu Ser Ser Trp Ser Asn Trp Ala Phe Glu Tyr Trp Gly Gln Gly Thr
            100                 105                 110

Leu Val Thr Val Ser Ser
        115

<210> SEQ ID NO 2
<211> LENGTH: 115
<212> TYPE: PRT
<213> ORGANISM: Homo sapiens

<400> SEQUENCE: 2

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Asn Trp Val Arg Gln Ala Pro Gly Lys Gly Leu Glu Trp Val
        35                  40                  45

Ser Val Ile Tyr Gly Ser Gly Arg Thr Tyr Tyr Ala Asp Ser Val Lys
    50                  55                  60

Gly Arg Val Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Thr Tyr Ala Met Asp Val Trp Gly Gln Gly Thr Thr Val Thr
            100                 105                 110

Val Ser Ser
        115

<210> SEQ ID NO 3
<211> LENGTH: 116
<212> TYPE: PRT
<213> ORGANISM: Homo sapiens

<400> SEQUENCE: 3

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Val Ser Arg Asn
            20                  25                  30

```
Tyr Met Asn Trp Val Arg Gln Ala Pro Gly Lys Gly Leu Glu Trp Val
            35                  40                  45

Ser Val Ile Tyr Gly Ser Gly Arg Thr Asp Cys Ala Asp Ser Val Lys
        50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Arg Asp Gly Asp Tyr Gly Met Asp Val Trp Gly Gln Gly Thr Thr Val
               100                 105                 110

Thr Val Ser Ser
            115

<210> SEQ ID NO 4
<211> LENGTH: 126
<212> TYPE: PRT
<213> ORGANISM: Homo sapiens

<400> SEQUENCE: 4

Glu Val Gln Leu Val Glu Ser Gly Gly Gly Leu Val Gln Pro Gly Arg
 1               5                  10                  15

Ser Leu Arg Leu Ser Cys Val Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                85                  90                  95

Thr Lys Ala Leu Tyr Gly Ser Gly Ser Ser Asp Phe Tyr Tyr Tyr Gly
               100                 105                 110

Met Asp Val Trp Gly Gln Gly Thr Thr Val Ala Val Ser Ser
               115                 120                 125

<210> SEQ ID NO 5
<211> LENGTH: 122
<212> TYPE: PRT
<213> ORGANISM: Homo sapiens

<400> SEQUENCE: 5

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Lys Ile Asn His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
 65                  70                  75                  80

Lys Leu Asn Ser Val Thr Ala Ala Asp Thr Ala Val Tyr Tyr Cys Ala
                85                  90                  95

Arg Glu Leu Arg Tyr Phe Glu Asn Tyr Tyr Tyr Gly Met Asp Val Trp
               100                 105                 110
```

```
Gly Gln Gly Thr Thr Val Thr Val Ser Ser
        115                 120
```

```
<210> SEQ ID NO 6
<211> LENGTH: 108
<212> TYPE: PRT
<213> ORGANISM: Homo sapiens

<400> SEQUENCE: 6

Glu Ile Val Leu Thr Gln Phe Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp Tyr Gln Gln Lys Pro Gly Gln Ala Pro Arg Val Leu
        35                  40                  45

Ile Tyr Gly Ala Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105
```

```
<210> SEQ ID NO 7
<211> LENGTH: 109
<212> TYPE: PRT
<213> ORGANISM: Homo sapiens

<400> SEQUENCE: 7

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Met Tyr Thr Phe Gly Gln Gly Thr Lys Leu Glu Ile Lys
            100                 105
```

```
<210> SEQ ID NO 8
<211> LENGTH: 109
<212> TYPE: PRT
<213> ORGANISM: Homo sapiens

<400> SEQUENCE: 8

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45
```

Ile Tyr Gly Ala Ser Ser Arg Ala Thr Gly Ile Pro Asp Arg Phe Ser
            50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                85                  90                  95

Leu Tyr Thr Phe Gly Gln Gly Thr Lys Leu Glu Ile Lys
            100                 105

<210> SEQ ID NO 9
<211> LENGTH: 103
<212> TYPE: PRT
<213> ORGANISM: Homo sapiens

<400> SEQUENCE: 9

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Arg Thr Phe Gly Gln
                85                  90                  95

Gly Thr Lys Val Glu Ile Lys
            100

<210> SEQ ID NO 10
<211> LENGTH: 108
<212> TYPE: PRT
<213> ORGANISM: Homo sapiens

<400> SEQUENCE: 10

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                85                  90                  95

Arg Thr Phe Gly Gln Gly Thr Lys Val Glu Ile Lys
            100                 105

<210> SEQ ID NO 11
<211> LENGTH: 5
<212> TYPE: PRT
<213> ORGANISM: Homo sapiens

<400> SEQUENCE: 11

Asp Tyr Phe Trp Thr

```
<210> SEQ ID NO 12
<211> LENGTH: 6
<212> TYPE: PRT
<213> ORGANISM: Homo sapiens

<400> SEQUENCE: 12

Ser Asn Tyr Met Asn Trp
1               5

<210> SEQ ID NO 13
<211> LENGTH: 5
<212> TYPE: PRT
<213> ORGANISM: Homo sapiens

<400> SEQUENCE: 13

Arg Asn Tyr Met Asn
1               5

<210> SEQ ID NO 14
<211> LENGTH: 5
<212> TYPE: PRT
<213> ORGANISM: Homo sapiens

<400> SEQUENCE: 14

Asp Tyr Ala Met His
1               5

<210> SEQ ID NO 15
<211> LENGTH: 5
<212> TYPE: PRT
<213> ORGANISM: Homo sapiens

<400> SEQUENCE: 15

Gly Tyr Tyr Trp Ser
1               5

<210> SEQ ID NO 16
<211> LENGTH: 16
<212> TYPE: PRT
<213> ORGANISM: Homo sapiens

<400> SEQUENCE: 16

Glu Ile Asn His Ser Gly Thr Thr Asn Tyr Asn Pro Ser Leu Lys Ser
1               5                   10                  15

<210> SEQ ID NO 17
<211> LENGTH: 16
<212> TYPE: PRT
<213> ORGANISM: Homo sapiens

<400> SEQUENCE: 17

Val Ile Tyr Gly Ser Gly Arg Thr Tyr Tyr Ala Asp Ser Val Lys Gly
1               5                   10                  15

<210> SEQ ID NO 18
<211> LENGTH: 16
<212> TYPE: PRT
<213> ORGANISM: Homo sapiens

<400> SEQUENCE: 18

Val Ile Tyr Gly Ser Gly Arg Thr Asp Cys Ala Asp Ser Val Lys Gly
1               5                   10                  15
```

```
<210> SEQ ID NO 19
<211> LENGTH: 17
<212> TYPE: PRT
<213> ORGANISM: Homo sapiens

<400> SEQUENCE: 19

Gly Ile Ser Trp Asn Ser Gly Ser Ile Gly Tyr Ala Asp Ser Val Lys
1               5                   10                  15
Gly

<210> SEQ ID NO 20
<211> LENGTH: 16
<212> TYPE: PRT
<213> ORGANISM: Homo sapiens

<400> SEQUENCE: 20

Lys Ile Asn His Ser Gly Ser Thr Asn Tyr Asn Pro Ser Leu Lys Ser
1               5                   10                  15

<210> SEQ ID NO 21
<211> LENGTH: 11
<212> TYPE: PRT
<213> ORGANISM: Homo sapiens

<400> SEQUENCE: 21

Leu Ser Ser Trp Ser Asn Trp Ala Phe Glu Tyr
1               5                   10

<210> SEQ ID NO 22
<211> LENGTH: 7
<212> TYPE: PRT
<213> ORGANISM: Homo sapiens

<400> SEQUENCE: 22

Asp Thr Tyr Ala Met Asp Val
1               5

<210> SEQ ID NO 23
<211> LENGTH: 8
<212> TYPE: PRT
<213> ORGANISM: Homo sapiens

<400> SEQUENCE: 23

Asp Gly Asp Tyr Gly Met Asp Val
1               5

<210> SEQ ID NO 24
<211> LENGTH: 16
<212> TYPE: PRT
<213> ORGANISM: Homo sapiens

<400> SEQUENCE: 24

Leu Tyr Gly Ser Gly Ser Ser Asp Phe Tyr Tyr Gly Met Asp Val
1               5                   10                  15

<210> SEQ ID NO 25
<211> LENGTH: 14
<212> TYPE: PRT
<213> ORGANISM: Homo sapiens

<400> SEQUENCE: 25

Glu Leu Arg Tyr Phe Glu Asn Tyr Tyr Gly Met Asp Val
1               5                   10
```

<210> SEQ ID NO 26
<211> LENGTH: 12
<212> TYPE: PRT
<213> ORGANISM: Homo sapiens

<400> SEQUENCE: 26

Arg Ala Ser Gln Ser Val Ser Ser Thr Tyr Leu Ala
1               5                   10

<210> SEQ ID NO 27
<211> LENGTH: 12
<212> TYPE: PRT
<213> ORGANISM: Homo sapiens

<400> SEQUENCE: 27

Arg Ala Ser Gln Ser Val Ser Ser Ser Tyr Leu Ala
1               5                   10

<210> SEQ ID NO 28
<211> LENGTH: 12
<212> TYPE: PRT
<213> ORGANISM: Homo sapiens

<400> SEQUENCE: 28

Arg Ala Ser Gln Ser Val Ser Ser Ser Tyr Leu Ala
1               5                   10

<210> SEQ ID NO 29
<211> LENGTH: 11
<212> TYPE: PRT
<213> ORGANISM: Homo sapiens

<400> SEQUENCE: 29

Arg Ala Ser Gln Ser Val Ser Ser Tyr Leu Ala
1               5                   10

<210> SEQ ID NO 30
<211> LENGTH: 12
<212> TYPE: PRT
<213> ORGANISM: Homo sapiens

<400> SEQUENCE: 30

Arg Ala Ser Gln Ser Val Ser Ser Ser Tyr Leu Ala
1               5                   10

<210> SEQ ID NO 31
<211> LENGTH: 7
<212> TYPE: PRT
<213> ORGANISM: Homo sapiens

<400> SEQUENCE: 31

Gly Ala Ser Arg Arg Ala Thr
1               5

<210> SEQ ID NO 32
<211> LENGTH: 7
<212> TYPE: PRT
<213> ORGANISM: Homo sapiens

<400> SEQUENCE: 32

Gly Ala Ser Ser Arg Ala Thr
1               5

<210> SEQ ID NO 33

```
<211> LENGTH: 7
<212> TYPE: PRT
<213> ORGANISM: Homo sapiens

<400> SEQUENCE: 33

Gly Ala Ser Ser Arg Ala Thr
1               5

<210> SEQ ID NO 34
<211> LENGTH: 7
<212> TYPE: PRT
<213> ORGANISM: Homo sapiens

<400> SEQUENCE: 34

Asp Ala Ser Asn Arg Ala Thr
1               5

<210> SEQ ID NO 35
<211> LENGTH: 7
<212> TYPE: PRT
<213> ORGANISM: Homo sapiens

<400> SEQUENCE: 35

Gly Ala Ser Ser Arg Ala Thr
1               5

<210> SEQ ID NO 36
<211> LENGTH: 9
<212> TYPE: PRT
<213> ORGANISM: Homo sapiens

<400> SEQUENCE: 36

Gln Gln Tyr Gly Ser Ser Pro Leu Thr
1               5

<210> SEQ ID NO 37
<211> LENGTH: 10
<212> TYPE: PRT
<213> ORGANISM: Homo sapiens

<400> SEQUENCE: 37

Gln Gln Tyr Gly Ser Ser Pro Met Tyr Thr
1               5                   10

<210> SEQ ID NO 38
<211> LENGTH: 10
<212> TYPE: PRT
<213> ORGANISM: Homo sapiens

<400> SEQUENCE: 38

Gln Gln Tyr Gly Ser Ser Pro Leu Tyr Thr
1               5                   10

<210> SEQ ID NO 39
<211> LENGTH: 5
<212> TYPE: PRT
<213> ORGANISM: Homo sapiens

<400> SEQUENCE: 39

Gln Gln Arg Arg Thr
1               5

<210> SEQ ID NO 40
<211> LENGTH: 9
<212> TYPE: PRT
```

<210> SEQ ID NO 41
<211> LENGTH: 357
<212> TYPE: DNA
<213> ORGANISM: Homo sapiens

<400> SEQUENCE: 40

Gln Gln Tyr Gly Ser Ser Pro Arg Thr
1               5

<210> SEQ ID NO 41
<211> LENGTH: 357
<212> TYPE: DNA
<213> ORGANISM: Homo sapiens

<400> SEQUENCE: 41

```
caggtgcagc tacagcagtg gggcgcagga ctgttgaagc cttcggagac cctgtccctc      60
acctgcgctg tctatggtgg gtccttcagt gattacttct ggacctggat ccgccagccc     120
ccagggaagg gcctggagtg gattggggaa atcaatcata gtggaaccac caactacaac     180
ccgtccctca agagtcgagt caccatttca gcagacacgt ccaagaacca gttctccctg     240
aggctgagct ctgtgaccgc cgcggacacg gctgtgtatt actgtgcgag actcagcagc     300
tggtcgaact gggcctttga gtactggggc cagggaaccc tggtcaccgt ctcctca       357
```

<210> SEQ ID NO 42
<211> LENGTH: 345
<212> TYPE: DNA
<213> ORGANISM: Homo sapiens

<400> SEQUENCE: 42

```
gaggtgcagc tggtggagtc tggaggaggc ttgatccagc ctgggggtc cctgagactc       60
tcctgtgcag cctctgggtt caccgtcagt agcaactaca tgaactgggt ccgccaggct    120
ccagggaagg gcctggagtg ggtctcagtt atttatggca gtggtagaac atattacgca    180
gactccgtga agggccgagt caccatctcc agagacaatt ccaagaacac gctgtatctt    240
caaatgaaca gcctgagagc cgaggacacg gccgtgtatt actgtgcgag agatacctac    300
gctatggacg tctgggccca agggaccacg gtcaccgtct cctct                   345
```

<210> SEQ ID NO 43
<211> LENGTH: 348
<212> TYPE: DNA
<213> ORGANISM: Homo sapiens

<400> SEQUENCE: 43

```
gaggtgcagt tggtggagtc tggaggaggc ttgatccagc ctgggggtc cctgagactc       60
tcctgtgcag cctctgggtt catcgtcagt agaaactaca tgaactgggt ccgccaggct    120
ccagggaagg gcctggagtg gtctcagtt atttatggca gtggtaggac agactgcgca    180
gactccgtga agggccgatt caccatctcc agagacaatt ccaagaacac gctgtatctt    240
caaatgaaca gcctgagagc cgaggacacg gccgtgtatt actgtgcgag agatgggac   300
tacggtatgg acgtctgggg ccaagggacc acggtcaccg tctcctca                348
```

<210> SEQ ID NO 44
<211> LENGTH: 378
<212> TYPE: DNA
<213> ORGANISM: Homo sapiens

<400> SEQUENCE: 44

```
gaagtgcagc tggtggagtc tggggaggc ttggtacagc ctggcaggtc cctgagactc       60
tcctgtgtag cctctggatt caccttgat gattatgcca tgcactgggt ccggcaagct    120
```

```
ccagggaagg gcctggagtg ggtctcaggt attagttgga atagtggtag cataggctat    180
gcggactctg tgaagggccg attcaccatc tccagagaca acgccaagaa ctccctgtat    240
ctgcaaatga acagtctgag agctgaggac acggccttgt attactgtac aaaagccctc    300
tatggttcgg ggagttctga cttctactac tacggtatgg acgtctgggg ccaagggacc    360
acggtcgccg tctcctca                                                  378

<210> SEQ ID NO 45
<211> LENGTH: 366
<212> TYPE: DNA
<213> ORGANISM: Homo sapiens

<400> SEQUENCE: 45
caggtgcagc tacagcagtg gggcgcagga ctgttgaagc cttcggagac cctgtccctc     60
acctgcgctg tctatggtgg gtccttcagt ggttactact ggagctggat ccgccagccc    120
ccagggaagg ggctggagtg gattgggaaa atcaatcata gcggaagtac caactacaac    180
ccgtccctca agagtcgagt caccatatca gtagacacgt ccaagaacca gttctccctg    240
aaactaaact ctgtgaccgc cgcggacacg gctgtgtatt actgtgcgag agaattacga    300
tattttgaaa actactacta cggtatggac gtctggggcc aagggaccac ggtcaccgtc    360
tcctca                                                               366

<210> SEQ ID NO 46
<211> LENGTH: 324
<212> TYPE: DNA
<213> ORGANISM: Homo sapiens

<400> SEQUENCE: 46
gaaattgtgt tgacgcagtt tccaggcacc ctgtctttgt ctccagggga aagagccacc     60
ctctcctgca gggccagtca gagtgttagc agcacctact tagcctggta ccagcagaaa    120
cctggccagg ctcccagggt cctcatctat ggtgcatcca gaagggccac tggcatccca    180
gacaggttca gtggcagtgg gtctgggaca gacttcactc tcaccatcag cagactggag    240
cctgaagatt ttgcagtgta ttactgtcag cagtatggta gctcaccgct cactttcggc    300
ggagggacca aggtggagat caaa                                           324

<210> SEQ ID NO 47
<211> LENGTH: 327
<212> TYPE: DNA
<213> ORGANISM: Homo sapiens

<400> SEQUENCE: 47
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcacccat gtacactttt    300
ggccagggga ccaagctgga gatcaaa                                        327

<210> SEQ ID NO 48
<211> LENGTH: 327
<212> TYPE: DNA
<213> ORGANISM: Homo sapiens

<400> SEQUENCE: 48
```

```
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcacctct gtacactttt   300
ggccagggga ccaagctgga gatcaaa                                       327
```

<210> SEQ ID NO 49
<211> LENGTH: 309
<212> TYPE: DNA
<213> ORGANISM: Homo sapiens

<400> SEQUENCE: 49

```
gaaattgtgt tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtaggacgt tcggccaagg gaccaaggtg   300
gaaatcaaa                                                           309
```

<210> SEQ ID NO 50
<211> LENGTH: 324
<212> TYPE: DNA
<213> ORGANISM: Homo sapiens

<400> SEQUENCE: 50

```
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcacctcg gacgttcggc   300
caagggacca aggtggaaat caaa                                          324
```

<210> SEQ ID NO 51
<211> LENGTH: 97
<212> TYPE: PRT
<213> ORGANISM: Homo sapiens

<400> SEQUENCE: 51

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 52
<211> LENGTH: 97
<212> TYPE: PRT
<213> ORGANISM: Homo sapiens

<400> SEQUENCE: 52

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg

<210> SEQ ID NO 53
<211> LENGTH: 124
<212> TYPE: PRT
<213> ORGANISM: Homo sapiens

<400> SEQUENCE: 53

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Tyr Gly Ser Gly Ser Tyr Tyr Tyr Tyr Gly Met Asp
            100                 105                 110

Val Trp Gly Gln Gly Thr Thr Val Thr Val Ser Ser
        115                 120

<210> SEQ ID NO 54
<211> LENGTH: 96
<212> TYPE: PRT
<213> ORGANISM: Homo sapiens

<400> SEQUENCE: 54

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

```
Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

<210> SEQ ID NO 55
<211> LENGTH: 105
<212> TYPE: PRT
<213> ORGANISM: Homo sapiens

<400> SEQUENCE: 55

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Thr Phe
                 85                  90                  95

Gly Gln Gly Thr Lys Val Glu Ile Lys
                100                 105

<210> SEQ ID NO 56
<211> LENGTH: 282
<212> TYPE: PRT
<213> ORGANISM: Homo sapiens

<400> SEQUENCE: 56

Met Ala Ser Leu Gly Gln Ile Leu Phe Trp Ser Ile Ile Ser Ile Ile
 1               5                  10                  15

Ile Ile Leu Ala Gly Ala Ile Ala Leu Ile Ile Gly Phe Gly Ile Ser
                 20                  25                  30

Gly Arg His Ser Ile Thr Val Thr Thr Val Ala Ser Ala Gly Asn Ile
             35                  40                  45

Gly Glu Asp Gly Ile Leu Ser Cys Thr Phe Glu Pro Asp Ile Lys Leu
 50                  55                  60

Ser Asp Ile Val Ile Gln Trp Leu Lys Glu Gly Val Leu Gly Leu Val
 65                  70                  75                  80

His Glu Phe Lys Glu Gly Lys Asp Glu Leu Ser Glu Gln Asp Glu Met
                 85                  90                  95

Phe Arg Gly Arg Thr Ala Val Phe Ala Asp Gln Val Ile Val Gly Asn
                100                 105                 110

Ala Ser Leu Arg Leu Lys Asn Val Gln Leu Thr Asp Ala Gly Thr Tyr
             115                 120                 125

Lys Cys Tyr Ile Ile Thr Ser Lys Gly Lys Gly Asn Ala Asn Leu Glu
 130                 135                 140

Tyr Lys Thr Gly Ala Phe Ser Met Pro Glu Val Asn Val Asp Tyr Asn
145                  150                 155                 160

Ala Ser Ser Glu Thr Leu Arg Cys Glu Ala Pro Arg Trp Phe Pro Gln
                 165                 170                 175
```

```
Pro Thr Val Val Trp Ala Ser Gln Val Asp Gln Gly Ala Asn Phe Ser
            180             185             190

Glu Val Ser Asn Thr Ser Phe Glu Leu Asn Ser Glu Asn Val Thr Met
        195             200             205

Lys Val Val Ser Val Leu Tyr Asn Val Thr Ile Asn Asn Thr Tyr Ser
    210             215             220

Cys Met Ile Glu Asn Asp Ile Ala Lys Ala Thr Gly Asp Ile Lys Val
225             230             235             240

Thr Glu Ser Glu Ile Lys Arg Arg Ser His Leu Gln Leu Leu Asn Ser
                245             250             255

Lys Ala Ser Leu Cys Val Ser Ser Phe Phe Ala Ile Ser Trp Ala Leu
            260             265             270

Leu Pro Leu Ser Pro Tyr Leu Met Leu Lys
        275             280

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
aggatggaat cctgagctgc actt                                          24

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tccgacagct catctttgcc ttct                                          24
```

HUMAN MONOCLONAL ANTIBODIES TO O8E

CROSS-REFERENCE TO RELATED APPLICATIONS

This application is a divisional of U.S. patent application Ser. No. 12/092,866, filed Oct. 1, 2008, issued as U.S. Pat. No. 8,609,816, which is a national stage of International Application Serial No PCT/US06/61816, filed Dec. 8, 2006, which claims priority of U.S. Provisional Application Ser. No. 60/748,914, filed Dec. 8, 2005, and U.S. Provisional Application Ser. No. 60/824,593, filed Sep. 5, 2006, each of which are herein incorporated by reference.

SEQUENCE LISTING

The specification further incorporates by reference the Sequence Listing submitted herewith via EFS on Jan. 23, 2014. Pursuant to 37 C.F.R. §1.52(e)(5), the Sequence Listing text file, identified as "077375.0967 SL.TXT," is 28,449 bytes and was created on Jan. 16, 2014. The Sequence Listing, electronically filed herewith, does not extend beyond the scope of the specification and thus does not contain new matter.

TECHNICAL FIELD

The present disclosure relates generally to the fields of immunology and molecular biology. More specifically, provided herein are human anti-O8E monoclonal antibodies, nucleic acids encoding human anti-O8E monoclonal antibodies, methods for preparing human anti-O8E monoclonal antibodies and methods for the treatment of diseases, such as cancers, characterized by the growth of cells that express O8E.

BACKGROUND

Breast and ovarian cancers are the second and fourth leading causes, respectively, of cancer deaths in females in the United States (American Cancer Society (2005) Cancer facts and figures). The American Cancer Society has estimated that, in the United States, approximately 40,000 women will die of breast cancer and about 16,000 will die of ovarian cancer in 2005. Surface epithelial tumors account for over 80% of all ovarian malignancies, which include serous tumors, mucinous tumors, endometrioid tumors and clear cell carcinomas (Seidman et al. "Blaustein's Pathology of the Female Genital Tract" 791-4 (Kurman, editor, 5$^{th}$ ed. New York, Springer-Verlag, 2002). Ovarian cancers frequently present at an advanced stage where metastatic disease has spread to regional and distant sites (Pettersson, (1994) Int. Fed. Of Gyn. and Obstetrics, Vol. 22; and Heintz et al. (2001) J. Epidermiol. Biostat. 6:107-38). Thus, while the lifetime probability of developing breast cancer is significantly higher than for ovarian cancer, the 5 year survival rate for breast cancer patients is substantially better than for those with ovarian cancer.

B7-like molecules belong to the immunoglobulin (Ig) superfamily. The extracellular portion of B7-like molecules contain single IgV and IgC domains and share ~20%-40% amino acid identity. B7-like molecules play critical roles in the control and fine tuning of antigen-specific immune responses. O8E, known also as B7H4, B7x and B7S1, is a member of the B7 family and is thought to play a role in both stimulatory and inhibitory regulation of T cell responses (Carreno et al., (2002) Ann. Rev. Immunol. 20:29-53 and Khoury et al., (2004) Immunity 20:529-538). Human O8E has been mapped on chromosome 1 and is comprised of six exons and five introns spanning 66 kb, of which exon 6 is used for alternative splicing to generate two different transcripts (Choi et al. (2003) J. Immunol. 171:4650-4654).

O8E exerts its physiologic function by binding to a receptor on T cells, which in turn induces cell cycle arrest and inhibits the secretion of cytokines, the development of cytotoxicity and cytokine production of CD4$^+$ and CD8$^+$ T cells (Prasad et al. (2003) Immunity 18:863-873; Sica et al. (2003) Immunity 18:849-861; Wang et al. (2004) Microbes Infect. 6:759-66; and Zang et al. (2003) Proc. Natl. Acad. Sci. U.S.A. 100:10388-10392). It has been suggested that O8E may be an attenuator of inflammatory responses and may serve a role in down-regulation of antigen-specific immune and anti-tumor responses (Zang et al. (2003) Proc. Natl. Acad. Sci. U.S.A. 100:10388-10392; Prasad et al. (2003) Immunity 18:863-873; Sica et al. (2003) Immunity 18:849-861; Choi et al. (2003) J. Immunol. 171:4650-4654; and Carreno et al. (2003) Trends Immunol. 24:524-7).

O8E mRNA but not protein expression has been detected in a wide range of normal somatic tissues, including liver, skeletal muscle, kidney, pancreas and small bowel (Sica et al. (2003) Immunity 18:849-61 and Choi et al. (2003) J. Immunol. 171:4650-4). O8E is inducible upon stimulation of T cells, B cells, monocytes and dendritic cells; however, immunohistochemistry analysis has revealed little expression in several peripheral tissues with the exception of positive staining in some ovarian and lung cancers (Id.). In addition, O8E is consistently overexpressed in primary and metastatic breast cancer, independent of tumor grade or stage, suggesting a critical role for this protein in breast cancer biology (Tringler et al. (2005) Clinical Cancer Res. 11:1842-48). See, also, U.S. Pat. Nos. 6,962,980; 6,699,664; 6,468,546; 6,488,931; 6,670,463; and 6,528,253, each of which is incorporated by reference herein in its entirety.

A wide variety of therapeutic modalities are available for the treatment of advanced breast and ovarian cancers including radiotherapy, conventional chemotherapy with cytotoxic antitumor agents, hormone therapy (aromatase inhibitors, luteinizing-hormone releasing-hormone analogues), bisphosphonates and signal-transduction inhibitors (Smith (2002) Lancet, 360:790-2). Unfortunately, however, many patients either respond poorly or not at all to any of these therapeutic modalities. Thus, there is a need to identify new molecular markers for and therapeutic agents against breast and ovarian cancers. Accordingly, O8E represents a valuable target for the treatment of cancers, including ovarian and breast cancers and a variety of other diseases characterized by O8E expression.

SUMMARY

The present disclosure provides isolated monoclonal antibodies, in particular human sequence monoclonal antibodies, that bind to O8E (a/k/a B7H4, B7S1 and B7x) and that exhibit numerous desirable properties. These properties include high affinity binding to human O8E. Also provided are methods for treating a variety of O8E mediated diseases using the antibodies and compositions of this disclosure.

In one aspect, this disclosure pertains to an isolated monoclonal antibody or an antigen-binding portion thereof, wherein the antibody:

(a) binds to human O8E with a $K_D$ of $1 \times 10^{-7}$ M or less; and
(b) binds to human CHO cells transfected with O8E.

In certain embodiments, the antibody binds to a breast cell carcinoma tumor cell line, such as cell line SKBR3 (ATCC Accession No. HTB-30).

Typically the antibody is a human antibody, although in alternative embodiments the antibody can be a murine antibody, a chimeric antibody or humanized antibody.

In one embodiment, the antibody binds to human O8E with a $K_D$ of $5 \times 10^{-8}$ M or less, binds to human O8E with a $K_D$ of $2 \times 10^{-8}$ M or less, binds to human O8E with a $K_D$ of $1 \times 10^{-8}$ M or less, binds to human O8E with a $K_D$ of $5 \times 10^{-9}$ M or less, binds to human O8E with a $K_D$ of $4 \times 10^{-9}$ M or less, binds to human O8E with a $K_D$ of $3 \times 10^{-9}$ M or less or binds to human O8E with a $K_D$ of $2 \times 10^{-9}$ M or less.

In another embodiment, the antibody is internalized by SKBR3 breast cell carcinoma tumor cells after binding to O8E expressed on those cells.

In another embodiment, this disclosure provides an isolated monoclonal antibody or antigen binding portion thereof, wherein the antibody cross-competes for binding to O8E with a reference antibody, wherein the reference antibody:
  (a) binds to human O8E with a $K_D$ of $1 \times 10^{-7}$ M or less; and
  (b) binds to human CHO cells transfected with O8E.
In various embodiments, the reference antibody comprises:
  (a) a heavy chain variable region comprising the amino acid sequence of SEQ ID NO: 1; and
  (b) a light chain variable region comprising the amino acid sequence of SEQ ID NO: 6;
or the reference antibody comprises:
  (a) a heavy chain variable region comprising the amino acid sequence of SEQ ID NO: 2; and
  (b) a light chain variable region comprising the amino acid sequence of SEQ ID NO: 7;
or the reference antibody comprises:
  (a) a heavy chain variable region comprising the amino acid sequence of SEQ ID NO: 3; and
  (b) a light chain variable region comprising the amino acid sequence of SEQ ID NO: 8
or the reference antibody comprises:
  (a) a heavy chain variable region comprising the amino acid sequence of SEQ ID NO: 4; and
  (b) a light chain variable region comprising the amino acid sequence of SEQ ID NO: 9.
or the reference antibody comprises:
  (a) a heavy chain variable region comprising the amino acid sequence of SEQ ID NO: 5; and
  (b) a light chain variable region comprising the amino acid sequence of SEQ ID NO: 10.

In one aspect, this disclosure pertains to an isolated monoclonal antibody or an antigen-binding portion thereof, comprising a heavy chain variable region that is the product of or derived from a human $V_H$ 4-34 gene (the protein product of which is presented herein as SEQ ID NO: 51), wherein the antibody specifically binds O8E. This disclosure also provides an isolated monoclonal antibody or an antigen-binding portion thereof, comprising a heavy chain variable region that is the product of or derived from a human $V_H$ 3-53 gene (the protein product of which is presented herein as SEQ ID NO: 52), wherein the antibody specifically binds O8E. This disclosure also provides an isolated monoclonal antibody or an antigen-binding portion thereof, comprising a heavy chain variable region that is the product of or derived from a combination of human $V_H$ 3-9/D3-10/JH6b genes (the protein product of which is presented herein as SEQ ID NO: 53), wherein the antibody specifically binds O8E.

This disclosure still further provides an isolated monoclonal antibody or an antigen-binding portion thereof, comprising a light chain variable region that is the product of or derived from a human $V_K$ A27 gene (the protein product of which is presented herein as SEQ ID NO: 54), wherein the antibody specifically binds O8E. This disclosure still further provides an isolated monoclonal antibody or an antigen-binding portion thereof, comprising a light chain variable region that is the product of or derived from a combination of human $V_K$ L6/JK1 genes (the protein product of which is presented herein as SEQ ID NO: 55), wherein the antibody specifically binds O8E.

In other aspects, this disclosure provides an isolated monoclonal antibody or an antigen-binding portion thereof, comprising:
  (a) a heavy chain variable region of a human $V_H$ 4-34, 3-53 or 3-9 gene; and
  (b) a light chain variable region of a human $V_K$ A27 or $V_K$ L6;
  wherein the antibody specifically binds to O8E.

In a related embodiment, the antibody comprises a heavy chain variable region of a human $V_H$ 4-34 gene and a light chain variable region of a human $V_K$ A27 gene. In another related embodiment, the antibody comprises a heavy chain variable region of a human $V_H$ 3-53 gene and a light chain variable region of a human $V_K$ A27 gene. In yet another related embodiment, the antibody comprises a heavy chain variable region of a human $V_H$ 3-9 gene and a light chain variable region of a human $V_K$ L6 gene.

In yet another aspect, the present disclosure provides an isolated monoclonal antibody or antigen binding portion thereof, comprising:
  a heavy chain variable region that comprises CDR1, CDR2 and CDR3 sequences; and a light chain variable region that comprises CDR1, CDR2 and CDR3 sequences, wherein:
  (a) the heavy chain variable region CDR3 sequence comprises an amino acid sequence selected from the group consisting of amino acid sequences of SEQ ID NOs: 21, 22, 23, 24 and 25 and conservative modifications thereof;
  (b) the light chain variable region CDR3 sequence comprises an amino acid sequence selected from the group consisting of amino acid sequence of SEQ ID NOs: 36, 37, 38, 39 and 40 and conservative modifications thereof;
  (c) the antibody binds to human O8E with a $K_D$ of $1 \times 10^{-7}$ M or less;
  (d) binds to human CHO cells transfected with O8E.

Typically, the heavy chain variable region CDR2 sequence comprises an amino acid sequence selected from the group consisting of amino acid sequences of SEQ ID NOs: 16, 17, 18, 19 and 20 and conservative modifications thereof; and the light chain variable region CDR2 sequence comprises an amino acid sequence selected from the group consisting of amino acid sequences of SEQ ID NOs: 31, 32, 33, 34 and 35 and conservative modifications thereof. Typically, the heavy chain variable region CDR1 sequence comprises an amino acid sequence selected from the group consisting of amino acid sequences of SEQ ID NOs: 11, 12, 13, 14 and 15 and conservative modifications thereof; and the light chain variable region CDR1 sequence comprises an amino acid sequence selected from the group consisting of amino acid sequences of SEQ ID NOs: 26, 27, 28, 29 and 30 and conservative modifications thereof.

A particular combination comprises:
  (a) a heavy chain variable region CDR1 comprising SEQ ID NO: 11;

(b) a heavy chain variable region CDR2 comprising SEQ ID NO: 16;
(c) a heavy chain variable region CDR3 comprising SEQ ID NO: 21;
(d) a light chain variable region CDR1 comprising SEQ ID NO: 26;
(e) a light chain variable region CDR2 comprising SEQ ID NO: 31; and
(f) a light chain variable region CDR3 comprising SEQ ID NO: 36.

Another particular combination comprises:
(a) a heavy chain variable region CDR1 comprising SEQ ID NO: 12;
(b) a heavy chain variable region CDR2 comprising SEQ ID NO: 17;
(c) a heavy chain variable region CDR3 comprising SEQ ID NO: 22;
(d) a light chain variable region CDR1 comprising SEQ ID NO: 27;
(e) a light chain variable region CDR2 comprising SEQ ID NO: 32; and
(f) a light chain variable region CDR3 comprising SEQ ID NO: 37.

Another particular combination comprises:
(a) a heavy chain variable region CDR1 comprising SEQ ID NO: 13;
(b) a heavy chain variable region CDR2 comprising SEQ ID NO: 18;
(c) a heavy chain variable region CDR3 comprising SEQ ID NO: 23;
(d) a light chain variable region CDR1 comprising SEQ ID NO: 28;
(e) a light chain variable region CDR2 comprising SEQ ID NO: 33; and
(f) a light chain variable region CDR3 comprising SEQ ID NO: 38.

Another particular combination comprises:
(a) a heavy chain variable region CDR1 comprising SEQ ID NO: 14;
(b) a heavy chain variable region CDR2 comprising SEQ ID NO: 19;
(c) a heavy chain variable region CDR3 comprising SEQ ID NO: 24;
(d) a light chain variable region CDR1 comprising SEQ ID NO: 29;
(e) a light chain variable region CDR2 comprising SEQ ID NO: 34; and
(f) a light chain variable region CDR3 comprising SEQ ID NO: 39.

Another particular combination comprises:
(a) a heavy chain variable region CDR1 comprising SEQ ID NO: 15;
(b) a heavy chain variable region CDR2 comprising SEQ ID NO: 20;
(c) a heavy chain variable region CDR3 comprising SEQ ID NO: 25;
(d) a light chain variable region CDR1 comprising SEQ ID NO: 30;
(e) a light chain variable region CDR2 comprising SEQ ID NO: 35; and
(f) a light chain variable region CDR3 comprising SEQ ID NO: 40.

Other particular antibodies of this disclosure or antigen binding portions thereof comprise:
(a) a heavy chain variable region comprising the amino acid sequence of SEQ ID NO: 1; and
(b) a light chain variable region comprising the amino acid sequence of SEQ ID NO: 6.

Another particular combination comprises:
(a) a heavy chain variable region comprising the amino acid sequence of SEQ ID NO: 2; and
(b) a light chain variable region comprising the amino acid sequence of SEQ ID NO: 7.

Another particular combination comprises:
(a) a heavy chain variable region comprising the amino acid sequence of SEQ ID NO: 3; and
(b) a light chain variable region comprising the amino acid sequence of SEQ ID NO: 8.

Another particular combination comprises:
(a) a heavy chain variable region comprising the amino acid sequence of SEQ ID NO: 4; and
(b) a light chain variable region comprising the amino acid sequence of SEQ ID NO: 9.

Another particular combination comprises:
(a) a heavy chain variable region comprising the amino acid sequence of SEQ ID NO: 5; and
(b) a light chain variable region comprising the amino acid sequence of SEQ ID NO: 10.

In another aspect of this disclosure, antibodies or antigen-binding portions thereof, are provided that compete for binding to O8E with any of the aforementioned antibodies.

The antibodies of this disclosure can be, for example, full-length antibodies, for example of an IgG1, IgG2 or IgG4 isotype. Alternatively, the antibodies can be antibody fragments, such as Fab, Fab' or Fab'$_2$ fragments or single chain antibodies (e.g., scFv).

This disclosure also provides an immunoconjugate comprising an antibody of this disclosure or antigen-binding portion thereof, linked to a therapeutic agent, such as a cytotoxin or a radioactive isotope. This disclosure also provides a bispecific molecule comprising an antibody or antigen-binding portion thereof, of this disclosure, linked to a second functional moiety having a different binding specificity than said antibody or antigen binding portion thereof.

Compositions comprising an antibody or antigen-binding portion thereof or immunoconjugate or bispecific molecule of this disclosure and a pharmaceutically acceptable carrier are also provided.

Nucleic acid molecules encoding the antibodies or antigen-binding portions thereof, of this disclosure are also encompassed by this disclosure, as well as expression vectors comprising such nucleic acids, host cells comprising such expression vectors and methods for making anti-O8E antibodies using such host cells. Moreover, this disclosure provides a transgenic mouse comprising human immunoglobulin heavy and light chain transgenes, wherein the mouse expresses an antibody of this disclosure, as well as hybridomas prepared from such a mouse, wherein the hybridoma produces the antibody of this disclosure.

In yet another aspect, this disclosure provides a method of treating or preventing a disease characterized by growth of tumor cells expressing O8E, comprising administering to a subject an anti-O8E human antibody of the present disclosure in an amount effective to treat or prevent the disease. The disease can be a cancer, e.g., breast cell carcinoma cancer.

In yet another aspect, this disclosure provides a method of treating an autoimmune disorder, comprising administering to a subject an anti-O8E human antibody of the present disclosure in an amount effective to treat the autoimmune disorder.

Other features and advantages of the instant disclosure will be apparent from the following detailed description and examples which should not be construed as limiting. The contents of all references, Genbauk entries, patents and published patent applications cited throughout this application are expressly incorporated herein by reference.

BRIEF DESCRIPTION OF THE FIGURES AND SEQUENCE IDENTIFIERS

FIG. 1A shows the nucleotide sequence (SEQ ID NO: 41) and amino acid sequence (SEQ ID NO: 1) of the heavy chain variable region of the 1G11 human monoclonal antibody. The CDR1 (SEQ ID NO: 11), CDR2 (SEQ ID NO: 16) and CDR3 (SEQ ID NO: 21) regions are delineated and the V and J germline derivations are indicated.

FIG. 1B shows the nucleotide sequence (SEQ ID NO: 46) and amino acid sequence (SEQ ID NO: 6) of the light chain variable region of the 1G11 human monoclonal antibody. The CDR1 (SEQ ID NO: 26), CDR2 (SEQ ID NO: 31) and CDR3 (SEQ ID NO: 36) regions are delineated and the V and J germline derivations are indicated.

FIG. 2A shows the nucleotide sequence (SEQ ID NO: 42) and amino acid sequence (SEQ ID NO: 2) of the heavy chain variable region of the 2A7 human monoclonal antibody. The CDR1 (SEQ ID NO: 12), CDR2 (SEQ ID NO: 17) and CDR3 (SEQ ID NO: 22) regions are delineated and the V, D, and J germline derivations are indicated.

FIG. 2B shows the nucleotide sequence (SEQ ID NO: 47) and amino acid sequence (SEQ ID NO: 7) of the light chain variable region of the 2A7 human monoclonal antibody. The CDR1 (SEQ ID NO: 27), CDR2 (SEQ ID NO: 32) and CDR3 (SEQ ID NO: 37) regions are delineated and the V and J germline derivations are indicated.

FIG. 3A shows the nucleotide sequence (SEQ ID NO: 43) and amino acid sequence (SEQ ID NO: 3) of the heavy chain variable region of the 2F9 human monoclonal antibody. The CDR1 (SEQ ID NO: 13), CDR2 (SEQ ID NO: 18) and CDR3 (SEQ ID NO: 23) regions are delineated and the V, D and J germline derivations are indicated.

FIG. 3B shows the nucleotide sequence (SEQ ID NO: 48) and amino acid sequence (SEQ ID NO: 8) of the light chain variable region of the 2F9 human monoclonal antibody. The CDR1 (SEQ ID NO: 28), CDR2 (SEQ ID NO: 33) and CDR3 (SEQ ID NO: 38) regions are delineated and the V and J germline derivations are indicated.

FIG. 4A shows the nucleotide sequence (SEQ ID NO: 44) and amino acid sequence (SEQ ID NO: 4) of the heavy chain variable region of the 12E1 human monoclonal antibody. The CDR1 (SEQ ID NO: 14), CDR2 (SEQ ID NO: 19) and CDR3 (SEQ ID NO: 24) regions are delineated and the V, D and J germline derivations are indicated.

FIG. 4B shows the nucleotide sequence (SEQ ID NO: 49) and amino acid sequence (SEQ ID NO: 9) of the light chain variable region of the 12E1 human monoclonal antibody. The CDR1 (SEQ ID NO: 29), CDR2 (SEQ ID NO: 34) and CDR3 (SEQ ID NO: 39) regions are delineated and the V and J germline derivations are indicated.

FIG. 5A shows the nucleotide sequence (SEQ ID NO: 45) and amino acid sequence (SEQ ID NO: 5) of the heavy chain variable region of the 13D12 human monoclonal antibody. The CDR1 (SEQ ID NO: 15), CDR2 (SEQ ID NO: 20) and CDR3 (SEQ ID NO: 25) regions are delineated and the V, D and J germline derivations are indicated.

FIG. 5B shows the nucleotide sequence (SEQ ID NO: 50) and amino acid sequence (SEQ ID NO: 10) of the light chain variable region of the 13D12 human monoclonal antibody. The CDR1 (SEQ ID NO: 30), CDR2 (SEQ ID NO: 35) and CDR3 (SEQ ID NO: 40) regions are delineated and the V and J germline derivations are indicated.

FIG. 6 shows the alignment of the amino acid sequence of the heavy chain variable region of 1G11 and 13D12 with the human germline $V_H$ 4-34 amino acid sequence (SEQ ID NO: 51).

FIG. 7 shows the alignment of the amino acid sequence of the heavy chain variable region of 2A7 and 2F9 with the human germline $V_H$ 3-53 amino acid sequence (SEQ ID NO: 52).

FIG. 8 shows the alignment of the amino acid sequence of the heavy chain variable region of 12E1 with the combined human germline $V_H$ 3-9/D3-10/JH6b amino acid sequence (SEQ ID NO:53).

FIG. 9 shows the alignment of the amino acid sequence of the light chain variable region of 1G11, 2A7, 2F9 and 13D12 with the human germline $V_k$ A27 amino acid sequence (SEQ ID NO:54).

FIG. 10 shows the alignment of the amino acid sequence of the light chain variable region of 12E1 with the combined human germline $V_k$ L6/JK1 amino acid sequence (SEQ ID NO:55).

Figure 11A:
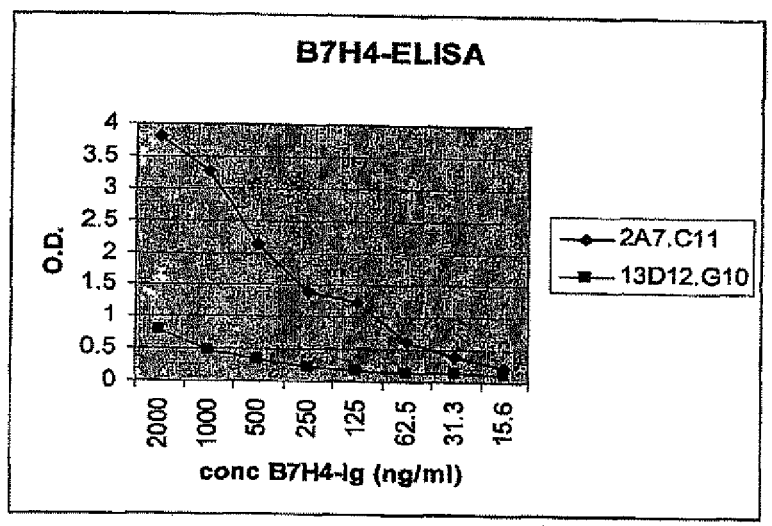
Figure 11B:
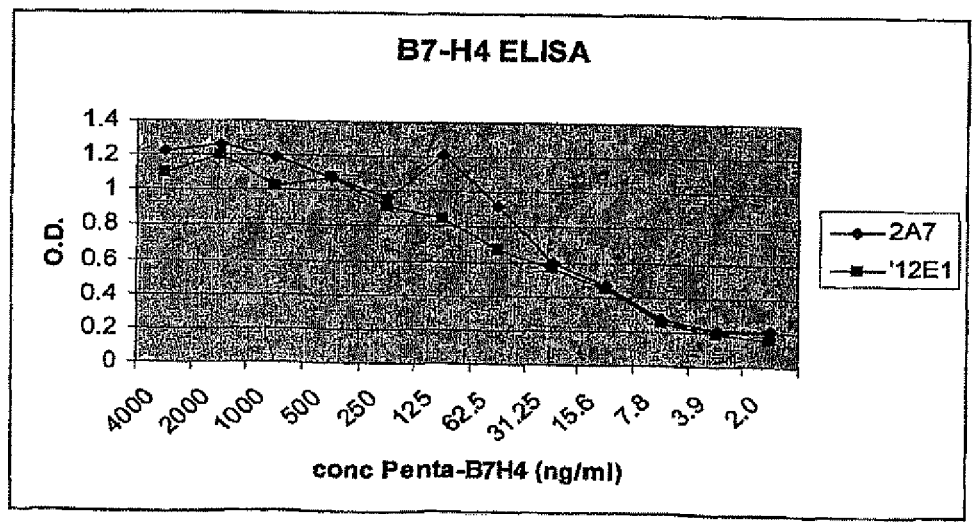

FIGS. 11A and 11B show the results of ELISA experiments demonstrating that human monoclonal antibodies against human O8E specifically bind to O8E. FIG. 11A shows results from an ELISA plate coated with human anti-O8E antibodies followed by the addition of purified O8E protein and detection with rabbit anti-O8E antisera. FIG. 11B shows results from an ELISA plate coated with anti-mouse Fc followed by monoclonal anti-C9 (0.6 µg/ml), then titrated with Penta-O8E protein as indicated and followed by human anti-O8E antibodies at 1 µg/ml.

Figure 12:
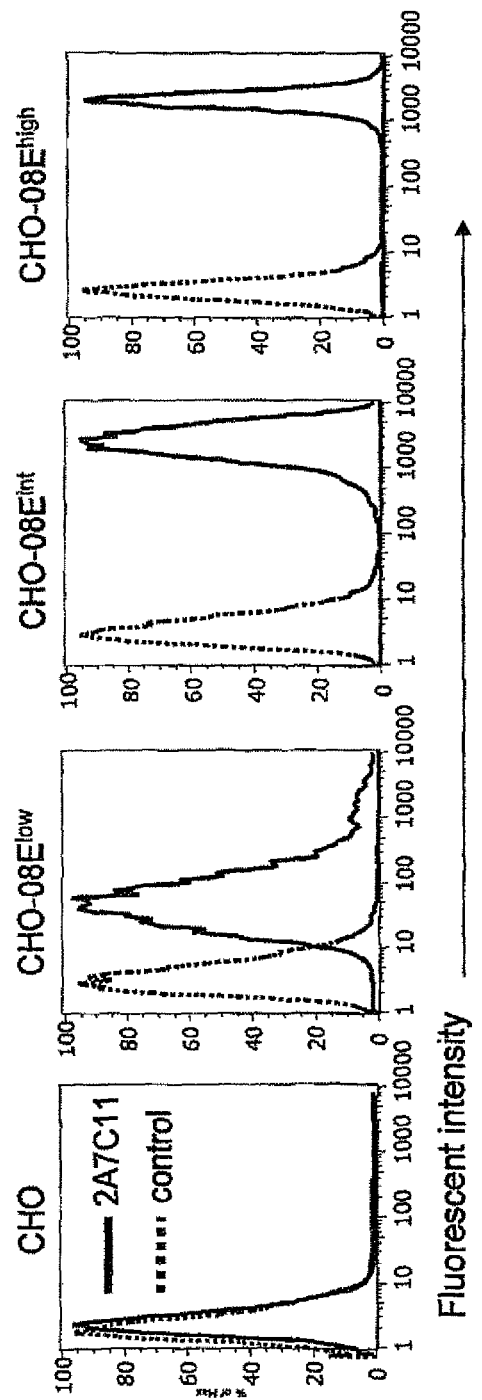

FIG. 12 shows the results of flow cytometry experiments demonstrating that the anti-O8E human monoclonal antibody 2A7 binds to O8E transfected CHO cells.

Figure 13:
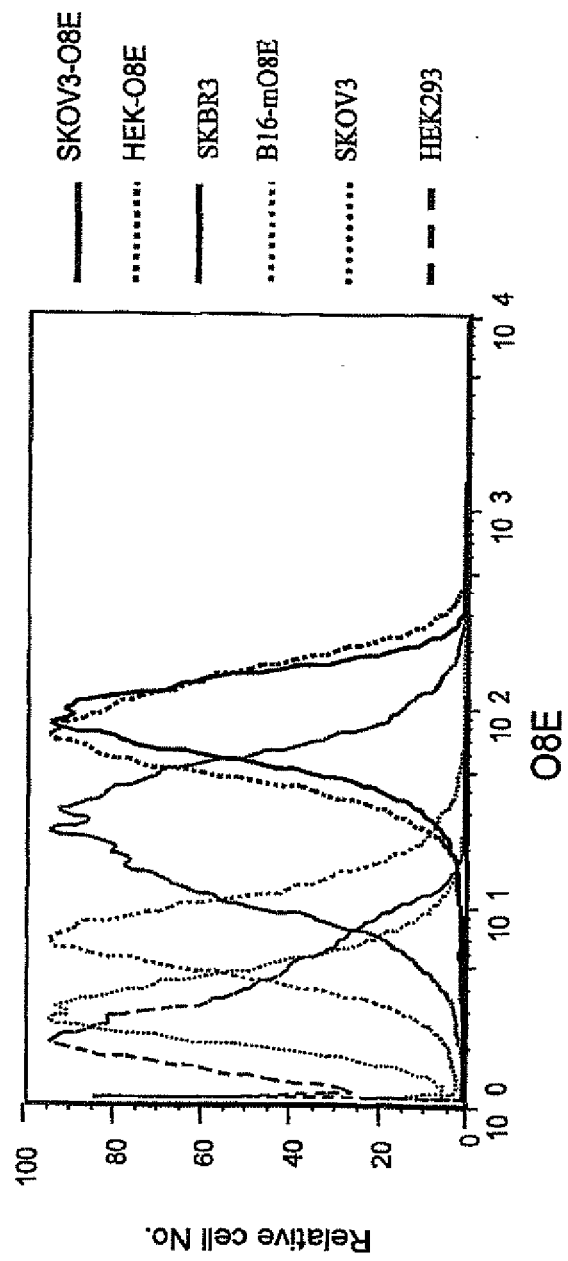

FIG. 13 shows the results of flow cytometry experiments demonstrating expression of O8E in SKBR3 breast carcinoma cells as well as O8E transfected SKOV3 and HEK cells.

Figure 14:
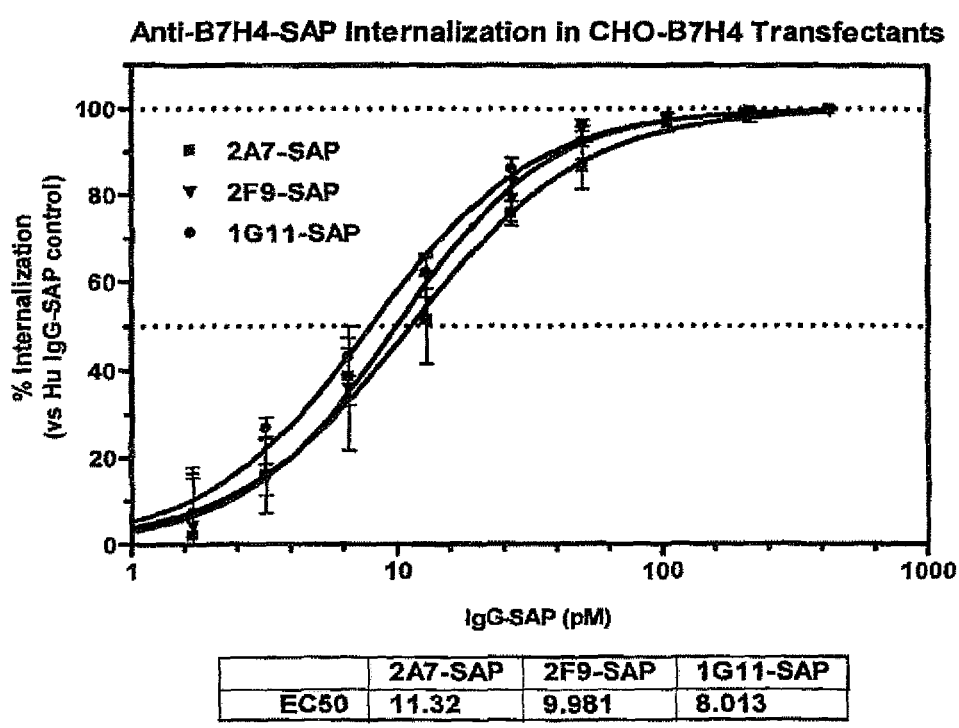

FIG. 14 shows the results of Hum-Zap internalization experiments demonstrating that human monoclonal antibodies against human O8E can internalize into O8E$^+$ CHO cells.

Figure 15:
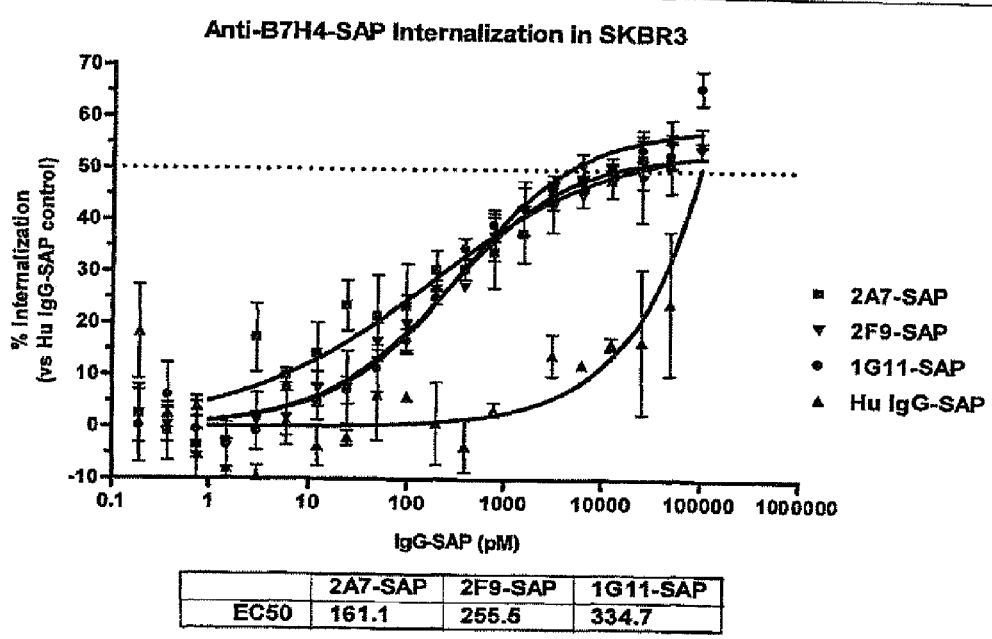

FIG. 15 shows the results of Hum-Zap internalization experiments demonstrating that human monoclonal antibodies against human O8E can internalize into O8E$^+$ SKBR3 cells.

Figure 16:
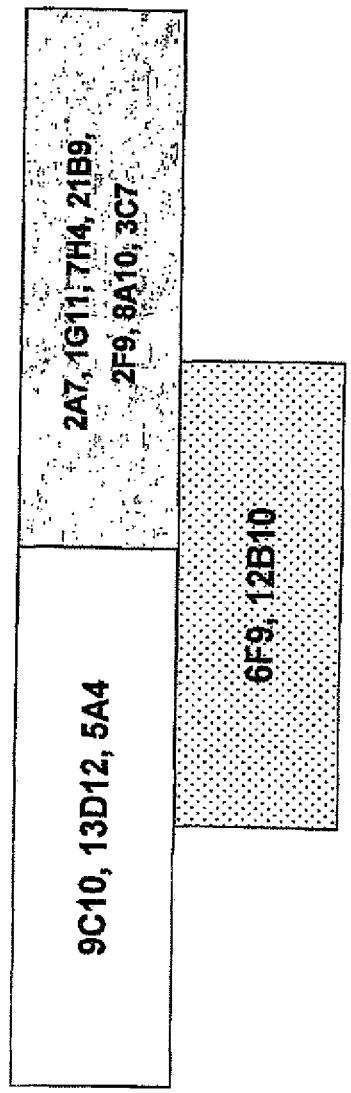

FIG. 16 shows the results of epitope mapping studies with various human anti-O8E monoclonal antibodies including 1G11, 2A7, 2F9 and 13D12.

Figure 17:
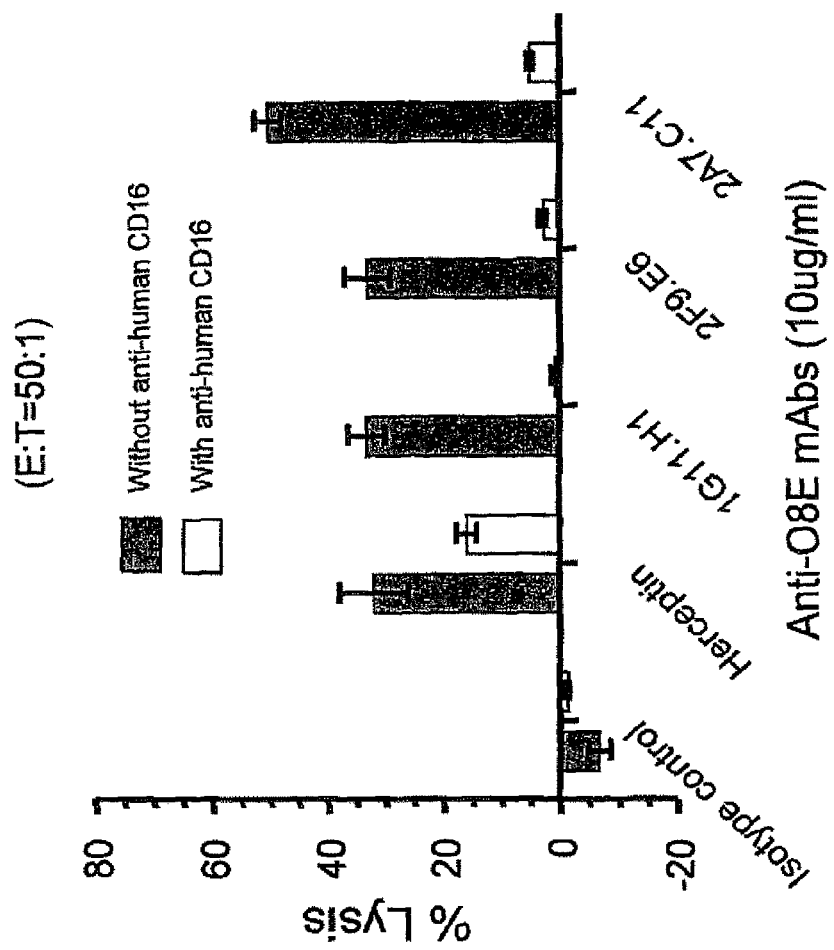

FIG. 17 shows the results of antibody dependent cellular cytotoxicity (ADCC) assays demonstrating that human monoclonal anti-O8E antibodies kill human breast cancer cell line SKBR3 in an ADCC dependent manner.

Figure 18:
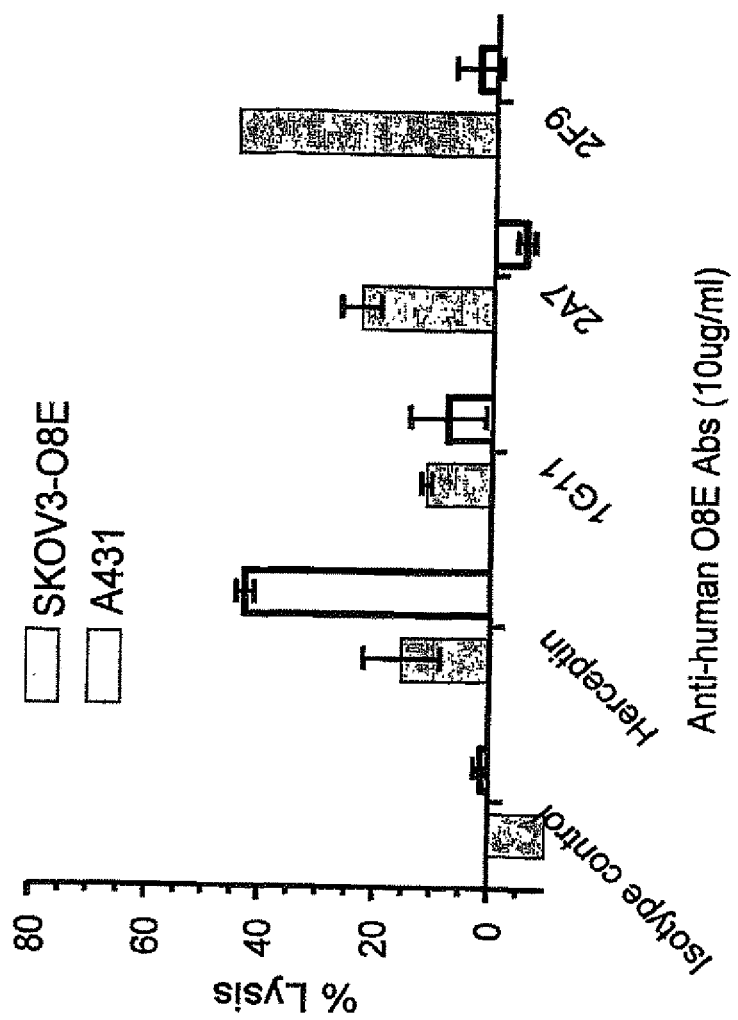

FIG. 18 shows the results of antibody dependent cellular cytotoxicity (ADCC) assays demonstrating that human monoclonal anti-O8E antibodies kill O8E transfected SKOV3 cells in an ADCC dependent manner.

Figure 19:
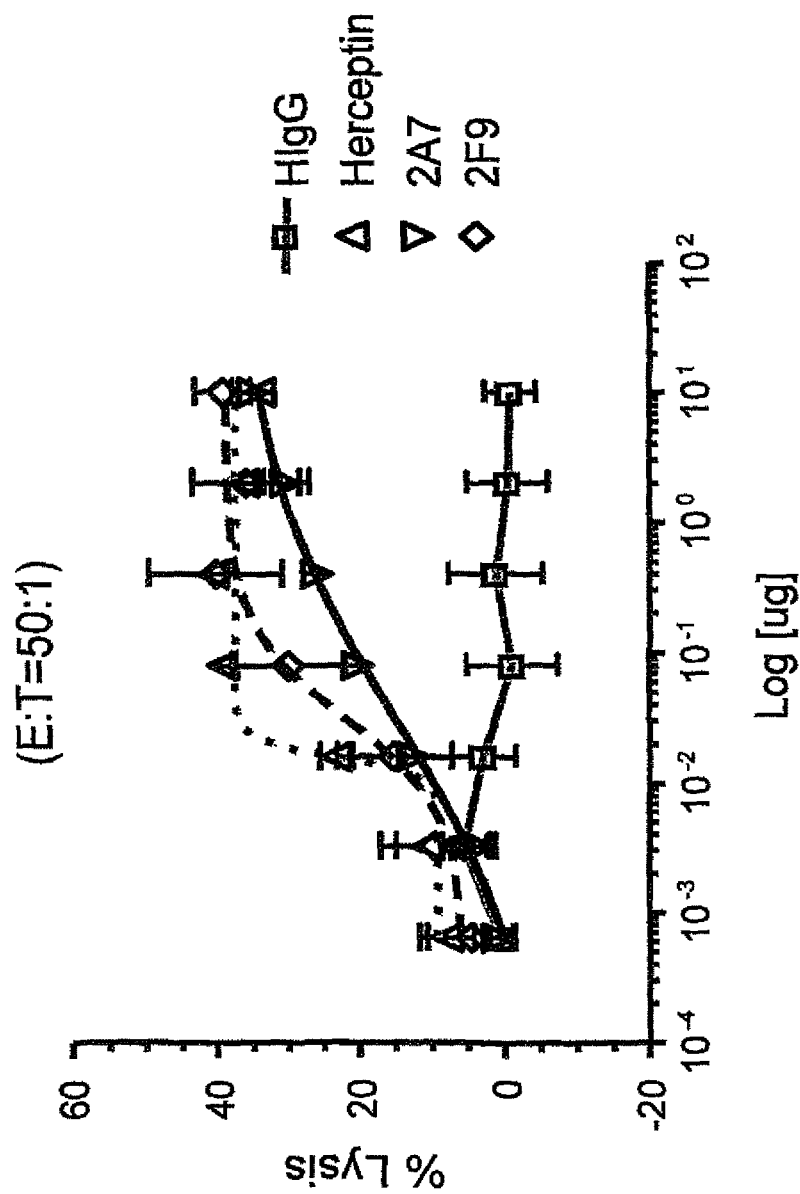

FIG. 19 shows the results of antibody dependent cellular cytotoxicity (ADCC) assays demonstrating that human monoclonal anti-O8E antibodies kill human breast cancer cell line SKBR3 in a concentration and ADCC dependent manner.

Figure 20:
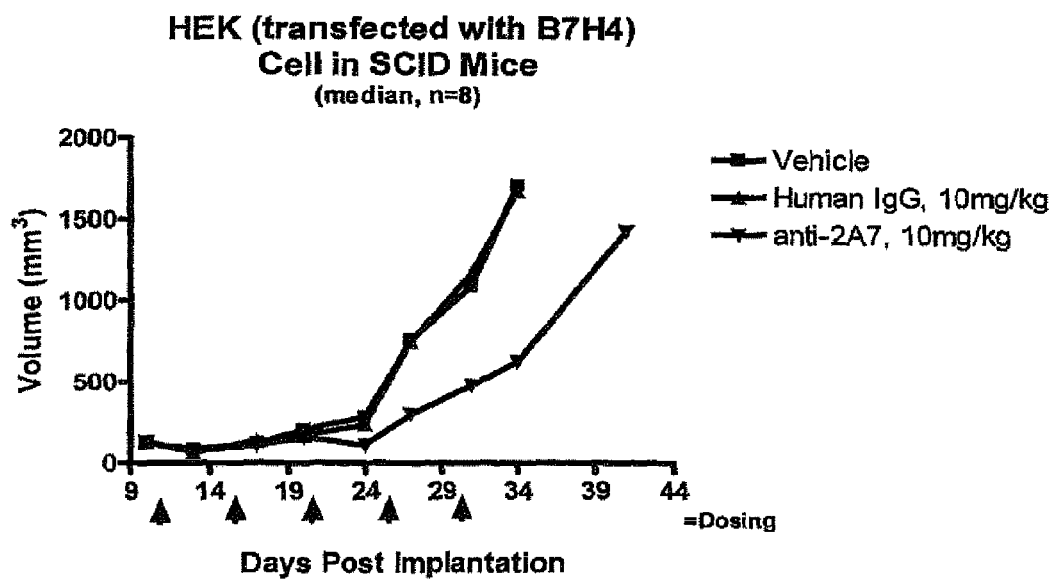

FIG. 20 shows the results of in vivo studies on SCID mice showing tumor growth inhibition of HEK-B7H4 tumors by anti-O8E antibodies.

DETAILED DESCRIPTION

The present disclosure relates to isolated monoclonal antibodies, particularly human sequence monoclonal antibodies, that bind specifically to O8E (a/k/a B7H4, B7S1 and B7x) with high affinity. In certain embodiments, the antibodies of this disclosure are derived from particular heavy and light chain germline sequences and/or comprise particular structural features such as CDR regions comprising particular amino acid sequences. This disclosure provides isolated antibodies, methods of making such antibodies, immunoconjugates and bispecific molecules comprising such antibodies and pharmaceutical compositions containing the antibodies, immunoconjugates or bispecific molecules of this disclosure. This disclosure also relates to methods of using the antibodies, such as to detect O8E, as well as to treat diseases associated with expression of O8E, such as cancer. Accordingly, this disclosure also provides methods of using the anti-O8E antibodies of this disclosure to treat various cancers, for example, in the treatment of breast cell carcinomas, metastatic breast cancers, ovarian cell carcinomas, metastatic ovarian cancers and renal cell carcinomas.

In order that the present disclosure may be more readily understood, certain terms are first defined. Additional definitions are set forth throughout the detailed description.

The terms "O8E," "B7H4," "B7x" and "B7S1" are used herein interchangeably and include variants, isoforms, homologs, orthologs and paralogs of human O8E. For example, antibodies specific for O8E may, in certain cases, cross-react with O8E from species other than human. In other embodiments, the antibodies specific for human O8E may be completely specific for human O8E and may not exhibit species or other types of cross-reactivity. The term "human O8E" refers to human sequence O8E, such as the complete amino acid sequence of human USE having Genbank accession number NP_078902 (SEQ ID NO:56). O8E is also known in the art as, for example, BL-CAM, B3, Leu-14 and Lyb-8. The human O8E sequence may differ from human O8E of SEQ ID NO:56 by having, for example, conserved mutations or mutations in non-conserved regions and the CD22 has substantially the same biological function as the human O8E of SEQ ID NO:56. For example, a biological function of human O8E is having an epitope in the extracellular domain of O8E that is specifically bound by an antibody of the instant disclosure or a biological function of human O8E includes, for example, inhibition of T-cell proliferation, inhibition of cytokine production, inhibition of cell cycle production, or binding to T cell receptors.

A particular human O8E sequence will generally be at least 90% identical in amino acids sequence to human O8E of SEQ ID NO:56 and contains amino acid residues that identify the amino acid sequence as being human when compared to O8E amino acid sequences of other species (e.g., murine). In certain cases, a human O8E may be at least 95%, or even at least 96%, 97%, 98%, or 99% identical in amino acid sequence to O8E of SEQ ID NO:56. In certain embodiments, a human O8E sequence will display no more than 10 amino acid differences from the O8E of SEQ ID NO:56. In certain embodiments, the human O8E may display no more than 5, or even no more than 4, 3, 2, or 1 amino acid difference from the O8E of SEQ ID NO:56. Percent identity can be determined as described herein.

The term "immune response" refers to the action of, for example, lymphocytes, antigen presenting cells, phagocytic cells, granulocytes and soluble macromolecules produced by the above cells or the liver (including antibodies, cytokines and complement) that results in selective damage to, destruction of or elimination from the human body of invading pathogens, cells or tissues infected with pathogens, cancerous cells or, in cases of autoimmunity or pathological inflammation, normal human cells or tissues.

A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell. An example of a "cell surface receptor" of the present disclosure is the O8E receptor.

The term "antibody" as referred to herein includes whole antibodies and any antigen binding fragment (i.e. "antigen-binding portion") or single chains thereof. An "antibody" refers to a glycoprotein comprising at least two heavy (H) chains and two light (L) chains interconnected by disulfide bonds or an antigen binding portion thereof. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody (or "antibody portion"), as used herein, refers to one or more fragments of an antibody that retain the ability to specifically bind to an antigen (e.g., O8E). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fab' fragment, which is essentially an Fab with part of the hinge region (see Fundamental immunology (Paul ed., 3$^{rd}$ ed. 1993); (iv) a Fd fragment consisting of the $V_H$ and $C_{H1}$ domains; (v) a Fv fragment consisting of the $V_L$ and $V_H$ domains of a single arm of an antibody, (vi) a dAb fragment (Ward et al., (1989) *Nature* 341:544-546), which consists of a $V_H$ domain; and (vii) an isolated complementarity determining region (CDR); and (viii) a nanobody, a heavy chain variable region containing a single variable domain and two constant domains. Furthermore, although the two domains of the Fv fragment, $V_L$ and $V_H$, are coded for by separate genes, they can be joined, using recombinant methods, by a synthetic linker that enables them to be made as a single protein chain in which the $V_L$, and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds O8E is substantially free of antibodies that specifically bind antigens other than O8E). An isolated antibody that specifically binds O8E may, however, have cross-reactivity to other antigens, such as O8E molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody" or "human sequence antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies may include later modifications, including natural or synthetic modifications. The human antibodies of this disclosure may include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences.

The term "human monoclonal antibody", which may include the term "sequence" after "human", refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another agent or antibody.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

As used herein, an antibody that "specifically binds to human O8E" is intended to refer to an antibody that binds to human O8E with a $K_D$ of $1\times10^{-7}$ or less, more typically $5\times10^{-8}$ M or less, more typically $3\times10^{-8}$ M or less, more typically $1\times10^{-9}$ M or less, even more typically $5\times10^{-9}$ M or less.

The term "does not substantially bind" to a protein or cells, as used herein, means does not bind or does not bind with a high affinity to the protein or cells, i.e. binds to the protein or cells with a $K_D$ of $1\times10^{-6}$ M or more, more preferably $1\times10^{-5}$ M or more, more preferably $1\times10^{-4}$ M or more, more preferably $1\times10^{-3}$ M or more, even more preferably $1\times10^{-2}$ M or more.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. A preferred method for determining the $K_D$ of an antibody is by using surface plasmon resonance, typically using a biosensor system such as a Biacore® system.

As used herein, the term "high affinity" for an IgG antibody refers to an antibody having a $K_D$ of $1\times10^{-7}$ M or less, more typically $5\times10^{-8}$ M or less, more typically $1\times10^{-9}$ M or less and even more typically $5\times10^{-9}$ M or less for a target antigen. However, "high affinity" binding can vary for other antibody isotypes. For example, "high affinity" binding for an IgM isotype refers to an antibody having a $K_D$ of $10^{-6}$ M or less, more typically $10^{-7}$ M or less, even more typically $10^{-8}$ M or less.

As used herein, the term "subject" includes any human or nonhuman animal. The term "nonhuman animal" includes all vertebrates, e.g., mammals and non-mammals, such as nonhuman primates, sheep, dogs, cats, horses, cows, chickens, amphibians, fish, reptiles, etc.

As used herein, the term "O8E" is used synonymously with the terms "B7H4," "B7S1," and "B7x" as these terms variously appear in the scientific literature. The amino acid sequence of O8E (B7H4) is publicly available by reference to GenBank Accession Nos. AAZ17406, AAS13400, AAP37283, CAI12739 and CAI12737 and by reference to Prasad et al. (2003) Immunity 18:863-873; Sica et al. (2003) Immunity 18:849-861; and U.S. Pat. No. 6,891,030 each of which is incorporated herein by reference in its entirety.

Various aspects of this disclosure are described in further detail in the following subsections.

Anti-O8E Antibodies

The antibodies of this disclosure are characterized by particular functional features or properties of the antibodies. For example, the antibodies bind specifically to human O8E. Typically, an antibody of this disclosure binds to O8E with high affinity, for example with a $K_D$ of $1 \times 10^{-7}$ M or less. The anti-O8E antibodies of this disclosure typically exhibit one or more of the following characteristics:
(a) binds to human O8E with a $K_D$ of $1 \times 10^{-7}$ M or less;
(b) binds to human CHO cells transfected with O8E.

Typically, the antibody binds to human O8E with, a $K_D$ of $5 \times 10^{-8}$ M or less, bind to human O8E with a $K_D$ of $2 \times 10^{-8}$ M or less, binds to human O8E with a $K_D$ of $5 \times 10^{-9}$ M or less, binds to human O8E with a $K_D$ of $4 \times 10^{-9}$ M or less, binds to human O8E with a $K_D$ of $3 \times 10^{-9}$ M or less, binds to human O8E with a $K_D$ of $2 \times 10^{-9}$ M or less or binds to human O8E with a $K_D$ of $1 \times 10^{-9}$ M or less.

Standard assays to evaluate the binding ability of the antibodies toward O8E are known in the art, including for example, ELISAs, Western blots, RIM and flow cytometry analysis. Suitable assays are described in detail in the Examples. The binding kinetics (e.g., binding affinity) of the antibodies also can be assessed by standard assays known in the art, such as by ELISA, Scatchard and Biacore® system analysis. As another example, the antibodies of the present disclosure may bind to a breast carcinoma tumor cell line, for example, the SKBR3 cell line.

Monoclonal Antibodies 1G11, 2A7, 2F9, 12E1 and 13D12

Exemplified antibodies of this disclosure include the human monoclonal antibodies 1G11, 2A7, 2F9, 12E1 and 13D12 isolated and structurally characterized as described in Examples 1 and 2. The $V_H$ amino acid sequences of 1G11, 2A7, 2F9, 12E1 and 13D12 are shown in SEQ ID NOs: 1, 2, 3, 4 and, 5 respectively. The $V_L$ amino acid sequences of 1G11, 2A7, 2F9, 12E1 and 13D12 are shown in SEQ ID NOs: 6, 7, 8, 9 and 10, respectively.

Given that each of these antibodies can bind to O8E, the $V_H$ and $V_L$ sequences can be "mixed and matched" to create other anti-O8E binding molecules of this disclosure. O8E binding of such "mixed and matched" antibodies can be tested using the binding assays described above and in the Examples (e.g., FACS or ELISAs). Typically, when $V_H$ and $V_L$ chains are mixed and matched, a $V_H$ sequence from a particular $V_H/V_L$ pairing is replaced with a structurally similar $V_H$ sequence. Likewise, typically a $V_L$ sequence from a particular $V_H/V_L$ pairing is replaced with a structurally similar $V_L$ sequence.

Accordingly, in one aspect, this disclosure provides an isolated monoclonal antibody or antigen binding portion thereof comprising;
(a) a heavy chain variable region comprising an amino acid sequence selected from the group consisting of SEQ ID NOs: 1, 2, 3, 4 and 5; and
(b) a light chain variable region comprising an amino acid sequence selected from the group consisting of SEQ ID NOs: 6, 7, 8, 9 and 10; wherein the antibody specifically binds to O8E, typically human O8E.

Preferred heavy and light chain combinations include:
(a) a heavy chain variable region comprising the amino acid sequence of SEQ ID NO: 1; and (b) a light chain variable region comprising the amino acid sequence of SEQ ID NO: 6; or
(b) a heavy chain variable region comprising the amino acid sequence of SEQ ID NO: 2; and (b) a light chain variable region comprising the amino acid sequence of SEQ ID NO: 7; or
(c) a heavy chain variable region comprising the amino acid sequence of SEQ ID NO: 3; and (b) a light chain variable region comprising the amino acid sequence of SEQ ID NO: 8;
(d) a heavy chain variable region comprising the amino acid sequence of SEQ ID NO: 4; and (b) a light chain variable region comprising the amino acid sequence of SEQ ID NO: 9; or
(e) a heavy chain variable region comprising the amino acid sequence of SEQ ID NO: 5; and (b) a light chain variable region comprising the amino acid sequence of SEQ ID NO: 10.

In another aspect, this disclosure provides antibodies that comprise the heavy chain and light chain CDR1s, CDR2s and CDR3s of 1G11, 2A7, 2F9, 12E1 and 13D12 or combinations thereof. The amino acid sequences of the $V_H$ CDR1s of 1G11, 2A7, 2F9, 12E1 and 13D12 are shown in SEQ ID NOs: 11, 12, 13, 14 and 15, respectively. The amino acid sequences of the $V_H$ CDR2s of 1G11, 2A7, 2F9, 12E1 and 13D12 are shown in SEQ ID NOs: 16, 17, 18, 19 and 20, respectively. The amino acid sequences of the $V_H$ CDR3s of 1G11, 2A7, 2F9, 12E1 and 13D12 are shown in SEQ ID NOs: 21, 22, 23, 24 and 25, respectively. The amino acid sequences of the $V_k$ CDR1s of 1G11, 2A7, 2F9, 12E1 and 13D12 are shown in SEQ ID NOs: 26, 27, 28, 29 and 30, respectively. The amino acid sequences of the $V_k$ CDR2s of 1G11, 2A7, 2F9, 12E1 and 13D12 are shown in SEQ ID NOs: 31, 32, 33, 34 and 35, respectively. The amino acid sequences of the $V_k$ CDR3s of 1G11, 2A7, 2F9, 12E1 and 13D12 are shown in SEQ ID NOs: 36, 37, 38, 39 and 40, respectively. The CDR regions are delineated using the Kabat system (Kabat, E. A., et al. (1991) Sequences of Proteins of Immunological Interest, Fifth Edition, U.S. Department of Health and Human Services, NIH Publication No. 91-3242).

Each of the above referenced amino acid and nucleotide sequences of the human antibodies designated herein as 1G11, 2A7, 2F9, 12E1 and 13D12 are presented in the following Table 1 and Sequence Listing.

TABLE 1

Sequences of Heavy and Light Chain Variable and Constant Regions and Corresponding CDRs of Human Antibodies 1G11, 2A7, 2F9, 12E1 and 13D12

| Sequence Identifier | Description | Sequence |
|---|---|---|
| SEQ ID NO: 1 | Amino acid sequence of the heavy chain variable region of the 1G11 human monoclonal antibody | QVQLQQWGAGLLKPSETLSLTCAVYGGSFSDYFWTWIRQP PGKGLEWIGEINHSGTTNYNPSLKSRVTISADTSKNQFSR LSSVTAADTAVYYCARLSSWSNWAFEYWGQGTLVTVSS |

TABLE 1-continued

Sequences of Heavy and Light Chain Variable and Constant Regions and
Corresponding CDRs of Human Antibodies 1G11, 2A7, 2F9, 12E1 and 13D12

| Sequence Identifier | Description | Sequence |
|---|---|---|
| SEQ ID NO: 2 | Amino acid sequence of the heavy chain variable region of the 2A7 human monoclonal antibody | EVQLVESGGGLIQPGGSLRLSCAASGFTVSSNYMNWVRQA PGKGLEWVSVIYGSGRTYYADSVKGRVTISRDNSKNTLYL QMNSLRAEDTAVYYCARDTYAMDVWGQGTTVTVSS |
| SEQ ID NO: 3 | Amino acid sequence of the heavy chain variable region of the 2F9 human monoclonal antibody | EVQLVESGGGLIQPGGSLRLSCAASGFIVSRNYMNWVRQA PGKGLEWVSVIYGSGRTDCADSVKGRFTISRDNSKNTLYL OMNSLRAEDTAVYYCARDGDYGMDVWGQGTTVTVSS |
| SEQ ID NO: 4 | Amino acid sequence of the heavy chain variable region of the 12E1 human monoclonal antibody | EVQLVESGGGLVQPGGSLRLSCVASGFTFDDYAMHWVRQA PGKGLEWVSGISWNSGSIGYADSVKGRFTISRDNAKNSLY LQMNSLRAEDTALYYCTKALYGSGSSDFYYYGMDVWGQGT TVAVSS |
| SEQ ID NO: 5 | Amino acid sequence of the heavy chain variable region of the 13D12 human monoclonal antibody | QVQLQQWGAGLLKPSETLSLTCAVYGGSFSGYYWSWIRQP PGKGLEWIGKINHSGSTMYNPSLKSKVTISVDTSKNQFSL KLNSVTAADTAVYYCARELRYFENYYYGMDVWGQGTTVTV SS |
| SEQ ID NO: 6 | Amino acid sequence of the light chain variable region of the 1G11 human monoclonal antibody | EIVLTQFPGTLSLSPGERATLSCRASQSVSSTYLAWYQQK PGQAPRVLIYGASRRATGIPDRFSGSGSGTDFTLTISRLE PEDFAVYYCQQYGSSPLTFGGGTKLEIK |
| SEQ ID NO: 7 | Amino acid sequence of the light chain variable region of the 2A7 human monoclonal antibody | EIVLTQSPGTLSLSPGERATLSCRASQSVSSSYLAWYQQK PGQAPRLLIYGASSRATGIPDRFSGSGSGTDFTLTISRLE PEDFAVYYCQQYGSSPLYTFGQGTKLEIK| |
| SEQ ID NO: 8 | Amino acid sequence of the light chain variable region of the 2F9 human monoclonal antibody | EIVLTQSPGTLSLSPGERATLSCRASQSVSSSYLAWYQQK PGQAPRLLIYGASSRATGIPDRFSGSGSGTDFTLTISRLE PEDFAVYYCQQYGSSPLYTFGQGTKLEIK |
| SEQ ID NO: 9 | Amino acid sequence of the light chain variable region of the 12E1 human monoclonal antibody | EIVLTQSPATLSLSPGERATLSCRASQSVSSSYLAWYQQKP GQAPRLLIYDASNRATGIPARFSGSGSGTDFTLTISSLEP EDFAVYYCQQRRTFGQGTKVEIK |
| SEQ ID NO: 10 | Amino acid sequence of the light chain variable region of the 13D12 human monoclonal antibody | EIVLTQSPGTLSLSPGERATLSCRASQSVSSSYLAWYQQK PGQAPRLLIYGASSRATGIPDRFSGSGSGTDFTLTISRLE PEDFAVYYCQQYGSSPRTFGQGTKVEIK |
| SEQ ID NO: 11 | Amino acid sequence of the heavy chain variable region CDR1 of the 1G11 human monoclonal antibody | DYFWT |
| SEQ ID NO: 12 | Amino acid sequence of the heavy chain variable region CDR1 of the 2A7 human monoclonal antibody | SNYMNW |
| SEQ ID NO: 13 | Amino acid sequence of the heavy chain variable region CDR1 of the 2F9 human monoclonal antibody | RNYMN |
| SEQ ID NO: 14 | Amino acid sequence of the heavy chain variable region CDR1 of the 12E1 human monoclonal antibody | DYAMH |
| SEQ ID NO: 15 | Amino acid sequence of the heavy chain variable | GYYWS |

TABLE 1-continued

Sequences of Heavy and Light Chain Variable and Constant Regions and Corresponding CDRs of Human Antibodies 1G11, 2A7, 2F9, 12E1 and 13D12

| Sequence Identifier | Description | Sequence |
|---|---|---|
| | region CDR1 of the 13D12 human monoclonal antibody | |
| SEQ ID NO: 16 | Amino acid sequence of the heavy chain variable region CDR2 of the 1G11 human monoclonal antibody | EINHSGTTNYNPSLKS |
| SEQ ID NO: 17 | Amino acid sequence of the heavy chain variable region CDR2 of the 2A7 human monoclonal antibody | VIYGSGRTYYADSVKG |
| SEQ ID NO: 18 | Amino acid sequence of the heavy chain variable region CDR2 of the 2F9 human monoclonal antibody | VIYGSGRTDCADSVKG |
| SEQ ID NO: 19 | Amino acid sequence of the heavy chain variable region CDR2 of the 12E1 human monoclonal antibody | GISWNSGSIGYADSVKG |
| SEQ ID NO: 20 | Amino acid sequence of the heavy chain variable region CDR2 of the 13D12 human monoclonal antibody | KINHSGSTNYNPSLKS |
| SEQ ID NO: 21 | Amino acid sequence of the heavy chain variable region CDR3 of the 1G11 human monoclonal antibody | LSSWSNWAFEY |
| SEQ ID NO: 22 | Amino acid sequence of the heavy chain variable region CDR3 of the 2A7 human monoclonal antibody | DTYAMDV |
| SEQ ID NO: 23 | Amino acid sequence of the heavy chain variable region CDR3 of the 2F9 human monoclonal antibody | DGDYGMDV |
| SEQ ID NO: 24 | Amino acid sequence of the heavy chain variable region CDR3 of the 12E1 human monoclonal antibody | LYGSGSSDFYYYGMDV |
| SEQ ID NO: 25 | Amino acid sequence of the heavy chain variable region CDR3 of the 13D12 human monoclonal antibody | ELRYFENYYYGMDV |
| SEQ ID NO: 26 | Amino acid sequence of the light chain variable region CDR1 of the 1G11 human monoclonal antibody | RASQSVSSTYLA |

TABLE 1-continued

Sequences of Heavy and Light Chain Variable and Constant Regions and
Corresponding CDRs of Human Antibodies 1G11, 2A7, 2F9, 12E1 and 13D12

| Sequence Identifier | Description | Sequence |
|---|---|---|
| SEQ ID NO: 27 | Amino acid sequence of the light chain variable region CDR1 of the 2A7 human monoclonal antibody | RASQSVSSSYLA |
| SEQ ID NO: 28 | Amino acid sequence of the light chain variable region CDR1 of the 2F9 human monoclonal antibody | RASQSVSSSYLA |
| SEQ ID NO: 29 | Amino acid sequence of the light chain variable region CDR1 of the 12E1 human monoclonal antibody | RASQSVSSSYLA |
| SEQ ID NO: 30 | Amino acid sequence of the light chain variable region CDR1 of the 13D12 human monoclonal antibody | RASQSVSSSYLA |
| SEQ ID NO: 31 | Amino acid sequence of the light chain variable region CDR2 of the 1G11 human monoclonal antibody | GASRRAT |
| SEQ ID NO: 32 | Amino acid sequence of the light chain variable region CDR2 of the 2A7 human monoclonal antibody | GASSRAT |
| SEQ ID NO: 33 | Amino acid sequence of the light chain variable region CDR2 of the 2F9 human monoclonal antibody | GASSRAT |
| SEQ ID NO: 34 | Amino acid sequence of the light chain variable region CDR2 of the 12E1 human monoclonal antibody | DASNRAT |
| SEQ ID NO: 35 | Amino acid sequence of the light chain variable region CDR2 of the 13D12 human monoclonal antibody | GASSRAT |
| SEQ ID NO: 36 | Amino acid sequence of the light chain variable region CDR3 of the 1G11 human monoclonal antibody | QQYGSSPLT |
| SEQ ID NO: 37 | Amino acid sequence of the light chain variable region CDR3 of the 2A7 human monoclonal antibody | QQYGSSPMYT |
| SEQ ID NO: 38 | Amino acid sequence of the light chain variable region CDR3 of the 2F9 human monoclonal antibody | QQYGSSPLYT |

TABLE 1-continued

Sequences of Heavy and Light Chain Variable and Constant Regions and
Corresponding CDRs of Human Antibodies 1G11, 2A7, 2F9, 12E1 and 13D12

| Sequence Identifier | Description | Sequence |
|---|---|---|
| SEQ ID NO: 39 | Amino acid sequence of the light chain variable region CDR3 of the 12E1 human monoclonal antibody | QQRRT |
| SEQ ID NO: 40 | Amino acid sequence of the light chain variable region CDR3 of the 13D12 human monoclonal antibody | QQYGSSPRT |
| SEQ ID NO: 41 | Nucleotide sequence of the heavy chain variable region of the 1G11 human monoclonal antibody | CAGGTGCAGCTACAGCAGTGGGGCGCAGGACTGTTGAAGC CTTCGGAGACCCTGTCCCTCACCTGCGCTGTCTATGGTGG GTCCTTCAGTGATTACTTCTGGACCTGGATCCGCCAGCCC CCAGGGAAGGGCCTGGAGTGGATTGGGGAAATCAATCATA GTGGAACCACCAACTACAACCCGTCCCTCAAGAGTCGAGT CACCATTTCAGCAGACACGTCCAAGAACCAGTTCTCCCTG AGGCTGAGCTCTGTGACCGCCGCGGACACGGCTGTGTATT ACTGTGCGAGACTCAGCAGCTGGTCGAACTGGGCCTTTGA GTACTGGGGCCAGGGAACCCTGGTCACCGTCTCCTCA |
| SEQ ID NO: 42 | Nucleotide sequence of the heavy chain variable region of the 2A7 human monoclonal antibody | GAGGTGCAGCTGGTGGAGTCTGGAGGAGGCTTGATCCAGC CTGGGGGGTCCCTGAGACTCTCCTGTGCAGCCTCTGGGTT CACCGTCAGTAGCAACTACATGAACTGGGTCCGCCAGGCT CCAGGGAAGGGGCTGGAGTGGGTCTCAGTTATTTATGGCA GTGGTAGAACATATTACGCAGACTCCGTGAAGGGCCGAGT CACCATCTCCAGAGACAATTCCAAGAACACGCTGTATCTT CAAATGAACAGCCTGAGAGCCGAGGACACGGCCGTGTATT ACTGTGCGAGAGATACCTACGCTATGGACGTCTGGGGCCA AGGGACCACGGTCACCGTCTCCTCT |
| SEQ ID NO: 43 | Nucleotide sequence of the heavy chain variable region of the 2F9 human monoclonal antibody | GAGGTGCAGTTGGTGGAGTCTGGAGGAGGCTTGATCCAGC CTGGGGGGTCCCTGAGACTCTCCTGTGCAGCCTCTGGGTT CATCGTCAGTAGAAACTACATGAACTGGGTCCGCCAGGCT CCAGGGAAGGGGCTGGAGTGGGTCTCAGTTATTTATGGCA GTGGTAGGACAGACTGCGGAGACTCCGTGAAGGGCCGATT CACCATCTCCAGAGACAATTCCAAGAACACGCTGTATCTT CAAATGAACAGCCTGAGAGCCGAGGACACGGCCGTGTATT ACTGTGCGAGAGATGGGGACTACGGTATGGACGTCTGGGG CCAAGGGACCACGGTCACCGTCTCCTA |
| SEQ ID NO: 44 | Nucleotide sequence of the heavy chain variable region of the 12E1 human monoclonal antibody | GAAGTGCAGCTGGTGGAGTCTGGGGGAGGCTTGGTACAGC CTGGCAGGTCCCTGAGACTCTCCTGTGTAGCCTCTGGATT CACCTTTGATGATTATGCCATGCACTGGGTCCGGCAAGCT CCAGGGAAGGGCCTGGAGTGGGTCTCAGGTATTAGTTGGA ATAGTGGTAGCATAGGCTATGCGGACTCTGTGAAGGGCCG ATTCACCATCTCCAGAGACAACGCCAAGAACTCCCTGTAT CTGCAAATGAACAGTCTGAGAGCTGAGGACACGGCCTTGT ATTACTGTACAAAAGCCCTCTATGGTTCGGGGAGTTCTGA CTTCTACTACTACGGTATGGACGTCTGGGGCCAAGGGACC ACGGTCGCCGTCTCCTCA |
| SEQ ID NO: 45 | Nucleotide sequence of the heavy chain variable region of the 13D12 human monoclonal antibody | CAGGTGCAGCTACAGCAGTGGGGCGCAGGACTGTTGAAGC CTTCGGAGACCCTGTCCCTCACCTGCGCTGTCTATGGTGG GTCCTTCAGTGGTTACTACTGGAGCTGGATCCGCCAGCCC CCAGGGAAGGGGCTGGAGTGGATTGGGAAAATCAATCATA GCGGAAGTACCAACTACAACCCGTCCCTCAAGAGTCGAGT CACCATATCAGTAGACACGTCCAAGAACCAGTTCTCCCTG AAACTAAACTCTGTGACCGCCGCGGACACGGCTGTGTATT ACTGTGCGAGAGAATTACGATATTTTGAAAACTACTACTA CGGTATGGACGTCTGGGGCCAAGGGACCACGGTCACCGTC TCCTCA |

TABLE 1-continued

Sequences of Heavy and Light Chain Variable and Constant Regions and Corresponding CDRs of Human Antibodies 1G11, 2A7, 2F9, 12E1 and 13D12

| Sequence Identifier | Description | Sequence |
|---|---|---|
| SEQ ID NO: 46 | Nucleotide sequence of the light chain variable region of the 1G11 human monoclonal antibody | GAAATTGTGTTGACGCAGTTTCCAGGCACCCTGTCTTTGT CTCCAGGGGAAAGAGCCACCCTCTCCTGCAGGGCCAGTCA GAGTGTTAGCAGCACCTACTTAGCCTGGTACCAGCAGAAA CCTGGCCAGGCTCCCAGGGTCCTCATCTATGGTGCATCCA GAAGGGCCACTGGCATCCCAGACAGGTTCAGTGGCAGTGG GTCTGGGACAGACTTCACTCTCACCATCAGCAGACTGGAG CCTGAAGATTTTGCAGTGTATTACTGTCAGCAGTATGGTA GCTCACCGCTCACTTTCGGCGGAGGGACCAAGGTGGAGAT CAAA |
| SEQ ID NO: 47 | Nucleotide sequence of the light chain variable region of the 2A7 human monoclonal antibody | GAAATTGTGTTGACGCAGTCTCCAGGCACCCTGTCTTTGT CTCCAGGGGAAAGAGCCACCCTCTCCTGCAGGGCCAGTCA GAGTGTTAGCAGCAGCTACTTAGCCTGGTACCAGCAGAAA CCTGGCCAGGCTCCCAGGCTCCTCATCTATGGTGCATCCA GCAGGGCCACTGGCATCCCAGACAGGTTCAGTGGCAGTGG GTCTGGGACAGACTTCACTCTCACCATCAGCAGACTGGAG CCTGAAGATTTTGCAGTGTATTAGTGTCAGCAGTATGGTA GCTCACCCATGTACACTTTTGGCCAGGGGACCAAGCTGGA GATCAAA |
| SEQ ID NO: 48 | Nucleotide sequence of the light chain variable region of the 2F9 human monoclonal antibody | GAAATTGTGTTGACGCAGTCTCCAGGCACCCTGTCTTTGT CTCCAGGGGAAAGAGCCACCCTCTCCTGCAGGGCCAGTCA GAGTGTTAGCAGCAGCTACTTAGCCTGGTACCAGCAGAAA CCTGGCCAGGCTCCCAGGCTCCTCATCTATGGTGCATCCA GCAGGGCCACTGGCATCCCAGACAGGTTCAGTGGCAGTGG GTCTGGGACAGACTTCACTCTCACCATCAGCAGACTGGAG CCTGAAGATTTTGCAGTGTATTACTGTCAGCAGTATGGTA GCTCACCTCTGTACACTTTTGGCCAGGGGACCAAGCTGGA GATCAAA |
| SEQ ID NO: 49 | Nucleotide sequence of the light chain variable region of the 12E1 human monoclonal antibody | GAAATTGTGTTGACACAGTCTCCAGCCACCCTGTCTTTGT CTCCAGGGGAAAGAGCCACCCTCTCCTGCAGGGCCAGTCA GAGTGTTAGCAGCTACTTAGCCTGGTACCAACAGAAACCT GGCCAGGCTCCCAGGCTCCTCATCTATGATGCATCCAACA GGGCCACTGGCATCCCAGCCAGGTTCAGTGGCAGTGGGTC TGGGACAGACTTCACTCTCACCATCAGCAGCCTAGAGCCT GAAGATTTTGCAGTTTATTACTGTCAGCAGCGTAGGACGT TCGGCCAAGGGACCAAGGTGGAAATCAAA |
| SEQ ID NO: 50 | Nucleotide sequence of the light chain variable region of the 13D12 human monoclonal antibody | GAAATTGTGTTGACGCAGTCTCCAGGCACCCTGTCTTTGT CTCCAGGGGAAAGAGCCACCCTCTCCTGCAGGGCCAGTCA GAGTGTTAGCAGCAGCTACTTAGCCTGGTACCAGCAGAAA CCTGGCCAGGCTCCCAGGCTCCTCATCTATGGTGCATCCA GCAGGGCCACTGGCATCCCAGACAGGTTCAGTGGCAGTGG GTCTGGGACAGACTTCACTCTCACCATCAGCAGACTGGAG CCTGAAGATTTTGCAGTGTATTACTGTCAGCAGTATGGTA GCTCACCTCGGACGTTCGGCCAAGGGACCAAGGTGGAAAT CAAA |
| SEQ ID NO: 51 | Amino acid sequence of the human germline $V_H$4-34 | QVQLQQWGAGLLKPSETLSLTCAVYGGSFSGYYWSWIRQP PGKGLEWIGEINHSGSTNYNPSLKSRVTISVDTSKNQFSL KLSSVTAADTAVYYCAR |
| SEQ ID NO: 52 | Amino acid sequence of the human germline $V_H$3-53 | EVQLVESGGGLIQPGGSLRLSCAASGFTVSSNYMSWVRQA PGKGLEWVSVIYSGGSTYYADSVKGRFTISRDNSKNTLYL QMNSLRAEDTAVYYCAR |
| SEQ ID NO: 53 | Amino acid sequence of the human germline $V_H$3-9/D3-10/JH6b | EVQLVESGGGLVQPGRSLRLSCAASGFTFDDYAMHWVRQA PGKGLEWVSGISWNSGSIGYADSVKGRFTISRDNAKNSLY LQMNSLRAEDTALYYCAKDYGSGSYYYYYGMDVWGQGTTV TVSS |
| SEQ ID NO: 54 | Amino acid sequence of the human germline $V_K$ A27 | EIVLTQSPGTLSLSPGERATLSCRASQSVSSSYLAWYQQK PGQAPRLLIYGASSRATGIPDRFSGSGSGTDFTLTISRLE PEDFAVYYCQQYGSSP |
| SEQ ID NO: 55 | Amino acid sequence of the human germline $V_K$ L6/JK1 | EIVLTQSPATLSLSPGERATLSCRASQSVSSYLAWYQQKP GQAPRLLIYDASNRATGIPARFSGSGSGTDFTLTISSLEP EDFAVYYCQQRSNWTFGQGTKVEIK |

Given that each of the human antibodies designated 1G11, 2A7, 2F9, 12E1 and 13D12 can bind to O8E and that antigen-binding specificity is provided primarily by the CDR1, CDR2 and CDR3 regions, the $V_H$ CDR1, CDR2 and CDR3 sequences and $V_k$ CDR1, CDR2 and CDR3 sequences can be "mixed and matched" (i.e. CDRs from different antibodies can be mixed and matched, although each antibody must contain a $V_H$ CDR1, CDR2 and CDR3 and a $V_k$ CDR1, CDR2 and CDR3) to create other anti-O8E binding molecules of this disclosure. O8E binding of such "mixed and matched" antibodies can be tested using the binding assays described above and in the Examples (e.g., FACS, ELISAs, Biacore® system analysis). Typically, when $V_H$ CDR sequences are mixed and matched, the CDR1, CDR2 and/or CDR3 sequence from a particular $V_H$ sequence is replaced with a structurally similar CDR sequence(s). Likewise, when $V_k$ CDR sequences are mixed and matched, the CDR1, CDR2 and/or CDR3 sequence from a particular $V_k$ sequence typically is replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences disclosed herein for monoclonal antibodies 1G11, 2A7, 2F9, 12E1 and 13D12.

Accordingly, in another aspect, this disclosure provides an isolated monoclonal antibody or antigen binding portion thereof comprising:
 (a) a heavy chain variable region CDR1 comprising an amino acid sequence selected from the group consisting of SEQ ID NOs: 11, 12, 13, 14 and 15;
 (b) a heavy chain variable region CDR2 comprising an amino acid sequence selected from the group consisting of SEQ ID NOs: 16, 17, 18, 19 and 20;
 (c) a heavy chain variable region CDR3 comprising an amino acid sequence selected from the group consisting of SEQ ID NOs: 21, 22, 23, 24 and 25;
 (d) a light chain variable region CDR1 comprising an amino acid sequence selected from the group consisting of SEQ ID NOs: 26, 27, 28, 29 and 30;
 (e) a light chain variable region CDR2 comprising an amino acid sequence selected from the group consisting of SEQ ID NOs: 31, 32, 33, 34 and 35; and
 (f) a light chain variable region CDR3 comprising an amino acid sequence selected from the group consisting of SEQ ID NOs: 36, 37, 38, 39 and 40; wherein the antibody specifically binds O8E, typically human O8E.

In a preferred embodiment, the antibody comprises:
 (a) a heavy chain variable region CDR1 comprising SEQ ID NO: 11;
 (b) a heavy chain variable region CDR2 comprising SEQ ID NO: 16;
 (c) a heavy chain variable region CDR3 comprising SEQ ID NO: 21;
 (d) a light chain variable region CDR1 comprising SEQ ID NO: 26;
 (e) a light chain variable region CDR2 comprising SEQ ID NO: 31; and
 (f) a light chain variable region CDR3 comprising SEQ ID NO: 36.

In another preferred embodiment, the antibody comprises:
 (a) a heavy chain variable region CDR1 comprising SEQ ID NO: 12;
 (b) a heavy chain variable region CDR2 comprising SEQ ID NO: 17;
 (c) a heavy chain variable region CDR3 comprising SEQ ID NO: 22;
 (d) a light chain variable region CDR1 comprising SEQ ID NO: 27;
 (e) a light chain variable region CDR2 comprising SEQ ID NO: 32; and
 (f) a light chain variable region CDR3 comprising SEQ ID NO: 37.

In another preferred embodiment, the antibody comprises:
 (a) a heavy chain variable region CDR1 comprising SEQ ID NO: 13;
 (b) a heavy chain variable region CDR2 comprising SEQ ID NO: 18;
 (c) a heavy chain variable region CDR3 comprising SEQ ID NO: 23;
 (d) a light chain variable region CDR1 comprising SEQ ID NO: 28;
 (e) a light chain variable region CDR2 comprising SEQ ID NO: 33; and
 (f) a light chain variable region CDR3 comprising SEQ ID NO: 38.

In another preferred embodiment, the antibody comprises:
 (a) a heavy chain variable region CDR1 comprising SEQ ID NO: 14;
 (b) a heavy chain variable region CDR2 comprising SEQ ID NO: 19;
 (c) a heavy chain variable region CDR3 comprising SEQ ID NO: 24;
 (d) a light chain variable region CDR1 comprising SEQ ID NO: 29;
 (e) a light chain variable region CDR2 comprising SEQ ID NO: 34; and
 (f) a light chain variable region CDR3 comprising SEQ ID NO: 39.

In another preferred embodiment, the antibody comprises:
 (a) a heavy chain variable region CDR1 comprising SEQ ID NO: 15;
 (b) a heavy chain variable region CDR2 comprising SEQ ID NO: 20;
 (c) a heavy chain variable region CDR3 comprising SEQ ID NO: 25;
 (d) a light chain variable region CDR1 comprising SEQ ID NO: 30;
 (e) a light chain variable region CDR2 comprising SEQ ID NO: 35; and
 (f) a light chain variable region CDR3 comprising SEQ ID NO: 40.

It is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, for example, Klimka et al., *British J. of Cancer* 83(2):252-260 (2000) (describing the production of a humanized anti-CD30 antibody using only the heavy chain variable domain CDR3 of marine anti-CD30 antibody Ki-4); Beiboer et al., *J. Mol. Biol.* 296:833-849 (2000) (describing recombinant epithelial glycoprotein-2 (EGP-2) antibodies using only the heavy chain CDR3 sequence of the parental murine MOC-31 anti-EGP-2 antibody); Rader et al., *Proc. Natl. Acad. Sci. U.S.A.* 95:8910-8915 (1998) (describing a panel of humanized anti-integrin $\alpha_v\beta_3$ antibodies using a heavy and light chain variable CDR3 domain of a murine anti-integrin $\alpha_v\beta_3$ antibody LM609 wherein each member antibody comprises a distinct sequence outside the CDR3 domain and capable of binding the same epitope as the parent inuring antibody with affinities as high or higher than the parent murine antibody); Barbas et al., *J. Am. Chem. Soc.* 116:2161-2162 (1994) (disclosing that the CDR3 domain provides the most significant contribution to antigen binding); Barbas et al., *Proc. Natl. Acad. Sci. U.S.A.* 92:2529-2533 (1995) (describing the grafting of heavy chain CDR3 sequences of three Fabs (SI-1, SI-40 and SI-32) against human placental DNA onto the heavy chain of an anti-tetanus toxoid Fab thereby replacing the existing heavy chain CDR3 and demonstrating that the CDR3 domain alone conferred binding specificity); and Ditzel et al., *J. Immunol.* 157:739-749 (1996) (describing grafting studies wherein transfer of only the heavy chain CDR3 of a parent polyspecific Fab LNA3 to a heavy chain of a monospecific IgG tetanus toxoid-binding Fab p313 antibody was sufficient to retain binding specificity of the parent Fab). Each of these references is hereby incorporated by reference in its entirety.

Accordingly, within certain aspects, the present disclosure provides monoclonal antibodies comprising one or more heavy and/or light chain CDR3 domain from a non-human antibody, such as a mouse or rat antibody, wherein the monoclonal antibody is capable of specifically binding to O8E. Within some embodiments, such inventive antibodies comprising one or more heavy and/or light chain CDR3 domain from a non-human antibody (a) are capable of competing for binding with; (b) retain the functional characteristics; (c) bind to the same epitope; and/or (d) have a similar binding affinity as the corresponding parental non-human antibody.

Within other aspects, the present disclosure provides monoclonal antibodies comprising one or more heavy and/or light chain CDR3 domain from a first human antibody, such as, for example, a human antibody obtained from a non-human animal, wherein the first human antibody is capable of specifically binding to O8E and wherein the CDR3 domain from the first human antibody replaces a CDR3 domain in a human antibody that is lacking binding specificity for O8E to generate a second human antibody that is capable of specifically binding to O8E. Within some embodiments, such inventive antibodies comprising one or more heavy and/or light chain CDR3 domain from the first human antibody (a) are capable of competing for binding with; (b) retain the functional characteristics; (c) bind to the same epitope; and/or (d) have a similar binding affinity as the corresponding parental first human antibody.

Antibodies Having Particular Germline Sequences

In certain embodiments, an antibody of this disclosure comprises a heavy chain variable region from a particular germline heavy chain immunoglobulin gene and/or a light chain variable region from a particular germline light chain immunoglobulin gene.

For example, in a preferred embodiment, this disclosure provides an isolated monoclonal antibody or an antigen-binding portion thereof, comprising a heavy chain variable region that is the product of or derived from a human $V_H$ 4-34 gene, wherein the antibody specifically binds O8E. In another preferred embodiment, this disclosure provides an isolated monoclonal antibody or an antigen-binding portion thereof, comprising a heavy chain variable region that is the product of or derived from a human $V_H$ 3-53 gene, wherein the antibody specifically binds O8E. In another preferred embodiment, this disclosure provides an isolated monoclonal antibody or an antigen-binding portion thereof, comprising a heavy chain variable region that is the product of or derived from a combined human $V_H$ 3-9/D3-10/JH6b gene, wherein the antibody specifically binds O8E.

In another preferred embodiment, this disclosure provides an isolated monoclonal antibody or an antigen-binding portion thereof, comprising a light chain variable region that is the product of or derived from a human $V_K$ A27 gene, wherein the antibody specifically binds O8E. In another preferred embodiment, this disclosure provides an isolated monoclonal antibody or an antigen-binding portion thereof, comprising a light chain variable region that is the product of or derived from a combined human $V_K$ L6/JK1 gene, wherein the antibody specifically binds O8E.

In yet another preferred embodiment, this disclosure provides an isolated monoclonal antibody or antigen-binding portion thereof, wherein the antibody:

(a) comprises a heavy chain variable region that is the product of or derived from a human $V_H$ 4-34 gene, a human $V_H$ 3-53 gene or a combined human $V_H$ 3-9/D3-10/JH6b gene (which genes encode the amino acid sequences set forth in SEQ ID NOs: 51, 52 and 53, respectively);

(b) comprises a light chain variable region that is the product of or derived from a human $V_K$ A27 gene or a combined human $V_K$ L6/JK1 gene (which genes encode the amino acid sequences set forth in SEQ ID NOs: 54 and 55, respectively); and (c) the antibody specifically binds to O8E, typically human O8E.

Examples of antibodies having $V_H$ and $V_K$ of $V_H$ 4-34 and $V_K$ A27, respectively, are 1G11 and 13D12. Examples of antibodies having $V_H$ and $V_K$ of $V_H$ 3-53 and $V_K$ A27, respectively, are 2A7 and 2F9. An example of an antibody having $V_H$ and $V_K$ of $V_H$ 3-9/D 3-10/JH6b and $V_K$ L6/JK1, respectively, is 12E1.

As used herein, a human antibody comprises heavy or light chain variable regions that is "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e. greatest % identity) to the sequence of the human antibody. A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences), In certain cases, a human antibody may be at least 95% or even at least 96%, 97%, 98% or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5 or even no more than 4, 3, 2 or 1 amino acid difference from the amino acid sequence encoded by the germline immunoglobulin gene.

Homologous Antibodies

In yet another embodiment, an antibody of this disclosure comprises heavy and light chain variable regions comprising amino acid sequences that are homologous to the amino acid sequences of the preferred antibodies described herein and wherein the antibodies retain the desired functional properties of the anti-O8E antibodies of this disclosure.

For example, this disclosure provides an isolated monoclonal antibody or antigen binding portion thereof, comprising a heavy chain variable region and a light chain variable region, wherein:
(a) the heavy chain variable region comprises an amino acid sequence that is at least 80% homologous to an amino acid sequence selected from the group consisting of SEQ ID NOs: 1, 2, 3, 4; and 5
(b) the light chain variable region comprises an amino acid sequence that is at least 80% homologous to an amino acid sequence selected from the group consisting of SEQ ID NOs: 6, 7, 8; 9 and 10;
(c) the antibody binds to human O8E with a $K_D$ of $1 \times 10^{-7}$ M or less; and
(d) the antibody binds to human CHO cells transfected with O8E.

In various embodiments, the antibody can be, for example, a human antibody, a humanized antibody or a chimeric antibody.

In other embodiments, the $V_H$ and/or $V_L$ amino acid sequences may be 85%, 90%, 95%, 96%, 97%, 98% or 99% homologous to the sequences set forth above. An antibody having $V_H$ and $V_L$ regions having high (i.e. 80% or greater) homology to the $V_H$ and $V_L$ regions of the sequences set forth above, can be obtained by mutagenesis (e.g., site-directed or PCR-mediated mutagenesis) of nucleic acid molecules encoding SEQ ID NOs: 41, 42, 43, 44, 45, 46, 47, 48, 49 and 50, followed by testing of the encoded altered antibody for retained function (i.e., the functions set forth in (c) and (d) above), using the functional assays described herein.

As used herein, the percent homology between two amino acid sequences is equivalent to the percent identity between the two sequences. The percent identity between the two sequences is a function of the number of identical positions shared by the sequences (i.e. % homology=# of identical positions/total # of positions×100), taking into account the number of gaps and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package, using either a Blossum 62 matrix or a PAM250 matrix and a gap weight of 16, 14, 12, 10, 8, 6 or 4 and a length weight of 1, 2, 3, 4, 5 or 6.

Additionally or alternatively, the protein sequences of the present disclosure can further be used as a "query sequence" to perform a search against public databases to, for example, identify related sequences. Such searches can be performed using the XBLAST program (version 2.0) of Altschul, et al. (1990) *J. Mol. Biol.* 215:403-10. BLAST protein searches can be performed with the XBLAST program, score=50, wordlength=3 to obtain amino acid sequences homologous to the antibody molecules of this disclosure. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See the National Center for Biotechnology Information Website on the Internet.

Antibodies with Conservative Modifications

In certain embodiments, an antibody of this disclosure comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein (e.g., 1G11, 2A7, 2F9, 12E1 or 13D12) or conservative modifications thereof and wherein the antibodies retain the desired functional properties of the anti-O8E antibodies of this disclosure. Accordingly, this disclosure provides art isolated monoclonal antibody or antigen binding portion thereof, comprising a heavy chain variable region comprising CDR1, CDR2 and CDR3 sequences and a light chain variable region comprising CDR1, CDR2 and CDR3 sequences, wherein:
(a) the heavy chain variable region CDR3 sequence comprises an amino acid sequence selected from the group consisting of amino acid sequences of SEQ ID NOs: 21, 22, 23, 24 and 25 and conservative modifications thereof;
(b) the light chain variable region CDR3 sequence comprises an amino acid sequence selected from the group consisting of amino acid sequence of SEQ ID NOs: 36, 37, 38, 39 and 40 and conservative modifications thereof;
(c) the antibody binds to human O8E with a $K_D$ of $1 \times 10^{-7}$ M or less; and
(d) the antibody binds to human CHO cells transfected with O8E.

In a preferred embodiment, the heavy chain variable region CDR2 sequence comprises an amino acid sequence selected from the group consisting of amino acid sequences of SEQ ID NOs: 16, 17, 18, 19 and 20 and conservative modifications thereof; and the light chain variable region CDR2 sequence comprises an amino acid sequence selected from the group consisting of amino acid sequences of SEQ ID NOs: 31, 32, 33, 34 and 35 and conservative modifications thereof. In another preferred embodiment, the heavy chain variable region CDR1 sequence comprises an amino acid sequence selected from the group consisting of amino acid sequences of SEQ ID NOs: 11, 12, 13, 14 and 15 and conservative modifications thereof; and the light chain variable region CDR1 sequence comprises an amino acid sequence selected from the group consisting of amino acid sequences of SEQ ID NOs: 26, 27, 28, 29 and 30 and conservative modifications thereof.

In various embodiments, the antibody can be, for example, human antibodies, humanized antibodies or chimeric antibodies.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of this disclosure by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of this disclosure can be replaced with other amino acid residues from the same side chain family and the altered antibody can be tested for retained function.

Antibodies that Bind to the Same Epitope as Anti-O8E Antibodies of this Disclosure In another embodiment, this disclosure provides antibodies that bind to the same epitope on human O8E as any of the O8E monoclonal antibodies of this disclosure (i.e. antibodies that have the ability to cross-compete for binding to O8E with any of the monoclonal antibodies of this disclosure). In preferred embodiments, the reference antibody for cross-competition studies can be the monoclonal antibody 1G11 (having $V_H$ and $V_L$ sequences as shown in SEQ ID NOs: 1 and 6, respectively) or the monoclonal antibody 2A7 (having $V_H$ and $V_L$ sequences as shown in SEQ ID NOs: 2 and 7, respectively) or the monoclonal antibody 2F9 (having $V_H$ and $V_L$ sequences as shown in SEQ ID NOs: 3 and 8, respectively) or the monoclonal antibody 12E1 (having $V_H$ and $V_L$ sequences as shown in SEQ ID NOs: 4 and 9, respectively) or the monoclonal antibody 13D12 (having $V_H$ and $V_L$ sequences as shown in SEQ ID NOs: 5 and 10, respectively). Such cross-competing antibodies can be identified based on their ability to cross-compete with 1G11, 2A7, 2F9, 12E1 or 13D12 in standard O8E binding assays. For example, BIAcore® system analysis, ELISA assays or flow cytometry may be used to demonstrate cross-competition with the antibodies of the current disclosure. The ability of a test antibody to inhibit the binding of, for example, 1G11, 2A7, 2F9, 12E1 or 13D12 to human O8E demonstrates that the test antibody can compete with 1G11, 2A7, 2F9, 12E1 or 13D12 for binding to human O8E and thus binds to the same epitope on human O8E as 1G11, 2A7, 2F9, 12E1 or 13D12. In a preferred embodiment, the antibody that binds to the same epitope on human O8E as 1G11, 2A7, 2F9, 12E1 or 13D12 is a human monoclonal antibody. Such human monoclonal antibodies can be prepared and isolated as described in the Examples.

Engineered and Modified Antibodies

An antibody of this disclosure further can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e. $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) *Nature* 332:323-327; Jones, P. et al. (1986) *Nature* 321:522-525; Queen, C. et al. (1989) *Proc. Natl. Acad*, See. USA. 86:10029-10033; U.S. Pat. No. 5,225,539 to Winter and U.S. Pat. Nos. 5,530,101; 5,585,089; 5,693,762 and 6,180,370 to Queen et al.)

Accordingly, another embodiment of this disclosure pertains to an isolated monoclonal antibody or antigen binding portion thereof, comprising a heavy chain variable region comprising CDR1, CDR2 and CDR3 sequences comprising an amino acid sequence selected from the group consisting of SEQ ID NOs: 11, 12, 13, 14 and 15; SEQ ID NOs: 16, 17, 18, 19 and 20; and SEQ ID NOs: 21, 22, 23, 24 and 25; respectively and a light chain variable region comprising CDR1, CDR2 and CDR3 sequences comprising an amino acid sequence selected from the group consisting of SEQ ID NOs: 26, 27, 28, 29 and 30; SEQ ID NOs: 31, 32, 33, 34 and 35; and SEQ ID NOs: 36, 37, 38, 39 and 40; respectively. Thus, such antibodies contain the $V_H$ and $V_L$ CDR sequences of monoclonal antibodies 1G11, 2A7, 2F9, 12E1 or 13D12 yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_H$ Segments Reveals a Strong Bias in their Usage" *Eur. J. Immunol.* 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank accession numbers: 1-69 (NG_0010109, NT_024637 and BC070333), 3-33 (NG_0010109 and NT_024637) and 3-7 (NG_0010109 and NT_024637). As another example, the following heavy chain germline sequences found in the HCo12 HuMAb mouse are available in the accompanying Genbank accession numbers: 1-69 (NG_0010109, NT_024637 and BC070333), 5-51 (NG_0010109 and NT_024637), 4-34 (NG_0010109 and NT_024637), 3-30.3 (CAJ556644) and 3-23 (AJ406678).

Antibody protein sequences are compared against a compiled protein sequence database using one of the sequence similarity searching methods called the Gapped BLAST (Altschul et at. (1997) *Nucleic Acids Research* 25:3389-3402), which is well known to those skilled in the art. BLAST is a heuristic algorithm in that a statistically significant alignment between the antibody sequence and the database sequence is likely to contain high-scoring segment pairs (HSP) of aligned words. Segment pairs whose scores cannot be improved by extension or trimming is called a hit. Briefly, the nucleotide sequences of VBASE origin (see the MRC Centre for Protein Engineering V BASE website on the Internet) are translated and the region between and including FR1 through FR3 framework region is retained. The database sequences have an average length of 98 residues. Duplicate sequences which are exact matches over the entire length of the protein are removed. A BLAST search for proteins using the program blastp with default, standard parameters except the low complexity filter, which is turned off, and the substitution matrix of BLOSUM62, filters for top 5 hits yielding sequence matches. The nucleotide sequences are translated in all six frames and the frame with no stop codons in the matching segment of the database sequence is considered the potential hit. This is in turn confirmed using the BLAST program tblastx, which translates the antibody sequence in all six frames and compares those translations to the VBASE nucleotide sequences dynamically translated in all six frames.

The identities are exact amino acid matches between the antibody sequence and the protein database over the entire length of the sequence. The positives (identities+substitution match) are not identical but amino acid substitutions guided by the BLOSUM62 substitution matrix. If the antibody sequence matches two of the database sequences with same identity, the hit with most positives would be decided to be the matching sequence hit.

Preferred framework sequences for use in the antibodies of this disclosure are those that are structurally similar to the framework sequences used by selected antibodies of this disclosure, e.g., similar to the $V_H$ 4-34 framework sequences (SEQ ID NO: 51) and/or the $V_H$ 3-53 framework sequences (SEQ ID NO: 52) and/or the combined $V_H$ 3-9/D3-10/JH6b framework sequences (SEQ ID NO: 53) and/or the $V_K$ A27 framework sequences (SEQ ID NO: 54) and/or the combined $V_K$ L6/JK1 framework sequences (SEQ ID NO: 55) used by preferred monoclonal antibodies of this disclosure. The $V_H$ CDR1, CDR2 and CDR3 sequences and the $V_K$ CDR1, CDR2 and CDR3 sequences, can be grafted onto framework regions that have the identical sequence as that found in the germline immunoglobulin gene from which the framework sequence derive or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the $V_H$ and/or $V_K$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding or other functional property of interest, can be evaluated in in vitro or in vivo assays as described herein and provided in the Examples. Typically conservative modifications (as discussed above) are introduced. The mutations may be amino acid substitutions, additions or deletions, but are typically substitutions. Moreover, typically no more than one, two, three, four or five residues within a CDR region are altered.

Accordingly, in another embodiment, this disclosure provides isolated anti-O8E monoclonal antibodies or antigen binding portions thereof, comprising a heavy chain variable region comprising: (a) a $V_H$ CDR1 region comprising an amino acid sequence selected from the group consisting of SEQ ID NOs: 11, 12, 13, 14 and 15 or an amino acid sequence having one, two, three, four or five amino acid substitutions, deletions or additions as compared to SEQ ID NOs: 11, 12, 13, 14 and 15; (b) a $V_H$ CDR2 region comprising an amino acid sequence selected from the group consisting of SEQ ID NOs: 16, 17, 18, 19 and 20 or an amino acid sequence having one, two, three, four or five amino acid substitutions, deletions or additions as compared to SEQ ID NOs: 16, 17, 18, 19 and 20; (c) a $V_H$ CDR3 region comprising an amino acid sequence selected from the group consisting of SEQ ID NOs: 21, 22, 23, 24 and 25 or an amino acid sequence having one, two, three, four or five amino acid substitutions, deletions or additions as compared to SEQ ID NOs: 21, 22, 23, 24 and 25; (d) a $V_K$ CDR1 region comprising an amino acid sequence selected from the group consisting of SEQ ID NOs: 26, 27, 28, 29 and 30 or an amino acid sequence having one, two, three, four or five amino acid substitutions, deletions or additions as compared to SEQ ID NOs: 26, 27, 28, 29 and 30; (e) a $V_K$ CDR2 region comprising an amino acid sequence selected from the group consisting of SEQ ID NOs: 31, 32, 33, 34 and 35 or an amino acid sequence having one, two, three, four or five amino acid substitutions, deletions or additions as compared to SEQ ID NOs: 31, 32, 33, 34 and 35; and (f) a $V_K$ CDR3 region comprising an amino acid sequence selected from the group consisting of SEQ ID NOs: 36, 37, 38, 39 and 40 or an amino acid sequence having one, two, three, four or five amino acid substitutions, deletions or additions as compared to SEQ ID NOs: 36, 37, 38, 39 and 40.

Engineered antibodies of this disclosure include those in which modifications have been made to framework residues within $V_H$ and/or $V_K$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived.

For example, for 1G11, amino acid residue #71 (within FR3) of $V_H$ is an alanine whereas this residue in the corresponding $V_H$ 4-34 germline sequence is a valine. To return the framework region sequences to their germline configuration, the somatic mutations can be "backmutated" to the germline sequence by, for example, site-directed mutagenesis or PCR-mediated mutagenesis (e.g., residue #71 of FR3 of the $V_H$ of 1G11 can be "backmutated" from alanine to valine). Such "backmutated" antibodies are also intended to be encompassed by this disclosure.

As another example, for 1G11, amino acid residue #81 (within FR3) of $V_H$ is an arginine whereas this residue in the corresponding $V_H$ 4-34 germline sequence is a lysine. To return the framework region sequences to their germline configuration, for example, residue #81 of FR3 of the $V_H$ of 1G11 can be "backmutated" from arginine to lysine. Such "backmutated" antibodies are also intended to be encompassed by this disclosure.

As another example, for 13D12, amino acid residue #83 (within FR3) of $V_H$ is an asparagine whereas this residue in the corresponding $V_H$ 4-34 germline sequence is a serine. To return the framework region sequences to their germline configuration, for example, residue #83 of FR3 of the $V_H$ of 13D12 can be "backmutated" from asparagine to serine. Such "backmutated" antibodies are also intended to be encompassed by this disclosure.

As another example, for 2A7, amino acid residue #67 (within FR3) of $V_H$ is a valine whereas this residue in the corresponding $V_H$ 3-53 germline sequence is an phenylalanine. To return the framework region sequences to their germline configuration, for example, residue #67 of FR3 of the $V_H$ of 2A7 can be "backmutated" from valine to phenylalanine. Such "backmutated" antibodies are also intended to be encompassed by this disclosure.

As another example, for 2F9, amino acid residue #28 (within FR1) of $V_H$ is a isoleucine whereas this residue in the corresponding $V_H$ 3-53 germline sequence is a threonine. To return the framework region sequences to their germline configuration, for example, residue #28 of FR1 of the $V_H$ of 2F9 can be "backmutated" from isoleucine to threonine. Such "backmutated" antibodies are also intended to be encompassed by this disclosure.

As another example, for 12E1, amino acid residue #23 (within FR1) of $V_H$ is a valine whereas this residue in the corresponding $V_H$ 3-9 germline sequence is an alanine. To return the framework region sequences to their germline configuration, for example, residue #23 of FR1 of the $V_H$ of 12E1 can be "backmutated" from valine to alanine. Such "backmutated" antibodies are also intended to be encompassed by this disclosure.

As another example, for 1G11, amino acid residue #7 (within FR1) of $V_k$ is a phenylalanine whereas this residue in the corresponding $V_k$ A27 germline sequence is a serine. To return the framework region sequences to their germline configuration, for example, residue #7 of FR1 of the $V_k$ of 1G11 can be "backmutated" from phenylalanine to serine. Such "backmutated" antibodies are also intended to be encompassed by this disclosure.

As another example, for 1G11, amino acid residue #47 (within FR2) of $V_k$ is a valine whereas this residue in the corresponding $V_k$ A27 germline sequence is a leucine. To return the framework region sequences to their germline configuration, for example, residue #47 of FR2 of the $V_k$ of 1G11 can be "backmutated" from valine to leucine. Such "backmutated" antibodies are also intended to be encompassed by this disclosure.

Another type of framework modification involves mutating one or more residues within the framework region or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

Engineered antibodies of this disclosure also include those in which modifications have been made to amino acid residues to increase or decrease immunogenic responses through amino acid modifications that alter interaction of a T-cell epitope on the antibody (see e.g., U.S. Pat. Nos. 6,835,550; 6,897,049 and 6,936249).

In addition or alternative to modifications made within the framework or CDR regions, antibodies of this disclosure may be engineered to include modifications within the Fc region, typically to alter one or more functional properties of the antibody, such as serum half-life, complement fixation, Fc receptor binding and/or antigen-dependent cellular cytotoxicity. Furthermore, an antibody of this disclosure may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication. WO 94/29351 by Bodmer et al.

In yet another example, the Fc region is modified to increase the ability of the antibody to mediate antibody dependent cellular cytotoxicity (ADCC) and/or to increase the affinity of the antibody for an Fcy receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication. WO 00/42072 by Prem. Moreover, the binding sites on human IgG1 for FcγRI, FcγRII, FcγRIII and FcRn have been mapped and variants with improved binding have been described (see Shields, R. L. et al. (2001) *J. Biol. Chem.* 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In still another embodiment, the glycosylation of an antibody is modified. For example, an aglycoslated antibody can be made (i.e. the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of this disclosure to thereby produce an antibody with altered glycosylation. For example, the cell lines Ms704, Ms705 and Ms709 lack the fucosyltransferase gene, FUT8 (alpha (1,6) fucosyltransferase), such that antibodies expressed in the Ms704, Ms705 and Ms709 cell lines lack fucose on their carbohydrates. The Ms704, Ms705 and Ms709 FUT8$^{-/-}$ cell lines were created by the targeted disruption of the FUT8 gene in CHO/DG44 cells using two replacement vectors (see U.S. Patent Publication No. 20040110704 by Yamane et al. and Yamane-Ohnuki et al. (2004) *Biotechnol Bioeng* 87:614-22). As another example, EP 1,176,195 by Hanai et al. describes a cell line with a functionally disrupted FUT8 gene, which encodes a fucosyl transferase, such that antibodies expressed in such a cell line exhibit hypofucosylation by reducing or eliminating the alpha 1,6 bond-related enzyme. Hanai et al. also describe cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) *J. Biol. Chem.* 277:26733-26740). PCT Publication WO 99/54342 by Umana et al. describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al (1999) *Nat.* *Biotech.* 17:176-180). Alternatively, the fucose residues of the antibody may be cleaved off using a fucosidase enzyme. For example, the fucosidase alpha-L-fucosidase removes fucosyl residues from antibodies (Tarentino, A. L. et al. (1975) *Biochem.* 14:5516-23).

Another modification of the antibodies herein that is contemplated by this disclosure is pegylation. An antibody can be pegylated to, for example, increase the biological (e.g., serum) half life of the antibody. To pegylate an antibody, the antibody or fragment thereof, typically is reacted with polyethylene glycol (PEG), such as a reactive ester or aldehyde derivative of PEG, under conditions in which one or more PEG groups become attached to the antibody or antibody fragment. Typically, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivative other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of this disclosure. See for example, EP 0 154 316 by Nishimura et al. and EP 0 401 384 by Ishikawa et al.

Methods of Engineering Antibodies

As discussed above, the anti-O8E antibodies having $V_H$ and $V_K$ sequences disclosed herein can be used to create new anti-O8E antibodies by modifying the VH and/or $V_K$ sequences or the constant region(s) attached thereto. Thus, in another aspect of this disclosure, the structural features of an anti-O8E antibody of this disclosure, e.g. 1G11, 2A7, 2F9, 12E1 or 13D12, are used to create structurally related anti-O8E antibodies that retain at least one functional property of the antibodies of this disclosure, such as binding to human O8E. For example, one or more CDR regions of 1G11, 2A7, 2F9, 12E1 or 13D12 or mutations thereof, can be combined recombinantly with known framework regions and/or other CDRs to create additional, recombinantly-engineered, anti-O8E antibodies of this disclosure, as discussed above. Other types of modifications include those described in the previous section. The starting material for the engineering method is one or more of the $V_H$ and/or $V_K$ sequences provided herein or one or more CDR regions thereof. To create the engineered antibody, it is not necessary to actually prepare (i.e. express as a protein) an antibody having one or more of the $V_H$ and/or $V_K$ sequences provided herein or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, this disclosure provides a method for preparing an anti-O8E antibody comprising:

(a) providing: (i) a heavy chain variable region antibody sequence comprising a CDR1 sequence selected from the group consisting of SEQ ID NOs: 11, 12, 13, 14 and 15, a CDR2 sequence selected from the group consisting of SEQ ID NOs: 16, 17, 18, 19 and 20 and/or a CDR3 sequence selected from the group consisting of SEQ ID NOs: 21, 22, 23, 24 and 25; and/or (ii) a light chain variable region antibody sequence comprising a CDR1 sequence selected from the group consisting of SEQ ID NOs: 26, 27, 28, 29 and 30, a CDR2 sequence selected from the group consisting of SEQ ID NOs: 31, 32, 33, 34 and 35 and/or a CDR3 sequence selected from the group consisting of SEQ ID NOs: 36, 37, 38, 39 and 40;
(b) altering at least one amino acid residue within the heavy chain variable region antibody sequence and/or the light chain variable region antibody sequence to create at least one altered antibody sequence; and
(c) expressing the altered antibody sequence as a protein.

Standard molecular biology techniques can be used to prepare and express the altered antibody sequence.

Typically, the antibody encoded by the altered antibody sequence(s) is one that retains one, some or all of the functional properties of the anti-O8E antibodies described herein, which functional properties include, but are not limited to:
 (i) binds to human O8E with a $K_D$ of $1 \times 10^{-7}$ M or less;
 (ii) binds to human CHO cells transfected with O8E.

The functional properties of the altered antibodies can be assessed using standard assays available in the art and/or described herein, such as those set forth in the Examples (e.g., flow cytometry, binding assays).

In certain embodiments of the methods of engineering antibodies of this disclosure, mutations can be introduced randomly or selectively along all or part of an anti-O8E antibody coding sequence and the resulting modified anti-O8E antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly or a combination thereof. Alternatively, PCT Publication WO 03/074679 by Lazar et al. describes methods of using computational screening methods to optimize physiochemical properties of antibodies.

Nucleic Acid Molecules Encoding Antibodies of this Disclosure

Another aspect of this disclosure pertains to nucleic acid molecules that encode the antibodies of this disclosure. The nucleic acids may be present in whole cells, in a cell lysate or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al, ed. (1987) Current Protocols in Molecular Biology, Greene Publishing and Wiley Interscience, New York. A nucleic acid of this disclosure can be, for example, DNA or RNA and may or may not contain intronic sequences. In a preferred embodiment, the nucleic acid is a cDNA molecule.

Nucleic acids of this disclosure can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Preferred nucleic acids molecules of this disclosure are those encoding the VH and VL sequences of the 1G11, 2A7, 2F9, 12E1 or 13D12 monoclonal antibodies. DNA sequences encoding the $V_H$ sequences of 1G11, 2A7, 2F9, 12E1 and 13D12 are shown in SEQ ID NOs: 41, 42, 43, 44 and 45, respectively. DNA sequences encoding the $V_L$ sequences of 1G11, 2A7, 2F9, 12E1 and 13D12 are shown in SEQ ID NOs: 46, 47, 48, 49 and 50, respectively.

Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions (CH1, CH2 and CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most typically is an IgG1 or IgG4 constant region. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but most typically is a kappa constant region.

To create a scFv gene, the $V_H$- and $V_L$-encoding DNA fragments are operatively linked to another fragment encoding a flexible linker, e.g., encoding the amino acid sequence $(Gly_4-Ser)_3$, such that the $V_H$ and $V_L$ sequences can be expressed as a contiguous single-chain protein, with the $V_L$ and $V_H$ regions joined by the flexible linker (see e.g., Bird et al. (1988) Science 242:423-426; Huston et al (1988) Proc. Natl. Acad. Sci. USA 85:5879-5883; McCafferty et al, (1990) Nature 348:552-554).

Production of Monoclonal Antibodies of this Disclosure

Monoclonal antibodies (mAbs) of the present disclosure can be produced by a variety of techniques, including conventional monoclonal antibody methodology e.g., the standard somatic cell hybridization technique of Kohler and Milstein (1975) Nature 256: 495. Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies of the present disclosure can be prepared based on the sequence of a murine monoclonal antibody prepared as described above. DNA encoding the heavy and light chain immunoglobulins can be obtained from the non-human hybridoma of interest and engineered to contain human immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter and U.S. Pat. Nos. 5,530,101; 5,585,089; 5,693,762 and 6,180,370 to Queen et al.).

In a preferred embodiment, the antibodies of this disclosure are human monoclonal antibodies. Such human monoclonal antibodies directed against O8E can be generated using transgenic or transchromosomic mice carrying parts of the human immune system rather than the mouse system. These transgenic and transchromosomic mice include mice referred to herein as the HuMAb Mouse® and KM Mouse®, respectively and are collectively referred to herein as "human Ig mice."

The HuMAb Mouse® (Medarex, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al. (1994) Nature 368(6474): 856-859). Accordingly, the mice exhibit reduced expression of mouse IgM or κ and in response to immunization, the introduced human heavy and light chain transgenes undergo class switching and somatic mutation to generate high affinity human IgGκ monoclonal (Lonberg, N. et al. (1994), supra; reviewed in Lonberg, N. (1994) *Handbook of Experimental Pharmacology* 113:49-101; Lonberg, N. and Huszar, D. (1995) *Intern, Rev. Immunol.* 13: 65-93 and Harding, F. and Lonberg, N. (1995) *Ann. N.Y. Acad. Sci.* 764:536-546). The preparation and use of HuMab mice and the genomic modifications carried by such mice, is further described in Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen, S. et al. (1993) *EMBO J.* 12: 821-830; Tuaillon et al. (1994) *J. Immunol.* 152:2912-2920; Taylor, L. et al. (1994) *International Immunology* 6; 579-591; and Fishwild, D. et al. (1996) *Nature Biotechnology* 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies of this disclosure can be raised using a mouse that carries human immunoglobulin sequences on transgenes and transchomosomes, such as a mouse that carries a human heavy chain transgene and a human light chain transchromosome. Such mice, referred to herein as the "KM Mouse®", are described in detail in PCT Publication WO 02/43478 to Ishida et al.

Still further, alternative transgenic animal systems expressing human immunoglobulin genes are available in the art and can be used to raise anti-O8E antibodies of this disclosure. For example, an alternative transgenic system referred to as the Xenomouse (Abgenix, Inc.) can be used; such mice are described in, for example, U.S. Pat. Nos. 5,939,598; 6,075, 181; 6,114,598; 6,150,584 and 6,162,963 to Kucherlapati et al.

Moreover, alternative transchromosomic animal systems expressing human immunoglobulin genes are available in the art and can be used to raise anti-O8E antibodies of this disclosure. For example, mice carrying both a human heavy chain transchromosome and a human light chain tranchromosome, referred to as "TC mice" can be used; such mice are described in Tornizuka et al. (2000) *Proc. Natl. Acad. Sci. USA* 97:722-727. As another example, cows carrying human heavy and light chain transchromosomes have been described in the art (Kuroiwa et al. (2002) *Nature Biotechnology* 20:889-894) and can be used to raise anti-O8E antibodies of this disclosure.

Human monoclonal antibodies of this disclosure can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et at; U.S. Pat. Nos. 5,969,108 and 6,172, 197 to McCafferty et at; and U.S. Pat. Nos. 5,885,793; 6,521, 404; 6,544,731; 6,555,313; 6,582,915 and 6,593,081 to Griffiths et al.

Human monoclonal antibodies of this disclosure can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Immunization of Human Ig Mice

When human Ig mice are used to raise human antibodies of this disclosure, such mice can be immunized with a O8E-expressing cell line, a purified or enriched preparation of O8E antigen and/or recombinant O8E or an O8E fusion protein, as described by Lonberg, N. et al. (1994) *Nature* 368(6474): 856-859; Fishwild, D. et al. (1996) *Nature Biotechnology* 14: 845-851; and PCT Publication WO 98/24884 and WO 01/14424. Typically, the mice will be 6-16 weeks of age upon the first immunization. For example, a purified or recombinant preparation (5-50 μg) of O8E antigen can be used to immunize the human Ig mice intraperitoneally.

Detailed procedures to generate fully human monoclonal antibodies to O8E are described in Example 1 below. Cumulative experience with various antigens has shown that the transgenic mice respond when initially immunized intraperitoneally (IP) with antigen in complete Freund's adjuvant, followed by every other week IP immunizations up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained, for example, by retroorbital bleeds. The plasma can be screened by ELISA and mice with sufficient titers of anti-O8E human immunoglobulin can be used for fusions (as described in Example 1). Mice can be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo12 strains are used. Generation of HCo7 and HCo12 mouse strains are described in U.S. Pat. No. 5,770,429 and Example 2 of PCT Publication WO 01/09187, respectively. In addition, both HCo7 and HCo12 transgene can be bred together into a single mouse having two different human heavy chain transgenes (HCo7/HCo12). Alternatively or additionally, the KM Mouse® strain can be used, as described in PCT Publication WO 02/43478.

Generation of Hybridomas Producing Human Monoclonal Antibodies of this Disclosure To generate hybridomas producing human monoclonal antibodies of this disclosure, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-third the number of Sp2/0 nonsecreting mouse myeloma cells (ATCC, CRL 1581) with 50% PEG. Alternatively, the single cell suspensions of splenic lymphocytes from immunized mice can be fused to an equal number of Sp2/0 mouse myeloma cells using an electric field based electrofusion method, using a Cyto Pulse large chamber cell fusion electroporator (Cyto Pulse Sciences, Inc., Glen Burnie, Md.). Cells are plated at approximately $1 \times 10^5$ cells/well in flat bottom microliter plate, followed by a two week incubation in selective medium containing 10% fetal bovine serum (Hyclone, Logan, Utah), 10% P38801 (ATCC, CRL TIB-63) conditioned medium, 3-5% origen (IGEN) in DMEM (Mediatech, CRL 10013, with high glucose, L-glutamine and sodium pyruvate) plus 5 mM HEPES, 0.055 mM 2-mercaptoethanol, 50 mg/ml gentamycin and 1× HAT (Sigma, CRL P-7185). After approximately 1-2 weeks, cells can be cultured in medium in which the HAT is replaced with HT. Individual wells can then be screened by ELISA or FACS for human monoclonal IgM and IgG antibodies. The positive clones can then be screened for O8E positive antibodies on O8E recombinant protein by ELISA or on O8E expressing cells, for example CHO-O8E transfected cells, by FACS. Once extensive hybridoma growth occurs, medium can be observed usually after 10-14 days. The antibody secreting hybridomas can be replated, screened again and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS and the concentration can be determined by OD280 using 1.43 extinction coefficient. The monoclonal antibodies can be aliquoted and stored at −80° C.

Generation of Transfectomas Producing Monoclonal Antibodies of this Disclosure

Antibodies of this disclosure also can be produced in a host cell transfectoma using, for example, a combination of recombinant DNA techniques and gene transfection methods as is well known in the art (e.g., Morrison, S. (1985) Science 229:1202).

For example, to express the antibodies or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_K$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e. a signal peptide from a non-immunoglobulin protein).

In addition to the antibody chain genes, the recombinant expression vectors of this disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, the recombinant expression vectors of this disclosure may carry additional sequences, such as sequences that regulate replication of the vector in host cells (e.g. origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of this disclosure in either prokaryotic or eukaryotic host cells, expression of antibodies in eukaryotic cells and most typically mammalian host cells, is the most preferred because such eukaryotic cells and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. It (1985) *Immunology Today* 6:12-13).

Preferred mammalian host cells for expressing the recombinant antibodies of this disclosure include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more typically, secretion of the antibody into the culture medium in which the host cells are grown. Antibodies can be recovered from the culture medium using standard protein purification methods.

Characterization of Antibody Binding to Antigen

Antibodies of this disclosure can be tested for binding to O8E by, for example, flow cytometry. Briefly, O8E-expressing cells are freshly harvested from tissue culture flasks and a single cell suspension prepared. O8E-expressing cell suspensions are either stained with primary antibody directly or after fixation with 1% paraformaldehyde in PBS. Approximately one million cells are resuspended in PBS containing 0.5% BSA and 50-200 μg/ml of primary antibody and incubated on ice for 30 minutes. The cells are washed twice with PBS containing 0.1% BSA, 0.01% NaN$_3$, resuspended in 100 μl of 1:100 diluted FITC-conjugated goat-anti-human IgG (Jackson ImmunoResearch, West Grove, Pa.) and incubated on ice for an additional 30 minutes. The cells are again washed twice, resuspended in 0.5 ml of wash buffer and analyzed for fluorescent staining on a FACSCalibur cytometer (Becton-Dickinson, San Jose, Calif.).

Alternatively, antibodies of this disclosure can be tested for binding to O8E by standard ELISA. Briefly, microtiter plates are coated with purified O8E at 0.25 μg/ml in PBS and then blocked with 5% bovine serum albumin in PBS. Dilutions of antibody (e.g., dilutions of plasma from O8E-immunized mice) are added to each well and incubated for 1-2 hours at 37° C. The plates are washed with PBS/Tween and then incubated with secondary reagent (e.g., for human antibodies, a goat-anti-human IgG Fc-specific polyclonal reagent) conjugated to alkaline phosphatase for 1 hour at 37° C. After washing, the plates are developed with pNPP substrate (1 mg/ml) and analyzed at OD of 405-650. Typically, mice which develop the highest titers will be used for fusions.

An ELISA or FACS assay, as described above, can also be used to screen for hybridomas that show positive reactivity with O8E immunogen. Hybridomas that bind with high avidity to O8E are subcloned and further characterized. One clone from each hybridoma, which retains the reactivity of the parent cells (by ELISA or FACS), can be chosen for making a 5-10 vial cell bank stored at -140° C. and for antibody purification.

To purify anti-O8E antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS and the concentration can be determined by OD$_{280}$ using 1.43 extinction coefficient. The monoclonal antibodies can be aliquoted and stored at -80° C.

To determine if the selected anti-O8E monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using O8E coated-ELISA plates as described above. Biotinylated mAb binding can be detected with a strep-avidin-alkaline phosphatase probe. Alternatively, competition studies can be performed using radiolabelled antibody and unlabelled competing antibodies can be detected in a Scatchard analysis, as further described in the Examples below.

To determine the isotype of purified antibodies, isotype ELISAs can be performed using reagents specific for antibodies of a particular isotype. For example, to determine the isotype of a human monoclonal antibody, wells of microliter plates can be coated with 1 μg/ml of anti-human immunoglobulin overnight at 4° C. After blocking with 1% BSA, the plates are reacted with 1 μg/ml or less of test monoclonal antibodies or purified isotype controls, at ambient temperature for one to two hours. The wells can then be reacted with either human. IgG1 or human IgM-specific alkaline phosphatase-conjugated probes. Plates are developed and analyzed as described above.

Anti-O8E human IgGs can be further tested for reactivity with O8E antigen by Western blotting. Briefly, O8E can be prepared and subjected to sodium dodecyl sulfate polyacrylamide gel electrophoresis. After electrophoresis, the separated antigens are transferred to nitrocellulose membranes, blocked with 10% fetal calf serum and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Antibody Physical Properties

The antibodies of the present disclosure may be further characterized by the various physical properties of the anti-O8E antibodies. Various assays may be used to detect and/or differentiate different classes of antibodies based on these physical properties.

In some embodiments, antibodies of the present disclosure may contain one or more glycosylation sites in either the light or heavy chain variable region. The presence of one or more glycosylation sites in the variable region may result in increased immunogenicity of the antibody or an alteration of the pK of the antibody due to altered antigen binding (Marshall et al (1972) *Annu Rev Biochem* 41:673-702; Gala F A and Morrison S L (2004) *J Immunol* 1.72:5489-94; Wallick et al (1988) *J Exp Med* 168:1099-109; Spiro R G (2002) *Glycobiology* 12:43R-56R; Parekh et al (1985) *Nature* 316:452-7; Mimura et al. (2000) *Mol Immunol* 37:697-706). Glycosylation has been known to occur at motifs containing an N-X-S/T sequence. Variable region glycosylation may be tested using a Glycoblot assay, which cleaves the antibody to produce a Fab and then tests for glycosylation using an assay that measures periodate oxidation and Schiff base formation. Alternatively, variable region glycosylation may be tested using Dionex light chromatography (Dionex-LC), which cleaves saccharides from a Fab into monosaccharides and analyzes the individual saccharide content. In some instances, it is preferred to have an anti-O8E antibody that does not contain variable region glycosylation. This can be achieved either by selecting antibodies that do not contain the glycosylation motif in the variable region or by mutating residues within the glycosylation motif using standard techniques well known in the art.

In a preferred embodiment, the antibodies of the present disclosure do not contain asparagine isomerism sites. A deamidation or isoaspartic acid effect may occur on N-G or D-G sequences, respectively. The deamidation or isoaspartic acid effect results in the creation of isoaspartic acid which decreases the stability of an antibody by creating a kinked structure off a side chain carboxy terminus rather than the main chain. The creation of isoaspartic acid can be measured using an iso-quant assay, which uses a reverse phase HPLC to test for isoaspartic acid.

Each antibody will have a unique isoelectric point (pI), but generally antibodies will fall in the pH range of between 6 and 9.5. The pI for an IgG1 antibody typically falls within the pH range of 7-9.5 and the pI for an IgG4 antibody typically falls within the pH range of 6-8. Antibodies may have a pI that is outside this range. Although the effects are generally unknown, there is speculation that antibodies with a pI outside the normal range may have some unfolding and instability under in vivo conditions. The isoelectric point may be tested using a capillary isoelectric focusing assay, which creates a pH gradient and may utilize laser focusing for increased accuracy (Janini et al (2002) *Electrophoresis* 23:1605-11; Ma et al. (2001) *Chromatographia* 53:S75-89; Hunt et al (1998) *J Chromatogr A* 800:355-67). In some instances, it is preferred to have an anti-O8E antibody that contains a pI value that falls in the normal range. This can be achieved either by selecting antibodies with a pI in the normal range or by mutating charged surface residues using standard techniques well known in the art.

Each antibody will have a melting temperature that is indicative of thermal stability (Krishnamurthy R and Manning M C (2002) *Curr Pharm Biotechnol* 3:361-71). A higher thermal stability indicates greater overall antibody stability in vivo. The melting point of an antibody may be measure using techniques such as differential scanning calorimetry (Chen et al (2003) *Pharm Res* 20:1952-60; Ghirlando et al (1999) *Immunol Lett* 68:47-52). $T_{M1}$ indicates the temperature of the initial unfolding of the antibody. $T_{M2}$ indicates the temperature of complete unfolding of the antibody. Generally, it is preferred that the $T_{M1}$ of an antibody of the present disclosure is greater than 60° C., preferably greater than 65° C., even more preferably greater than 70° C. Alternatively, the thermal stability of an antibody may be measure using circular dichroism (Murray et al. (2002) *J Chromatogr Sci* 40:343-9).

In a preferred embodiment, antibodies are selected that do not rapidly degrade. Fragmentation of an anti-O8E antibody may be measured using capillary electrophoresis (CE) and MALDI-MS, as is well understood in the art (Alexander A J and Hughes D E (1995) *Anal Chem* 67:3626-32).

In another preferred embodiment, antibodies are selected that have minimal aggregation effects. Aggregation may lead to triggering of an unwanted immune response and/or altered or unfavorable pharmacokinetic properties. Generally, antibodies are acceptable with aggregation of 25% or less, preferably 20% or less, even more preferably 15% or less, even more preferably 10% or less and even more preferably 5% or less. Aggregation may be measured by several techniques well known in the art, including size-exclusion column (SEC) high performance liquid chromatography (HPLC) and light scattering to identify monomers, dimers, trimers or multimers.

Immunoconjugates

In another aspect, the present disclosure features an anti-O8E antibody or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thiotepa, chlorambucil, melphalan, carmustine (BSNU) and lomustine (CCNU), cyclothosphamide, busulfan, dibromomannitol, streptozotocin, mitomycin C and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin and anthramycin (AMC)) and anti-mitotic agents (e.g., vincristine and vinblastine).

Other preferred examples of therapeutic cytotoxins that can be conjugated to an antibody of this disclosure include duocarmycins, calicheamicins, maytansines and auristatins and derivatives thereof. An example of a calicheamicin antibody conjugate is commercially available (Mylotarg™; Wyeth-Ayerst).

Cytoxins can be conjugated to antibodies of this disclosure using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al. (2003) *Adv. Drug Deliv. Rev.* 55:199-215; Trail, P. A. et al. (2003) *Cancer Immunol. Immunother.* 52:328-337; Payne, G. (2003) *Cancer Cell* 3:207-212; Allen, T. M. (2002) *Nat. Rev. Cancer* 2:750-763; Pastan, I. and Kreitman., R. J. (2002) *Curr. Opin. Investig. Drugs* 3:1089-1091; Senter, P. D. and Springer, C. J. (2001) *Adv. Drug Deliv. Rev.* 53:247-264.

Antibodies of the present disclosure also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, iodine$^{125}$, indium$^{111}$, yttrium$^{90}$ and lutetium$^{177}$. Method for preparing radioimmunconjugates are established in the art. Examples of radioimmunoconjugates are commercially available, including Zevalin™ (IDEC Pharmaceuticals) and Bexxar™ (Corixa Pharmaceuticals) and similar methods can be used to prepare radioimmunoconjugates using the antibodies of this disclosure.

The antibody conjugates of this disclosure can be used to modify a given biological response and the drug moiety is not to be construed as limited to classical chemical therapeutic agents. For example, the drug moiety may be a protein or polypeptide possessing a desired biological activity. Such proteins may include, for example, an enzymatically active toxin or active fragment thereof, such as abrin, ricin A, pseudomonas exotoxin or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF") or other growth factors.

Techniques for conjugating such therapeutic moiety to antibodies are well known, see, e.g., Anion et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results and Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985) and Thorpe et al., "The Preparation And Cytotoxic Properties Of Antibody-Toxin Conjugates", Immunol. Rev., 62:119-58 (1982).

Bispecific Molecules

In another aspect, the present disclosure features bispecific molecules comprising an anti-O8E antibody or a fragment thereof, of this disclosure. An antibody of this disclosure or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of this disclosure may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of this disclosure, an antibody of this disclosure can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present disclosure includes bispecific molecules comprising at least one first binding specificity for O8E and a second binding specificity for a second target epitope. In a particular embodiment of this disclosure, the second target epitope is an Fc receptor, e.g., human FcγRI (CD64) or a human Fcα receptor (CD89). Therefore, this disclosure includes bispecific molecules capable of binding both to FcγR or FcαR expressing effector cells (e.g., monocytes, macrophages or polymorphonuclear cells (PMNs)) and to target cells expressing O8E. These bispecific molecules target O8E expressing cells to effector cell and trigger Fc receptor-mediated effector cell activities, such as phagocytosis of an O8E expressing cells, antibody dependent cell-mediated cytotoxicity (ADCC), cytokine release or generation of superoxide anion.

In an embodiment of this disclosure in which the bispecific molecule is multispecific, the molecule can further include a third binding specificity, in addition to an anti-Fc binding specificity and an anti-O8E binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor and thereby results in an enhancement of the effect of the binding determinants for the $F_c$ receptor or target cell antigen. The "anti-enhancement factor portion" can bind an $F_c$ receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g. via CD2, CD3, CD8, CD28, CD4, CD40, ICAM-1 or other immune cell that results in an increased immune response against the target cell).

In one embodiment, the bispecific molecules of this disclosure comprise as a binding specificity at least one antibody or an antibody fragment thereof, including, e.g., an Fab, Fab', F(ab')$_2$, Fv, Fd, dAb or a single chain Fv. The antibody may also be a light chain or heavy chain dimer or any minimal fragment thereof such as a Fv or a single chain construct as described in Ladner et al, U.S. Pat. No. 4,946,778, the contents of which is expressly incorporated by reference.

In one embodiment, the binding specificity for an Fcγ receptor is provided by a monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), FcγRII(CD32) and FcγRIII (CD16). In one preferred embodiment, the Fcγ receptor a human high affinity FcγRI.

The human FcγRI is a 72 kDa molecule, which shows high affinity for monomeric IgG ($10^8$-$10^9 M^{-1}$).

The production and characterization of certain preferred anti-Fcγ monoclonal antibodies are described by Fanger et al. in PCT Publication WO 88/00052 and in U.S. Pat. No. 4,954,617, the teachings of which are fully incorporated by reference herein. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this disclosure are mAb 22, mAb 32, mAb 44, mAb 62 and mAb 197. The hybridoma producing mAb 32 is available from the American Type Culture Collection, ATCC Accession No. HB9469. In other embodiments, the anti-Fcγ receptor antibody is a humanized form of monoclonal antibody 22 (H22). The production and characterization of the H22 antibody is described in Graziano, R. F. et al. (1995) *J Immunol* 155 (10): 4996-5002 and PCT Publication WO 94/10332. The H22 antibody producing cell line was deposited at the American Type Culture Collection under the designation HA022CL1 and has the accession no. CRL 11177.

In still other preferred embodiments, the binding specificity for an Fc receptor is provided by an antibody that binds to a human IgA receptor, e.g., an Fc-alpha receptor (FcαRI (CD89)), the binding of which is typically not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity ($\approx 5\times 10^7 M^{-1}$) for both IgA1 and IgA2, which is increased upon exposure to cytokines such as G-CSF or GM-CSF (Morton, H. C. et al. (1996) *Critical Reviews in Immunology* 16:423-440). Four FcαRI-specific monoclonal antibodies, identified as A3, A59, A62 and A77, which bind FcαRI outside the IgA ligand binding domain, have been described (Monteiro, R. C. et al. (1992). *J. Immunol.* 148: 1764).

FcαRI and FcγRI are preferred trigger receptors for use in the bispecific molecules of this disclosure because they are (1) expressed primarily on immune effector cells, e.g., monocytes, PMNs, macrophages and dendritic cells; (2) expressed at high levels (e.g., 5,000-100,000 per cell); (3) mediators of cytotoxic activities ADCC, phagocytosis); (4) mediate enhanced antigen presentation of antigens, including self-antigens, targeted to them.

While human monoclonal antibodies are preferred, other antibodies that can be employed in the bispecific molecules of this disclosure include, e.g., murine, chimeric and humanized monoclonal antibodies.

The bispecific molecules of the present disclosure can be prepared by conjugating the constituent binding specificities, e.g., the anti-FcR and anti-O8E binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio) propionate (SPDP) and sulfosuccinimidyl 4-(N-maleirnidomethyl)cyclohaxane-1-carboxylate (sulfo-SMCC) (see e.g., Karpovsky et al. (1984) *J. Exp. Med.* 160: 1686; Liu, M A et a (1985) *Proc. Natl. Acad. Sci. USA* 82:8648). Other methods include those described in Paulus (1985) Behring Ins. Mitt. No. 78, 118-132; Brennan et al. (1985) *Science* 229:81-83) and Glennie et al. (1987) *J. Immunol.* 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, typically one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand× Fab fusion protein. A bispecific molecule of this disclosure can be a single chain molecule comprising one single chain antibody and a binding determinant or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (RIA), FACS analysis, bioassay (e.g., growth inhibition) or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

Pharmaceutical Compositions

In another aspect, the present disclosure provides a composition, e.g., a pharmaceutical composition, containing one or a combination of monoclonal antibodies or antigen-binding portion(s) thereof, of the present disclosure, formulated together with a pharmaceutically acceptable carrier. Such compositions may include one or a combination of (e.g., two or more different) antibodies or immunoconjugates or bispecific molecules of this disclosure. For example, a pharmaceutical composition of this disclosure can comprise a combination of antibodies (or immunoconjugates or bispecifics) that bind to different epitopes on the target antigen or that have complementary activities.

Pharmaceutical compositions of this disclosure also can be administered in combination therapy, i.e. combined with other agents. For example, the combination therapy can include an anti-O8E antibody of the present disclosure combined with at least one other anti-inflammatory or immunosuppressant agent. Examples of therapeutic agents that can be used in combination therapy are described in greater detail below in the section on uses of the antibodies of this disclosure.

As used herein, "pharmaceutically acceptable carrier" includes any and all solvents, dispersion media, coatings, antibacterial and antifungal agents, isotonic and absorption delaying agents and the like that are physiologically compatible. Typically, the carrier is suitable for intravenous, intramuscular, subcutaneous, parenteral, spinal or epidermal administration (e.g., by injection or infusion). Depending on the route of administration, the active compound, i.e. antibody, immunoconjugate or bispecific molecule, may be coated in a material to protect the compound from the action of acids and other natural conditions that may inactivate the compound.

The pharmaceutical compounds of this disclosure may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of this disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol and the like; and (3) metal chelating agents, such as citric acid, ethylenediamine tetraacetic acid (EDTA), sorbitol, tartaric acid, phosphoric acid and the like.

Examples of suitable aqueous and nonaqueous carriers that may be employed in the pharmaceutical compositions of this disclosure include water, ethanol, polyols (such as glycerol, propylene glycol, polyethylene glycol and the like) and suitable mixtures thereof, vegetable oils, such as olive oil and injectable organic esters, such as ethyl oleate. Proper fluidity can be maintained, for example, by the use of coating materials, such as lecithin, by the maintenance of the required particle size in the case of dispersions and by the use of surfactants.

These compositions may also contain adjuvants such as preservatives, wetting agents, emulsifying agents and dispersing agents. Prevention of presence of microorganisms may be ensured both by sterilization procedures, supra and by the inclusion of various antibacterial and antifungal agents, for example, paraben, chlorobutanol, phenol sorbic acid and the like. It may also be desirable to include isotonic agents, such as sugars, sodium chloride and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of this disclosure is contemplated. Supplementary active compounds can also be incorporated into the compositions.

Therapeutic compositions typically must be sterile and stable under the conditions of manufacture and storage. The composition can be formulated as a solution, microemulsion, liposome or other ordered structure suitable to high drug concentration. The carrier can be a solvent or dispersion medium containing, for example, water, ethanol, polyol (for example, glycerol, propylene glycol and liquid polyethylene glycol and the like) and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, typically from about 0.1 percent to about 70 percent, most typically from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of this disclosure are dictated by and directly dependent on (a) the unique characteristics of the active compound and the particular therapeutic effect to be achieved and (b) the limitations inherent in the art of compounding such an active compound for the treatment of sensitivity in individuals.

For administration of the antibody, the dosage ranges from about 0.0001 to 100 mg/kg and more usually 0.01 to 25 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. Higher dosages, e.g., 15 mg/kg body weight, 20 mg/kg body weight or 25 mg/kg body weight can be used as needed. An exemplary treatment regime entails administration once per week, once every two weeks, once every three weeks, once every four weeks, once a month, once every 3 months or once every three to 6 months. Particular dosage regimens for an anti-O8E antibody of this disclosure include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more anti-O8E monoclonal antibodies of this disclosure with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

In other methods, one or more anti-O8E monoclonal antibody of this disclosure are administered simultaneously with an antibody having distinct binding specificity such as, for example, anti-CTLA-4 and/or anti-PD-1, in which case the dosage of each antibody administered falls within the ranges indicated.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated and typically until the patient shows partial or complete amelioration of symptoms of disease. Thereafter, the patient can be administered a prophylactic regime.

Actual dosage levels of the active ingredients in the pharmaceutical compositions of the present disclosure may be varied so as to obtain an amount of the active ingredient which is effective to achieve the desired therapeutic response for a particular patient, composition and mode of administration, without being toxic to the patient. The selected dosage level will depend upon a variety of pharmacokinetic factors including the activity of the particular compositions of the present disclosure employed or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated and like factors well known in the medical arts.

A "therapeutically effective dosage" of an anti-O8E antibody of this disclosure typically results in a decrease in severity of disease symptoms, an increase in frequency and duration of disease symptom-free periods or a prevention of impairment or disability due to the disease affliction. For example, for the treatment of O8E+ tumors, a "therapeutically effective dosage" typically inhibits cell growth or tumor growth by at least about 20%, more typically by at least about 40%, even more typically by at least about 60% and still more typically by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size or otherwise ameliorate symptoms in a subject. One of ordinary skill in the art would be able to determine such amounts based on such factors as the subject's size, the severity of the subject's symptoms and the particular composition or route of administration selected.

A composition of the present disclosure can be administered via one or more routes of administration using one or more of a variety of methods known in the art. As will be appreciated by the skilled artisan, the route and/or mode of administration will vary depending upon the desired results. Preferred routes of administration for antibodies of this disclosure include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of this disclosure can be administered via a non-parenteral route, such as a topical, epidermal or mucosal route of administration, for example, intranasally orally, vaginally, rectally, sublingually or topically.

The active compounds can be prepared with carriers that will protect the compound against rapid release, such as a controlled release formulation, including implants, transdermal patches and microencapsulated delivery systems. Biodegradable, biocompatible polymers can be used, such as ethylene vinyl acetate, polyanhydrides, polyglycolic acid, collagen, polyorthoesters and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition of this disclosure can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present disclosure include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems and modules are known to those skilled in the art.

In certain embodiments, the human monoclonal antibodies of this disclosure can be formulated to ensure proper distribution in vivo. For example, the blood-brain barrier (BBB) excludes many highly hydrophilic compounds. To ensure that the therapeutic compounds of this disclosure cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p 120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

Uses and Methods of this Disclosure

The antibodies, particularly the human antibodies, antibody compositions and methods of the present disclosure have numerous in vitro and in vivo diagnostic and therapeutic utilities involving, for example, detection of O8E, treatment of cancer or enhancement of immune response by blockade of O8E. In a preferred embodiment, the antibodies of the present disclosure are human antibodies. For example, these molecules can be administered to cells in culture, in vitro or ex vivo or to human subjects, e.g., in vivo, to treat, prevent and to diagnose a variety of disorders or to enhance immunity in a variety of situations.

As used herein, the term "subject" is intended to include human and non-human animals. The term "non-human animals" includes all vertebrates, e.g., mammals and non-mammals, such as non-human primates, sheep, dogs, cats, cows, horses, chickens, amphibians and reptiles. Preferred subjects include human patients having disorders associated with O8E expression or in need of enhancement of an immune response. The methods are particularly suitable for treating human patients having a disorder associated with aberrant O8E expression. The methods are also particularly suitable for treating human patients having a disorder that can be treated by augmenting the T-cell mediated immune response.

To achieve antigen-specific enhancement of immunity, the anti-O8E antibodies can be administered together with an antigen of interest. When antibodies to O8E are administered together with another agent, the two can be administered in either order or simultaneously.

Given the specific binding of the antibodies of this disclosure for O8E, the antibodies of this disclosure can be used to specifically detect O8E expression on the surface of cells and, moreover, can be used to purify O8E via immunoaffinity purification.

Cancer

O8E is expressed in a variety of human cancers, including breast cell carcinomas, metastatic breast cancers, ovarian cell carcinomas, metastatic ovarian cancers and renal cell carcinomas (Tringler et al. (2005) *Clinical Cancer Res.* 11:1842-48; Salceda et al. (2005) *Exp Cell Res.* 306:128-41; Tringler et al. (2006) *Gynecol Oncol.* 100:44-52; Krambeck et al. (2006) *Proc Natl Acad Sci USA* 103:10391-6; Chen et al. (2006) *Kidney Int. Epub*; Sun et al. (2006) *Lung Cancer* 53:143-51; Bignotti et al. (2006) *Gynecol Oncol.* 103:405-16; Kryczek et al. (2006) *J Exp Med* 203:871-81; Simon et al. (2006) *Cancer Res.* 66:1570-5). An anti-O8E antibody may be used alone to inhibit the growth of cancerous tumors. Alternatively, an anti-O8E antibody may be used in conjunction with other immunogenic agents, standard cancer treatments or other antibodies, as described below.

The B and T lymphocyte attenuator (BTLA) was found to be the receptor for O8E and has an inhibitory effect on immune responses, similar to cytotoxic T lymphocyte antigen-4 (CTLA-4) and programmed death-1 (PD-1) (Carreno and Collins (2003) *Trends Immunol* 24:524-7). O8E functions by negatively regulating T cell immunity by the inhibition of T-cell proliferation, cytokine production and cell cycle production (Choi et al. (2003) *J. Immunol.* 171:4650-4). An O8E-Ig fusion protein inhibits T-cell activation, whereas blockade of O8E by antibodies can enhance the immune response in the patient (Sica et al. (2003) *Immunity* 18:849-61).

In one aspect, the present disclosure relates to treatment of a subject in vivo using an anti-O8E antibody such that growth of cancerous tumors is inhibited. An anti-O8E antibody may be used alone to inhibit the growth of cancerous tumors. Alternatively, an anti-O8E antibody may be used in conjunction with other immunogenic agents, standard cancer treatments or other antibodies, as described below.

Accordingly, in one embodiment, this disclosure provides a method of inhibiting growth of tumor cells in a subject, comprising administering to the subject a therapeutically effective amount of an anti-O8E antibody or antigen-binding portion thereof. Preferably, the antibody is a human anti-O8E antibody (such as any of the human anti-human O8E antibodies described herein). Additionally or alternatively, the antibody may be a chimeric or humanized anti-O8E antibody.

Preferred cancers whose growth may be inhibited using the antibodies of this disclosure include cancers typically responsive to immunotherapy. Non-limiting examples of preferred cancers for treatment include breast cancer (e.g., breast cell carcinoma), ovarian cancer (e.g., ovarian cell carcinoma) and renal cell carcinoma (RCC). Examples of other cancers that may be treated using the methods of this disclosure include melanoma (e.g., metastatic malignant melanoma), prostate cancer, colon cancer, lung cancer, bone cancer, pancreatic cancer, skin cancer, brain tumors, chronic or acute leukemias including acute myeloid leukemia, chronic myeloid leukemia, acute lymphoblastic leukemia, chronic lymphocytic leukemia, lymphomas (e.g., Hodgkin's and non-Hodgkin's lymphoma, lymphocytic lymphoma, primary CNS lymphoma, T-cell lymphoma) nasopharangeal carcinomas, cancer of the head or neck, cutaneous or intraocular malignant melanoma, uterine cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adbreast gland, sarcoma of soft tissue, cancer of the urethra, cancer of the penis, solid tumors of childhood, cancer of the bladder, cancer of the kidney or ureter, carcinoma of the breast pelvis, neoplasm of the central nervous system (CNS), tumor angiogenesis, spinal axis tumor, brain stem glioma, pituitary adenoma, Kaposi's sarcoma, epidermoid cancer, squamous cell cancer, environmentally induced cancers including those induced by asbestos, e.g., mesothelioma and combinations of said cancers.

Optionally, antibodies to O8E can be combined with an immunogenic agent, such as cancerous cells, purified tumor antigens (including recombinant proteins, peptides and carbohydrate molecules), cells and cells transfected with genes encoding immune stimulating cytokines (He et al, *J. Immunol.* 173:4919-28 (2004)). Non-limiting examples of tumor vaccines that can be used include peptides of melanoma antigens, such as peptides of gp100, MAGE antigens, Trp-2, MART1 and/or tyrosinase or tumor cells transfected to express the cytokine GM-CSF.

In humans, some tumors have been shown to be immunogenic such as melanomas. It is anticipated that by raising the threshold of T cell activation by O8E blockade, tumors may be activated in responses in the host.

O8E blockade is likely to be most effective when combined with a vaccination protocol. Many experimental strategies for vaccination against tumors have been devised (see, Rosenberg, "Development of Cancer Vaccines" ASCO Educational Book Spring: 60-62 (2000); Logothetis, ASCO Educational Book Spring: 300-302 (2000); Khayat, ASCO Educational Book Spring: 414-428 (2000); Foon, ASCO Educational Book Spring: 730-738 (2000); see also Restifo and Sznol, Cancer Vaccines, Ch. 61, pp. 3023-3043 in DeVita et al. (ed.) Cancer: Principles and Practice of Oncology, Fifth Edition (1997)). In one of these strategies, a vaccine is prepared using autologous or allogeneic tumor cells. Typically, these cellular vaccines are most effective when the tumor cells are transduced to express GM-CSF. GM-CSF has been shown to be a potent activator of antigen presentation for tumor vaccination (Dranoff et al. *Proc. Natl. Acad. Sci. U.S.A.* 90: 3539-43 (1993)).

The study of gene expression and large scale gene expression patterns in various tumors has led to the definition of so called tumor specific antigens (Rosenberg, *Immunity* 10:281-7 (1999)). In many cases, these tumor specific antigens are differentiation antigens expressed in the tumors and in the cell from which the tumor arose, for example melanocyte antigens gp100, MAGE antigens and Trp-2. More importantly, many of these antigens can be shown to be the targets of tumor specific T cells found in the host. O8E blockade may be used in conjunction with a collection of recombinant proteins and/or peptides expressed in a tumor in order to generate an immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim et al., *Science* 266: 2011-2013 (1994)). (These somatic tissues may be protected from immune attack by various means). Tumor antigen may also be "neo-antigens" expressed in cancer cells because of somatic mutations that alter protein sequence or create fusion proteins between two unrelated sequences (i.e. bcr-abl in the Philadelphia chromosome) or idiotype from B cell tumors.

Other tumor vaccines may include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which may be used in conjunction with O8E blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot and Srivastava *Science* 269: 1585-1588 (1995)); Tamura et al. *Science* 278:117-120 (1997)).

Dendritic cells (DC) are potent antigen presenting cells that can be used to prime antigen-specific responses. DC's can be produced ex vivo and loaded with various protein and peptide antigens as well as tumor cell extracts (Nestle, F. et al. (1998) *Nature Medicine* 4: 328-332). DCs may also be transduced by genetic means to express these tumor antigens as well. DCs have also been fused directly to tumor cells for the purposes of immunization (Kugler, A. et al. (2000) *Nature Medicine* 6:332-336). As a method of vaccination, DC immunization may be effectively combined with PD-1 blockade to activate more potent anti-tumor responses.

O8E blockade may also be combined with standard cancer treatments. O8E blockade may be effectively combined with chemotherapeutic regimes. In these instances, it may be possible to reduce the dose of chemotherapeutic reagent administered (Mokyr, M. et al. (1998) *Cancer Research* 58: 5301-5304). An example of such a combination is an anti-O8E antibody in combination with decarbazine for the treatment of various cancers. Another example of such a combination is an anti-O8E antibody in combination with interleukin-2 (IL-2) for the treatment of various cancers. The scientific rationale behind the combined use of O8E blockade and chemotherapy is that cell death, that is a consequence of the cytotoxic action of most chemotherapeutic compounds, should result in increased levels of tumor antigen in the antigen presentation pathway. Other combination therapies that may result in synergy with O8E blockade through cell death are radiation, surgery and hormone deprivation. Each of these protocols creates a source of tumor antigen in the host. Angiogenesis inhibitors may also be combined with O8E blockade. Inhibition of angiogenesis leads to tumor cell death which may feed tumor antigen into host antigen presentation pathways.

O8E blocking antibodies can also be used in combination with bispecific antibodies that target Fc alpha or Fc gamma receptor-expressing effectors cells to tumor cells (see, e.g., U.S. Pat. Nos. 5,922,845 and 5,837,243). Bispecific antibodies can be used to target two separate antigens. For example anti-Fc receptor/anti tumor antigen (e.g., Her-2/neu) bispecific antibodies have been used to target macrophages to sites of tumor. This targeting may more effectively activate tumor specific responses. The T cell arm of these responses would by augmented by the use of O8E blockade. Alternatively, antigen may be delivered directly to DCs by the use of bispecific antibodies which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-beta (Kehrl, J. et al. (1986) *J. Exp. Med.*

163: 1037-1050), IL-10 (Howard, M. & O'Garra, A. (1992) *Immunology Today* 13: 198-200) and Fas ligand (Hahne, M. et al. (1996) *Science* 274: 1363-1365). Antibodies to each of these entities may be used in combination with anti-PD-1 to counteract the effects of the immunosuppressive agent and favor tumor immune responses by the host.

Other antibodies which may be used to activate host immune responsiveness can be used in combination with anti-O8E. These include molecules on the surface of dendritic cells which activate DC function and antigen presentation. Anti-CD40 antibodies are able to substitute effectively for T cell helper activity (Ridge, J. et al. (1998) Nature 393: 474-478) and can be used in conjunction with O8E antibodies. Activating antibodies to T cell costimulatory molecules such as CTLA-4 (e.g., U.S. Pat. No. 5,811,097), OX-40 (Weinberg, A. et al. (2000) *Immunol* 164: 2160-2169), 4-1BB (Melero, I. et al. (1997) *Nature Medicine* 3: 682-685 (1997), PD-1 (del Rio et al. (2005) *Eur J. Immunol.* 35:3545-60) and ICOS (Hutloff, A. et al. (1999) *Nature* 397: 262-266) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. O8E, blockade can be used to increase the effectiveness of the donor engrafted tumor specific T cells.

There are also several experimental treatment protocols that involve ex vivo activation and expansion of antigen specific T cells and adoptive transfer of these cells into recipients in order to antigen-specific T cells against tumor (Greenberg, R. & Riddell, S. (1999) *Science* 285: 546-51). These methods may also be used to activate T cell responses to infectious agents such as CMV. Ex vivo activation in the presence of anti-O8E antibodies may be expected to increase the frequency and activity of the adoptively transferred T cells.

Given the expression of O8E on various tumor cells, the human antibodies, antibody compositions and methods of the present disclosure can be used to treat a subject with a tumorigenic disorder, e.g., a disorder characterized by the presence of tumor cells expressing O8E including, for example, breast cancer (e.g., breast cell carcinoma), ovarian cancer (e.g., ovarian cell carcinoma), and renal cancer. Examples of other cancers that may be treated using the methods of the instant disclosure include melanoma (e.g., metastatic malignant melanoma), prostate cancer, colon cancer and lung cancer, bone cancer, pancreatic cancer, skin cancer, cancer of the head or neck, cutaneous or intraocular malignant melanoma, uterine cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, acute lymphocytic leukemia (ALL), chronic lymphocytic leukemia (CLL), Burkitt's lymphoma, anaplastic large-cell lymphomas (ALCL), multiple myeloma, cutaneous T-cell lymphomas; nodular small cleaved-cell lymphomas, lymphocytic lymphomas, peripheral T-cell lymphomas, Lennert's lymphomas, immunoblastic lymphomas, T-cell leukemia/lymphomas (ATLL), adult T-cell leukemia (T-ALL), entroblastic/centrocytic (cb/cc) follicular lymphomas cancers, diffuse large cell lymphomas of B lineage, angioimmunoblastic lymphadenopathy (AILD)-like T cell lymphoma, HIV associated body cavity based lymphomas, embryonal carcinomas, undifferentiated carcinomas of the rhino-pharynx (e.g., Schmincke's tumor), Castleman's disease, Kaposi's Sarcoma, multiple myeloma, Waldenstrom's macroglobulinemia and other B-cell lymphomas, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, glioblastoma, brain tumors, nasopharangeal carcinomas, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present disclosure is also useful for treatment of metastatic cancers.

Accordingly, in one embodiment, this disclosure provides a method of inhibiting growth of tumor cells in a subject, comprising administering to the subject a therapeutically effective amount of an anti-O8E antibody or antigen-binding portion thereof. Typically, the antibody is a human anti-O8E antibody (such as any of the human anti-human O8E antibodies described herein). Additionally or alternatively, the antibody may be a chimeric or humanized anti-O8E antibody.

Infectious Diseases

Other methods of this disclosure are used to treat patients that have been exposed to particular toxins or pathogens. Accordingly, another aspect of this disclosure provides a method of treating an infectious disease in a subject comprising administering to the subject an anti-O8E antibody or antigen-binding portion thereof, such that the subject is treated for the infectious disease. Preferably, the antibody is a human anti-human O8E antibody (such as any of the human anti-O8E antibodies described herein). Additionally or alternatively, the antibody can be a chimeric or humanized antibody.

Similar to its application to tumors as discussed above, antibody mediated O8E blockade can be used alone or as an adjuvant, in combination with vaccines, to stimulate the immune response to pathogens, toxins and self-antigens. Examples of pathogens for which this therapeutic approach may be particularly useful, include pathogens for which there is currently no effective vaccine or pathogens for which conventional vaccines are less than completely effective. These include, but are not limited to HIV, Hepatitis (A, B, & C), Influenza, Herpes, *Giardia, Malaria, Leishmania, Staphylococcus aureus, Pseudomonas aeruginosa*. PD-1 blockade is particularly useful against established infections by agents such as HIV that present altered antigens over the course of the infections. These novel epitopes are recognized as foreign at the time of anti-human O8E administration, thus provoking a strong T cell response that is not dampened by negative signals through O8E.

Some examples of pathogenic viruses causing infections treatable by methods of this disclosure include HIV, hepatitis (A, B or C), herpes virus (e.g., VZV, HSV-1, HAV-6, HSV-II and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of this disclosure include chlamydia, rickettsial bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis and Lynxes disease bacteria.

Some examples of pathogenic fungi causing infections treatable by methods of this disclosure include *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum*.

Some examples of pathogenic parasites causing infections treatable by methods of this disclosure include *Entamoeba histolytica Balantidium coli, Naegleriafowleri, Acanthamoeba* sp., *Giardia larnbia, Cryptosporidium* sp., *Pneumocystis carinii, Plasmodium vivax, Babesia microti, Trypanosoma brucei, Trypanosoma cruzi, Leishmania donovani, Toxoplasma gondi, Nippostrongylus brasiliensis*.

In all of the above methods, O8E blockade can be combined with other forms of immunotherapy such as cytokine treatment (e.g., interferons, GM-CSF, G-CSF, IL-2) or bispecific antibody therapy, which provides for enhanced presentation of tumor antigens (see, e.g., Holliger (1993) *Proc. Natl. Acad. Sci. USA* 90:6444-6448; Poljak (1994) *Structure* 2:1121-1123).

Autoimmune Reactions

Anti-O8E antibodies may provoke and amplify autoimmune responses. Indeed, induction of anti-tumor responses using tumor cell and peptide vaccines reveals that many anti-tumor responses involve anti-self reactivities (depigmentation observed in anti-CTLA-4+GM-CSF-modified B16 melanoma in van Elsas et al. supra; depigmentation in Trp-2 vaccinated mice (Overwijk, W. et al. (1999) *Proc. Natl. Acad. Sci. U.S.A.* 96: 2982-2987); autoimmune prostatitis evoked by TRAMP tumor cell vaccines (Hurwitz, A. (2000) supra), melanoma peptide antigen vaccination and vitilago observed in human clinical trials (Rosenberg, S A and White, D E (1996) *J. Immunother Emphasis Tumor Immunol* 19 (1): 81-4).

Therefore, it is possible to consider using anti-O8E blockade in conjunction with various self proteins in order to devise vaccination protocols to efficiently generate immune responses against these self proteins for disease treatment. For example, Alzheimers disease involves inappropriate accumulation of Aβ peptide in amyloid deposits in the brain; antibody responses against amyloid are able to clear these amyloid deposits (Schenk et al., (1999) *Nature* 400:173-177).

Other self proteins may also be used as targets such as IgE for the treatment of allergy and asthma and TNFα for rheumatoid arthritis. Finally, antibody responses to various hormones may be induced by the use of anti-O8E antibody. Neutralizing antibody responses to reproductive hormones may be used for contraception. Neutralizing antibody response to hormones and other soluble factors that are required for the growth of particular tumors may also be considered as possible vaccination targets.

Analogous methods as described above for the use of anti-O8E antibody can be used for induction of therapeutic autoimmune responses to treat patients having an inappropriate accumulation of other self-antigens, such as amyloid deposits, including Aβ in Alzheimer's disease, cytokines such as TNFα and IgE.

Vaccines

Anti-O8E antibodies may be used to stimulate antigen-specific immune responses by coadministration of an anti-O8E antibody with an antigen of interest (e.g., a vaccine). Accordingly, in another aspect this disclosure provides a method of enhancing an immune response to an antigen in a subject, comprising administering to the subject: (i) the antigen; and (ii) an anti-O8E antibody or antigen-binding portion thereof, such that an immune response to the antigen in the subject is enhanced. Preferably, the antibody is a human anti-human O8E antibody (such as any of the human anti-O8E antibodies described herein). Additionally or alternatively, the antibody can be a chimeric or humanized antibody. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above or antigens from the viruses, bacteria or other pathogens described above.

Suitable routes of administering the antibody compositions (e.g., human monoclonal antibodies, multispecific and bispecific molecules and immunoconjugates) of this disclosure in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

As previously described, human anti-O8E antibodies of this disclosure can be co-administered with one or other more therapeutic agents, e.g., a cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, decarbazine and cyclophosphamide hydroxyurea which, by themselves, are only effective at levels which are toxic or subtoxic to a patient. Cisplatin is intravenously administered as a 100 mg/dose once every four weeks and adriamycin is intravenously administered as a 60-75 mg/ml dose once every 21 days. Co-administration of the human anti-O8E antibodies or antigen binding fragments thereof, of the present disclosure with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Also within the scope of the present disclosure are kits comprising the antibody compositions of this disclosure (e.g., human antibodies, bispecific or multispecific molecules or immunoconjugates) and instructions for use. The kit can further contain a least one additional reagent or one or more additional human antibodies of this disclosure (e.g., a human antibody having a complementary activity which binds to an epitope in O8E antigen distinct from the first human antibody). Kits typically include a label indicating the intended use of the contents of the kit. The term label includes any writing or recorded material supplied on or with the kit or which otherwise accompanies the kit.

Combination Therapy

In one embodiment, the present disclosure provides a method for treating a hyperproliferative disease, comprising administering an O8E antibody and a CTLA-4 and/or PD-1 antibody to a subject. In further embodiments, the anti-O8E antibody is administered at a subtherapeutic dose, the anti- CTLA-4 and/or PD-1 antibody is administered at a subtherapeutic dose or both are administered at a subtherapeutic dose. In another embodiment, the present disclosure provides a method for altering an adverse event associated with treatment of a hyperproliferative disease with an immunostimulatory agent, comprising administering an anti-O8E antibody and a subtherapeutic dose of anti-CTLA-4 and/or anti-PD-1 antibody to a subject. In certain embodiments, the subject is human. In certain embodiments, the anti-CTLA-4 antibody is human sequence monoclonal antibody 10D1 and the anti-PD-1 antibody is human sequence monoclonal antibody, such as 17D8, 2D3, 4H1, 5C4 and 4A11. Human sequence monoclonal antibody 10D1 has been isolated and structurally characterized, as described in U.S. Pat. No. 6,984,720. Human sequence monoclonal antibodies 17D8, 2133, 4H1, 5C4 and 4A11 have been isolated and structurally characterized, as described in U.S. Provisional Patent No. 60/679,466.

The anti-O8E, anti-CTLA-4 antibody and anti-PD-1 monoclonal antibodies (mAbs) and the human sequence antibodies of this disclosure can be produced by a variety of techniques, including conventional monoclonal antibody methodology, e.g., the standard somatic cell hybridization technique of Kohler and Milstein (1975) *Nature* 256:495. Any technique for producing monoclonal antibody can be employed, e.g., viral or oncogenic transformation of B lymphocytes, One animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known (see, e.g., Harlow and Lane (1988) *Antibodies, A Laboratory Manual*, Cold Spring Harbor Laboratory Press, Cold Spring Harbor N.Y.).

The combination of antibodies is useful for enhancement of an immune response against a hyperproliferative disease by blockade of O8E and PD-1 and/or CTLA-4. In a preferred embodiment, the antibodies of the present disclosure are human antibodies. For example, these molecules can be administered to cells in culture, in vitro or ex vivo or to human subjects, e.g., in vivo, to enhance immunity in a variety of situations. Accordingly, in one aspect, this disclosure provides a method of modifying an immune response in a subject comprising administering to the subject an antibody combination or a combination of antigen-binding portions thereof, of this disclosure such that the immune response in the subject is modified. Preferably, the response is enhanced, stimulated or up-regulated. In another embodiment, the instant disclosure provides a method of altering adverse events associated with treatment of a hyperproliferative disease with an immunostimulatory therapeutic agent, comprising administering an anti-O8E antibody and a subtherapeutic dose of anti-CTLA-4 or anti-PD-1 antibody to a subject.

Blockade of O8E, PD-1 and CTLA-4 by antibodies can enhance the immune response to cancerous cells in the patient. Cancers whose growth may be inhibited using the antibodies of the instant disclosure include cancers typically responsive to immunotherapy. Representative examples of cancers for treatment with the combination therapy of the instant disclosure include melanoma (e.g., metastatic malignant melanoma), renal cancer, prostate cancer, breast cancer, colon cancer and lung cancer. Examples of other cancers that may be treated using the methods of the instant disclosure include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos and combinations of said cancers. The present disclosure is also useful for treatment of metastatic cancers.

In certain embodiments, the combination of therapeutic antibodies discussed herein may be administered concurrently as a single composition in a pharmaceutically acceptable carrier or concurrently as separate compositions with each antibody in a pharmaceutically acceptable carrier. In another embodiment, the combination of therapeutic antibodies can be administered sequentially. For example, an anti-O8E antibody and an anti-PD-1 antibody can be administered sequentially, such as anti-O8E being administered first and anti-PD-1 second or anti-PD-1 being administered first and anti-O8E second. Furthermore, if more than one dose of the combination therapy is administered sequentially, the order of the sequential administration can be reversed or kept in the same order at each time point of administration, sequential administrations may be combined with concurrent administrations or any combination thereof. For example, the first administration of a combination anti-O8E antibody and anti-PD-1 antibody may be concurrent, the second administration may be sequential with anti-O8E first and anti-PD-1 second and the third administration may be sequential with anti-PD-1 first and anti-O8E second, etc. Another representative dosing scheme may involve a first administration that is sequential with anti-PD-1 first and anti-O8E second and subsequent administrations may be concurrent.

Optionally, the combination of anti-O8E and anti-CTLA-4 and/or anti-PD-1 antibodies can be further combined with an immunogenic agent, such as cancerous cells, purified tumor antigens (including recombinant proteins, peptides and carbohydrate molecules), cells and cells transfected with genes encoding immune stimulating cytokines (He et al. (2004) *J. Immunol.* 173:4919-28). Non-limiting examples of tumor vaccines that can be used include peptides of melanoma antigens, such as peptides of gp100, MAGE antigens, Trp-2, MART1 and/or tyrosinase or tumor cells transfected to express the cytokine GM-CSF (discussed further below).

A combined O8E and PD-1 and/or CTLA-4 blockade can be further combined with a vaccination protocol. Many experimental strategies for vaccination against tumors have been devised (see Rosenberg, S. (2000) Development of Cancer Vaccines, ASCO Educational Book Spring: 60-62; Logothetis, C., 2000, ASCO Educational Book Spring: 300-302; Khayat, D. (2000) ASCO Educational Book Spring: 414-428; Foon, K. (2000) ASCO Educational Book Spring: 730-738; see also Restifo and Sznol, Cancer Vaccines, Ch. 61, pp. 3023-3043 in DeVita et al. (eds.), 1997, Cancer: Principles and Practice of Oncology. Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci U.S.A.* 90: 3539-43).

The study of gene expression and large scale gene expression patterns in various tumors has led to the definition of so called tumor specific antigens (Rosenberg (1999) Immunity 10:281-7). In many cases, these tumor specific antigens are differentiation antigens expressed in the tumors and in the cell from which the tumor arose, for example melanocyte antigens gp100, MAGE antigens and Trp-2. More importantly, many of these antigens can be shown to be the targets of tumor specific T cells found in the host. In certain embodiments, a combined O8E and PD-1 and/or CTLA-4 blockade using the antibody compositions described herein may be used in conjunction with a collection of recombinant proteins and/or peptides expressed in a tumor in order to generate an immune response to these proteins. These proteins are normally viewed by the immune system as self-antigens and are, therefore, tolerant to them. The tumor antigen may also include the protein telomerase, which is required for the synthesis of telomeres of chromosomes and which is expressed in more than 85% of human cancers and in only a limited number of somatic tissues (Kim et al. (1994) *Science* 266: 2011-2013). (These somatic tissues may be protected from immune attack by various means). Tumor antigen may also be "neo-antigens" expressed in cancer cells because of somatic mutations that alter protein sequence or create fusion proteins between two unrelated sequences bcr-abl in the Philadelphia chromosome) or idiotype from B cell tumors.

Other tumor vaccines may include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which may be used in conjunction with O8E blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Snot & Srivastava (1995) *Science* 269:1585-1588; Tamura et al. (1997) *Science* 278:117-120).

Dendritic cells (DC) are potent antigen presenting cells that can be used to prime antigen-specific responses. DC's can be produced ex viva and loaded with various protein and peptide antigens as well as tumor cell extracts (Nestle et al. (1998) *Nature Medicine* 4: 328-332). DCs may also be transduced by genetic means to express these tumor antigens as well. DCs have also been fused directly to tumor cells for the purposes of immunization (Kugler et al. (2000) *Nature Medicine* 6:332-336). As a method of vaccination, DC immunization may be effectively further combined with a combined O8E and PD-1 and/or CTLA-4 blockade to activate more potent anti-tumor responses.

A combined O8E and PD-1 and/or CTLA-4 blockade may also be further combined with standard cancer treatments. For example, a combined O8E and PD-1 and/or CTLA-4 blockade may be effectively combined with chemotherapeutic regimes. In these instances, as is observed with the combination of anti-O8E and anti-CTLA-4 and/or anti-PD-1 antibodies, it may be possible to reduce the dose of other chemotherapeutic reagent administered with the combination of the instant disclosure (Mokyr et al. (1998) *Cancer Research* 58: 5301-5304). The scientific rationale behind the combined use of O8E and PD-1 and/or CTLA-4 blockade with chemotherapy is that cell death, which is a consequence of the cytotoxic action of most chemotherapeutic compounds, should result in increased levels of tumor antigen in the antigen presentation pathway. Other combination therapies that may result in synergy with a combined O8E and PD-1 and/or CTLA-4 blockade through cell death include radiation, surgery or hormone deprivation. Each of these protocols creates a source of tumor antigen in the host. Angiogenesis inhibitors may also be combined with a combined O8E and PD-1 and/or CTLA-4 blockade. Inhibition of angiogenesis leads to tumor cell death, which may also be a source of tumor antigen to be fed into host antigen presentation pathways.

A combination of O8E and PD-1 and/or CTLA-4 blocking antibodies can also be used in combination with bispecific antibodies that target Fcα or Fcγ receptor-expressing effector cells to tumor cells (see, e.g., U.S. Pat. Nos. 5,922,845 and 5,837,243). Bispecific antibodies can be used to target two separate antigens. For example anti-Fc receptor/anti tumor antigen (e.g., Her-2/neu) bispecific antibodies have been used to target macrophages to sites of tumor. This targeting may more effectively activate tumor specific responses. The T cell arm of these responses would by augmented by the use of a combined O8E and PD-1 and/or CTLA-4 blockade. Alternatively, antigen may be delivered directly to DCs by the use of bispecific antibodies which bind to tumor antigen and a dendritic cell specific cell surface marker.

In another example, a combination of anti-PD-1 and anti-CTLA-4 antibodies can be used in conjunction with anti-neoplastic antibodies, such as Rituxan® (rituximab), Herceptin® (trastuzumab), Bexxar® (tositumomab), Zevalin® (ibritimiomab), Campath® (alemtuzumab), Lymphocide® (eprtuzumab), Avastin® (bevacizurnab) and Tarceva® (erlotinib) and the like. By way of example and not wishing to be bound by theory, treatment with an anti-cancer antibody or an anti-cancer antibody conjugated to a toxin can lead to cancer cell death (e.g., tumor cells) which would potentiate an immune response mediated by O8E, CTLA-4 or PD-1. In an exemplary embodiment, a treatment of a hyperproliferative disease (e.g., a cancer tumor) may include an anti-cancer antibody in combination with anti-O8E and anti-PD-1 and/or anti-CTLA-4 antibodies, concurrently or sequentially or any combination thereof, which may potentiate an anti-tumor immune responses by the host.

Tumors evade host immune surveillance by a large variety of mechanisms. Many of these mechanisms may be overcome by the inactivation of proteins, which are expressed by the tumors and which are immunosuppressive. These include, among others, TGF-β (Kehrl, J. et al. (1986) *J. Exp. Med.* 163: 1037-1050), IL-10 (Howard, M. & O'Garra, A. (1992) *Immunology Today* 13: 198-200) and Fas ligand (Hahne, M. et al. (1996) *Science* 274: 1363-1365). In another example, antibodies to each of these entities may be further combined with an anti-O8E and anti-PD-1 and/or anti-CTLA-4 combination to counteract the effects of immunosuppressive agents and favor anti-tumor immune responses by the host.

Other antibodies that may be used to activate host immune responsiveness can be further used in combination with an anti-O8E and anti-PD-1 and/or anti-CTLA-4 combination. These include molecules on the surface of dendritic cells that activate DC function and antigen presentation. Anti-CD40 antibodies are able to substitute effectively for T cell helper activity (Ridge, J. et al. (1998) Nature 393: 474-478) and have been shown efficacious in conjunction with anti-CTLA-4 (Ito, N. et al. (2000) *Immunobiology* 201 (5) 527-40). Activating antibodies to T cell costimulatory molecules, such as OX-40 (Weinberg, A. et al, (2000) *Immunol* 164: 2160-2169), 4-1BB (Melero, I. et al. (1997) *Nature Medicine* 3: 682-685 (1997), PD-1 (del Rio et al. (2005) *Eur J Immunol.* 35:3545-60) and ICOS (Hutloff, A. et al. (1999) *Nature* 397: 262-266) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. A combined O8E and PD-1 and/or CTLA-4 blockade can be used to increase the effectiveness of the donor engrafted tumor specific T cells.

There are also several experimental treatment protocols that involve ex vivo activation and expansion of antigen specific T cells and adoptive transfer of these cells into recipients in order to antigen-specific T cells against tumor (Greenberg, R. & Riddell, S. (1999) *Science* 285: 546-51). These methods may also be used to activate T cell responses to infectious agents such as CMV. Ex vivo activation in the presence of anti-O8E and anti-PD-1 and/or anti-CTLA-4 antibodies may be expected to increase the frequency and activity of the adoptively transferred T cells.

As set forth herein organs can exhibit immune-related adverse events following immunostimulatory therapeutic antibody therapy, such as the GI tract (diarrhea and colitis) and the skin (rash and pruritis) after treatment with anti-CTLA-4 antibody. For example, non-colonic gastrointestinal immune-related adverse events have also been observed in the esophagus (esophagitis), duodenum (duodenitis) and ileum (ileitis) after anti-CTLA-4 antibody treatment.

In certain embodiments, the present disclosure provides a method for altering an adverse event associated with treatment of a hyperproliferative disease with an immunostimulatory agent, comprising administering a anti-O8E antibody and a subtherapeutic dose of anti-CTLA-4 antibody to a subject. For example, the methods of the present disclosure provide for a method of reducing the incidence of immunostimulatory therapeutic antibody-induced colitis or diarrhea by administering a non-absorbable steroid to the patient. Because any patient who will receive an immunostimulatory therapeutic antibody is at risk for developing colitis or diarrhea induced by such an antibody, this entire patient population is suitable for therapy according to the methods of the present disclosure. Although steroids have been administered to treat inflammatory bowel disease (IBD) and prevent exacerbations of IBD, they have not been used to prevent (decrease the incidence of) IBD in patients who have not been diagnosed with IBD. The significant side effects associated with steroids, even non-absorbable steroids, have discouraged prophylactic use.

In further embodiments, a combination O8E and PD-1 and/or CTLA-4 blockade (i.e., immunostimulatory therapeutic antibodies anti-O8E and anti-PD-1 and/or anti-CTLA-4) can be further combined with the use of any non-absorbable steroid. As used herein, a "non-absorbable steroid" is a glucocorticoid that exhibits extensive first pass metabolism such that, following metabolism in the liver, the bioavailability of the steroid is low, i.e., less than about 20%. In one embodiment of this disclosure, the non-absorbable steroid is budesonide. Budesonide is a locally-acting glucocorticosteroid, which is extensively metabolized, primarily by the liver, following oral administration. ENTOCORT EC® (Astra-Zeneca) is a pH- and time-dependent oral formulation of budesonide developed to optimize drug delivery to the ileum and throughout the colon. ENTOCORT EC® is approved in the U.S. for the treatment of mild to moderate Crohn's disease involving the ileum and/or ascending colon. The usual oral dosage of ENTOCORT EC® for the treatment of Crohn's disease is 6 to 9 mg/day. ENTOCORT EC® is released in the intestines before being absorbed and retained in the gut mucosa. Once it passes through the gut mucosa target tissue, ENTOCORT EC® is extensively metabolized by the cytochrome P450 system in the liver to metabolites with negligible glucocorticoid activity. Therefore, the bioavailability is low (about 10%). The low bioavailability of budesonide results in an improved therapeutic ratio compared to other glucocorticoids with less extensive first-pass metabolism. Budesonide results in fewer adverse effects, including less hypothalamic-pituitary suppression, than systemically-acting corticosteroids. However, chronic administration of ENTOCORT EC® can result in systemic glucocorticoid effects such as hypercorticism and adrenal suppression. See PDR 58$^{th}$ ed. 2004; 608-610.

In still further embodiments, a combination O8E and PD-1 and/or CTLA-4 blockade (i.e., immunostimulatory therapeutic antibodies anti-O8E and anti-PD-1 and/or anti-CTLA-4) in conjunction with a non-absorbable steroid can be further combined with a salicylate. Salicylates include 5-ASA agents such as, for example: sulfasalazine (AZULFIDINE®, Pharmacia & Upjohn); olsalazine (DIPENTUM®, Pharmacia & Upjohn); balsalazide (COLAZAL®, Salix Pharmaceuticals, Inc.); and mesalamine (ASACOL®, Procter & Gamble Pharmaceuticals; PENTASA®, Shire US; CANASA®, Axcan Scandipharm, Inc.; ROWASA®, Solvay).

In accordance with the methods of the present disclosure, a salicylate administered in combination with anti-O8E and anti-PD-1 and/or anti-CTLA-4 antibodies and a non-absorbable steroid can includes any overlapping or sequential administration of the salicylate and the non-absorbable steroid for the purpose of decreasing the incidence of colitis induced by the immunostimulatory antibodies. Thus, for example, methods for reducing the incidence of colitis induced by the immunostimulatory antibodies according to the present disclosure encompass administering a salicylate and a non-absorbable concurrently or sequentially (e.g., a salicylate is administered 6 hours after a non-absorbable steroid) or any combination thereof. Further, according to the present disclosure, a salicylate and a non-absorbable steroid can be administered by the same route (e.g., both are administered orally) or by different routes (e.g., a salicylate is administered orally and a non-absorbable steroid is administered rectally), which may differ from the route(s) used to administer the anti-O8E, anti-PD-1 and anti-CTLA-4 antibodies.

The compositions (e.g., human antibodies, multispecific and bispecific molecules and immunoconjugates) of this disclosure which have complement binding sites, such as portions from IgG1, -2 or -3 or IgM which bind complement, can also be used in the presence of complement. In one embodiment, ex vivo treatment of a population of cells comprising target cells with a binding agent of this disclosure and appropriate effector cells can be supplemented by the addition of complement or serum containing complement. Phagocytosis of target cells coated with a binding agent of this disclosure can be improved by binding of complement proteins. In another embodiment target cells coated with the compositions (e.g., human antibodies, multispecific and bispecific molecules) of this disclosure can also be lysed by complement. In yet another embodiment, the compositions of this disclosure do not activate complement.

The compositions (e.g., human antibodies, multispecific and bispecific molecules and immunoconjugates) of this disclosure can also be administered together with complement. Accordingly, within the scope of this disclosure are compositions comprising human antibodies, multispecific or bispecific molecules and serum or complement. These compositions are advantageous in that the complement is located in close proximity to the human antibodies, multispecific or bispecific molecules. Alternatively, the human antibodies, multispecific or bispecific molecules of this disclosure and the complement or serum can be administered separately.

Accordingly, patients treated with antibody compositions of this disclosure can be additionally administered (prior to, simultaneously with or following administration of a human antibody of this disclosure) with another therapeutic agent, such as a cytotoxic or radiotoxic agent, which enhances or augments the therapeutic effect of the human antibodies.

In other embodiments, the subject can be additionally treated with an agent that modulates, e.g., enhances or inhibits, the expression or activity of Fcγ or Fcγ receptors by, for example, treating the subject with a cytokine. Preferred cytokines for administration during treatment with the multispecific molecule include of granulocyte colony-stimulating factor (G-CSF), granulocyte-macrophage colony-stimulating factor (GM-CSF), interferon-γ (IFN-γ) and tumor necrosis factor (TNF).

The compositions (e.g., human antibodies, multispecific and bispecific molecules) of this disclosure can also be used to target cells expressing FcγR or O8E, for example for labeling such cells. For such use, the binding agent can be linked to a molecule that can be detected. Thus, this disclosure provides methods for localizing ex vivo or in vitro cells expressing Fc receptors, such as FcγR or O8E. The detectable label can be, e.g., a radioisotope, a fluorescent compound, an enzyme or an enzyme co-factor.

In a particular embodiment, this disclosure provides methods for detecting the presence of O8E antigen in a sample or measuring the amount of O8E antigen, comprising contacting the sample and a control sample, with a human monoclonal antibody or an antigen binding portion thereof, which specifically binds to O8E, under conditions that allow for formation of a complex between the antibody or portion thereof and O8E. The formation of a complex is then detected, wherein a difference complex formation between the sample compared to the control sample is indicative the presence of O8E antigen in the sample.

In other embodiments, this disclosure provides methods for treating a O8E mediated disorder in a subject.

In yet another embodiment, immunoconjugates of this disclosure can be used to target compounds (e.g., therapeutic agents, labels, cytotoxins, radiotoxins immunosuppressants, etc.) to cells which have O8E cell surface receptors by linking such compounds to the antibody. For example, an anti-O8E antibody can be conjugated to UPT, as described in U.S. patent application Ser. Nos. 10/160,972, 10/161,233, 10/161,234, 11/134,826, 11/134,685 and U.S. Provisional Patent Application No. 60/720,499 and/or any of the toxin compounds described in U.S. Pat. Nos. 6,281,354 and 6,548,530, US patent publication Nos. 20030050331, 20030064984, 20030073852 and 20040087497 or published in WO 03/022806, which are hereby incorporated by reference in their entireties. Thus, this disclosure also provides methods for localizing ex vivo or in vivo cells expressing O8E (e.g., with a detectable label, such as a radioisotope, a fluorescent compound, an enzyme or an enzyme co-factor). Alternatively, the immunoconjugates can be used to kill cells which have O8E cell surface receptors by targeting cytotoxins or radiotoxins to O8E.

The present disclosure is further illustrated by the following examples which should not be construed as further limiting. The contents of all figures and all references, patents and published patent applications cited throughout this application are expressly incorporated herein by reference.

EXAMPLES

Example 1

Generation of Human Monoclonal Antibodies Against O8E

This Example discloses the generation of human monoclonal antibodies that specifically bind to human O8E (a/k/a B7H4, B7S1 and B7x).

Antigen

CHO and HEK-293 cells were transfected with O8E using standard recombinant transfection methods and used as antigen for immunization. In addition, recombinant O8E alone was also used as antigen for immunization.

Transgenic HuMAb Mouse® and KM Mouse®

Fully human monoclonal antibodies to O8E were prepared using the HCo7 and HCo12 strains of the transgenic HuMAb Mouse® and the KM strain of transgenic transchromosomic mice, each of which express human antibody genes. In each of these mouse strains, the endogenous mouse kappa light chain gene has been homozygously disrupted as described in Chen et al. (1993) EMBO J. 12:811-820 and the endogenous mouse heavy chain gene has been homozygously disrupted as described in Example 1 of PCT Publication WO 01/09187. Each of these mouse strains carries a human kappa light chain transgene, KCo5, as described in Fishwild et al. (1996) Nature Biotechnology 14:845-851. The HCo7 strain carries the HCo7 human heavy chain transgene as described in U.S. Pat. Nos. 5,545,806; 5,625,825; and 5,545,807. The HCo12 strain carries the HCo12 human heavy chain transgene as described in Example 2 of PCT Publication WO 01/09187. The KM Mouse® strain contains the SC20 transchromosome as described in PCT Publication WO 02/43478.

HuMAb and KM Immunizations:

To generate fully human monoclonal antibodies to O8E, mice of the HuMAb Mouse® and KM Mouse® were immunized with CHO-O8E transfected cells, HEK293-O8E transfected cells and/or purified recombinant O8E protein. General immunization schemes for HuMAb Mouse® are described in Lonberg, N. et al (1994) Nature 368(6474):856-859; Fishwild, D. et al. (1996) Nature Biotechnology 14:845-851 and PCT Publication WO 98/24884. The mice were 6-16 weeks of age upon the first infusion of antigen. A purified recombinant preparation (5-50 μg) of O8E protein was used to immunize the HuMAb Mice™ and KM Mice™.

Transgenic mice were immunized twice with antigen in complete Freund's adjuvant adjuvant either intraperitonealy (IP) or subcutaneously (Sc), followed by 3-21 days IP or SC immunization (up to a total of 11 immunizations) with the antigen in incomplete Freund's adjuvant. The immune response was monitored by retroorbital bleeds. The plasma was screened by ELISA (as described below) and mice with sufficient titers of anti-O8E human immunoglobulin were used for fusions. Mice were boosted intravenously with antigen 3 and 2 days before sacrifice and removal of the spleen. Typically, 10-35 fusions for each antigen were performed. Several dozen mice were immunized for each antigen.

Selection of HuMb Mice™ or KM Mice™ Producing Anti-O8E Antibodies:

To select HuMab Mice™ or KM Mice™ producing antibodies that bound O8E sera from immunized mice was tested by ELISA as described by Fishwild, D. et al. (1996)(supra). Briefly, microtiter plates were coated with purified recombinant O8E at 1-2 μg/ml in PBS, 50 μl/wells incubated 4° C. overnight then blocked with 200 μl/well of 5% chicken serum in PBS/Tween (0.05%). Dilutions of plasma from O8E-immunized mice were added to each well and incubated for 1-2 hours at ambient temperature. The plates were washed with PBS/Tween and then incubated with a goat-anti-human IgG Fc polyclonal antibody conjugated with horseradish peroxidase (HRP) for 1 hour at room temperature. After washing, the plates were developed with ABTS substrate (Sigma, A-1888, 0.22 mg/ml) and analyzed by spectrophotometer at OD 415-495. Mice that developed the highest titers of anti-O8E antibodies were used for fusions. Fusions were performed as described below and hybridoma supernatants were tested for anti-O8E activity by ELISA and FACS.

Generation of Hybridomas Producing Human Monoclonal Antibodies to O8E:

The mouse splenocytes, isolated from the HuMab Mice™ and KM Mice™, were fused with PEG to a mouse myeloma cell line either using PEG based upon standard protocols. The resulting hybridomas were then screened for the production of antigen-specific antibodies. Single cell suspensions of splenic lymphocytes from immunized mice were fused to one-fourth the number of SP2/0 non mouse myeloma cells (ATCC, CRL 1581) with 50% PEG (Sigma). Cells were plated at approximately $1 \times 10^5$ cells/well in flat bottom microtiter plate, followed by a about two week incubation in selective medium containing 10% fetal bovine serum (Hyclone, Logan, Utah), 10% P388DI (ATCC, CRL TIB-63) conditioned medium, 3-5% origen (IGEN) in DMEM (Mediatech, CRL 10013, with high glucose, L-glutamine and sodium pyruvate) plus 5 mM HEPES, 0.055 mM 2-mercaptoethanol, 50 mg/ml gentamycin and 1× HAT (Sigma, CRL P-7185). After one to two weeks, cells were cultured in medium in which HAT was replaced with HT. Individual wells were then screened by ELISA and FACS (described above) for human anti-O8E monoclonal IgG antibodies. The positive clones were then screened for O8E positive antibodies on O8E recombinant protein by ELISA or on O8E expressing cells, for example CHO-O8E transfected cells, by FACS. Briefly, O8E-expressing cells were freshly harvested from tissue culture flasks and a single cell suspension prepared. O8E-expressing cell suspensions were either stained with primary antibody directly or after fixation with 1% paraformaldehyde in PBS. Approximately one million cells were resuspended in PBS containing 0.5% BSA and 50-200 µg/ml of primary antibody and incubated on ice for 30 minutes. The cells were washed twice with PBS containing 0.1% BSA, 0.01% NaN$_3$, resuspended in 100 µl of 1:100 diluted FITC-conjugated goat-anti-human IgG (Jackson ImmunoResearch, West Grove, Pa.) and incubated on ice for an additional 30 minutes. The cells were again washed twice, resuspended in 0.5 ml of wash buffer and analyzed for fluorescent staining on a FACSCalibur cytometer (Becton-Dickinson, San Jose, Calif.).

Once extensive hybridoma growth occurred, medium was monitored usually after 10-44 days. The antibody-secreting hybridomas were replated, screened again and, if still positive for human IgG, anti-O8E monoclonal antibodies were subcloned at least twice by limiting dilution. The stable subclones were then cultured in vitro to generate small amounts of antibody in tissue culture medium for further characterization.

Hybridoma clones 1G11, 2A7, 2F9, 12E1 and 13D12 were selected for further analysis.

Example 2

Structural Characterization of Human Monoclonal Antibodies 1G11, 2A7, 2F9, 12E1 and 13D12

This Example discloses sequence analysis five (5) human monoclonal antibodies that specifically bind to O8E.

The cDNA sequences encoding the heavy and light chain variable regions of the 1G11, 2A7, 2F9, 12E1 and 13D12 monoclonal antibodies were obtained from the 1G11, 2A7, 2F9, 12E1 and 13D12 hybridomas, respectively, using standard PCR techniques and were sequenced using standard DNA sequencing techniques.

The nucleotide and amino acid sequences of the heavy chain variable region of 1G11 are shown in FIG. 1A and in SEQ ID NOs: 41 and 1, respectively.

The nucleotide and amino acid sequences of the light chain variable region of 1G11 are shown in FIG. 1B and in SEQ ID NO: 46 and 6, respectively.

Comparison of the 1G11 heavy chain immunoglobulin sequence to the known human germline immunoglobulin heavy chain sequences demonstrated that the 1G11 heavy chain utilizes a VH segment from human germline VH 4-34. The alignment of the 1G11 VH sequence to the germline VH 4-34 sequence is shown in FIG. 6. Further analysis of the 1G11 VH sequence using the Kabat system of CDR region determination led to the delineation of the heavy chain CDR1, CDR2 and CD3 regions as shown in FIGS. 1A and 6 and in SEQ ID NOs: 11, 16 and 21, respectively.

Comparison of the 1G11 light chain immunoglobulin sequence to the known human germline immunoglobulin light chain sequences demonstrated that the 1G11 light chain utilizes a VL segment from human germline VK A27. The alignment of the 1G11 VL sequence to the germline VK A27 sequence is shown in FIG. 9. Further analysis of the 1G11 VL sequence using the Kabat system of CDR region determination led to the delineation of the light chain CDR1, CDR2 and CD3 regions as shown in FIGS. 1B and 9 and in SEQ ID NOs: 26, 31 and 36, respectively.

The nucleotide and amino acid sequences of the heavy chain variable region of 2A7 are shown in FIG. 2A and in SEQ ID NO: 42 and 2, respectively.

The nucleotide and amino acid sequences of the light chain variable region of 2A7 are shown in FIG. 2B and in SEQ ID NO: 47 and 7, respectively.

Comparison of the 2A7 heavy chain immunoglobulin sequence to the known human germline immunoglobulin heavy chain sequences demonstrated that the 2A7 heavy chain utilizes a VH segment from human germline VH 3-53 and a JH segment from human germline JH 6b. The alignment of the 2A7 VH sequence to the germline VH 3-53 sequence is shown in FIG. 7. Further analysis of the 2A7 VH sequence using the Kabat system of CDR region determination led to the delineation of the heavy chain CDR1, CDR2 and CD3 regions as shown in FIGS. 2A and 7 and in SEQ ID NOs: 12, 17 and 22, respectively.

Comparison of the 2A7 light chain immunoglobulin sequence to the known human germline immunoglobulin light chain sequences demonstrated that the 2A7 light chain utilizes a VL segment from human germline VK A27. The alignment of the 2A7 VL sequence to the germline VK A27 sequence is shown in FIG. 9. Further analysis of the 2A7 VL sequence using the Kabat system of CDR region determination led to the delineation of the light chain CDR1, CDR2 and CD3 regions as shown in FIGS. 2B and 9 and in SEQ ID NOs: 27, 32 and 37, respectively.

The nucleotide and amino acid sequences of the heavy chain variable region of 2F9 are shown in FIG. 3A and in SEQ ID NO: 43 and 3, respectively.

The nucleotide and amino acid sequences of the light chain variable region of 2F9 are shown in FIG. 3B and in SEQ ID NO: 48 and 8, respectively.

Comparison of the 2F9 heavy chain immunoglobulin sequence to the known human germline immunoglobulin heavy chain sequences demonstrated that the 2F9 heavy chain utilizes a VH segment from human germline VH 3-53 and a JH segment from human germline JH 6b. The alignment of the 2F9 VH sequence to the germline VH 3-53 sequence is shown in FIG. 7. Further analysis of the 2F9 VH sequence using the Kabat system of CDR region determination led to the delineation of the heavy chain CDR1, CDR2 and CD3 regions as shown in FIGS. 3A and 7 and in SEQ ID NOs: 13, 18 and 23, respectively.

Comparison of the 2F9 light chain immunoglobulin sequence to the known human germline immunoglobulin light chain sequences demonstrated that the 2F9 light chain utilizes a VL segment from human germline VK A27. The alignment of the 2F9 VL sequence to the germline VK A27 sequence is shown in FIG. 9. Further analysis of the 2F9 VL sequence using the Kabat system of CDR region determination led to the delineation of the light chain CDR1, CDR2 and CD3 regions as shown in FIGS. 3B and 9 and in SEQ ID NOs: 28, 33 and 38, respectively.

The nucleotide and amino acid sequences of the heavy chain variable region of 12E1 are shown in FIG. 4A and in SEQ ID NO: 44 and 4, respectively.

The nucleotide and amino acid sequences of the light chain variable region of 12E1 are shown in FIG. 4B and in SEQ ID NO: 49 and 9, respectively.

Comparison of the 12E1 heavy chain immunoglobulin sequence to the known human germline immunoglobulin heavy chain sequences demonstrated that the 12E1 heavy chain utilizes a VH segment from human germline VH 3-9, a D segment from human germline 3-10 and a JH segment from human germline JH 6b. The alignment of the 12E1 VH sequence to the germline VH 3-9 sequence is shown in FIG. 8. Further analysis of the 12E1 VH sequence using the Kabat system of CDR region determination led to the delineation of the heavy chain CDR1, CDR2 and CD3 regions as shown in FIGS. 3A and 8 and in SEQ ID NOs: 14, 19 and 24, respectively.

Comparison of the 12E1 light chain immunoglobulin sequence to the known human germline immunoglobulin light chain sequences demonstrated that the 12E1 light chain utilizes a VL segment from human germline VK L6 and a JK segment from human germline JK 1. The alignment of the 12E1 VL sequence to the germline VK L6 sequence is shown in FIG. 10. Further analysis of the 12E1 VL sequence using the Kabat system of CDR region determination led to the delineation of the light chain CDR1, CDR2 and CD3 regions as shown in FIGS. 3B and 10 and in SEQ ID NOs: 29, 34 and 39, respectively.

The nucleotide and amino acid sequences of the heavy chain variable region of 13D12 are shown in FIG. 5A and in SEQ ID NO: 45 and 5, respectively.

The nucleotide and amino acid sequences of the light chain variable region of 13D12 are shown in FIG. 5B and in SEQ ID NO: 50 and 10, respectively.

Comparison of the 13D12 heavy chain immunoglobulin sequence to the known human germline immunoglobulin heavy chain sequences demonstrated that the 13D12 heavy chain utilizes a VH segment from human germline VH 4-34. The alignment of the 13D12 VH sequence to the germline VH 4-34 sequence is shown in FIG. 6. Further analysis of the 13D12 VH sequence using the Kabat system of CDR region determination led to the delineation of the heavy chain CDR1, CDR2 and CD3 regions as shown in FIGS. 5A and 6 and in SEQ ID NOs: 15, 20 and 25, respectively.

Comparison of the 13D12 light chain immunoglobulin sequence to the known human germline immunoglobulin light chain sequences demonstrated that the 13D12 light chain utilizes a VL segment from human germline VK A27. The alignment of the 13D12 VL sequence to the germline VK A27 sequence is shown in FIG. 9. Further analysis of the 13D12 VL sequence using the Kabat system of CDR region determination led to the delineation of the light chain CDR1, CDR2 and CD3 regions as shown in FIGS. 5B and 9 and in SEQ ID NOs: 30, 35 and 40, respectively.

Example 3

Characterization of Binding Specificity of Anti-O8E Human Monoclonal Antibodies

This Example discloses a comparison of anti-O8E antibodies on binding to immunopurified O8E performed by standard ELISA to examine the specificity of binding for O8E.

Recombinant His-tagged and myc-tagged O8E was coated on a plate overnight., then tested for binding against the anti-O8E human monoclonal antibodies 2A7, 12E1 and 13D12. Standard ELISA procedures were performed. The anti-O8E human monoclonal antibodies were added at a concentration of 1 µg/ml and titrated down at 1:2 serial dilutions. Goat-anti-human IgG (Fc or kappa chain-specific) polyclonal antibody conjugated with horseradish peroxidase (HRP) was used as secondary antibody.

Recombinant B7H4-Ig was purified from supernatants of 293T cells transfected with a B7H4-Ig construct by chromatography using protein A. An ELISA plate was coated with the human antibodies, followed by addition of purified protein and then detection with the rabbit anti-B7H4 antisera. See, FIG. 11A. Recombinant Penta-B7H4 protein with a C-9 tag was purified from supernatants of 293T cells transfected with a Penta-B7H4-C9 construct by chromatography using a 2A7 affinity column. An ELISA plate was coated with anti-mouse Fc, followed by monoclonal anti-C9 (0.6 ug/ml), then titrated Penta-B7H4 as indicated, then the human antibodies at 1 ug/ml. Coated anti-mouse Fc followed by M-anti-C9 (0.6 ug/ml), then titrated Penta-O8E as indicated, then humabs @ 1 ug/ml. See, FIG. 11B.

The anti-O8E human monoclonal antibodies 2A7, 12E1 and 13D12 bound with high specificity to O8E.

Example 4

Characterization of Anti-O8E Antibody Binding to O8E Expressed on the Surface of Breast Cancer Carcinoma Cell Lines This Example discloses the testing of anti-O8E antibodies for binding to CHO-O8E (a/k/a B7H4, B7S1 and B7x) transfectants and breast cell carcinoma cells expressing O8E on their cell surface by flow cytometry.

A CHO cell line transfected with O8E as well as the breast cell carcinoma cell line SKBR3 (ATCC Accession No. HTB-30) were tested for antibody binding. Binding of the HuMAb 2A7 anti-O8E human monoclonal antibody was assessed by incubating $1 \times 10^5$ cells with 2A7 at a concentration of 1 µg/ml. The cells were washed and binding was detected with a FITC-labeled anti-human IgG Ab. Flow cytometric analyses were performed using a FACScan flow cytometry (Becton Dickinson, San Jose, Calif.). The results are shown in FIGS. 12 and 13.

These data demonstrate that the anti-O8E HuMAbs bind to O8E expressing C110 cells and to an exemplary breast cell carcinoma cell line.

Example 5

Scatchard Analysis of Binding Affinity of Anti-O8E Monoclonal Antibodies

This Example discloses the testing of human monoclonal antibodies 1G11, 2F9, 2A7, 12E1 and 13D12 monoclonal antibodies for binding affinity to a O8E transfected HEK cell line using a Scatchard analysis.

HEK cells were transfected with full length O8E using standard techniques and grown in RPMI media containing 10% fetal bovine serum (FBS). (FIG. 12 presents FACs analysis of these HEK-O8E cells with the 2A7 human anti-O8E monoclonal antibody.) The cells were trypsinized and washed once in Tris based binding buffer (24 mM Tris pH 7.2, 137 mM NaCl, 2.7 mM KCl, 2 mM Glucose, 1 mM $CaCl_2$, 1 mM $MgCl_2$, 0.1% BSA) and the cells were adjusted to $2 \times 10^6$ cells/ml in binding buffer. Millipore plates (MAFB NOB) were coated with 1% nonfat dry milk in water and stored a 4° C. overnight. The plates were washed three times with 0.2 ml of binding buffer. Fifty microliters of buffer alone was added to the maximum binding wells (total binding). Twenty-five microliters of buffer alone was added to the control wells (non-specific binding). Varying concentration of $^{125}$I-anti-O8E antibody was added to all wells in a volume of 25 µl. (In some cases FITC labeled antibodies were used for the titration since unlabeled material was not available, binding may be compromised in these instances.) Varying concentrations of unlabeled antibody at 100 fold excess was added in a volume of 25 µl to control wells and 25 µl of O8E transfected CHO cells ($2 \times 10^6$ cells/ml) in binding buffer were added to all wells. The plates were incubated for 2 hours at 200 RPM on a shaker at 4° C. At the completion of the incubation the Millipore plates were washed three times with 0.2 ml of cold wash buffer (24 mM Tris pH 7.2, 500 mM NaCl, 2.7 mM KCl, 2 mM Glucose, 1 mM $CaCl_2$, 1 mM $MgCl_2$, 0.1% BSA.). The filters were removed and counted in a gamma counter. Evaluation of equilibrium binding was performed using single site binding parameters with the Prism software (San Diego, Calif.).

Data were analyzed by non-linear regression using a sigmoidal dose response (PRIZM™) and resulted in calculation of an EC50, which was used to rank the antibodies as illustrated in Table 2. The EC50 values calculated in these experiments are qualitative measures of antibody affinity and do not represent absolute affinities for O8E.

TABLE 2

| Antibody | EC50 | 95% CI |
|---|---|---|
| 2F9.E6-FITC | 407 pM | 250 to 663 pM |
| 13D12.G10 | 746 pM | 569 to 979 pM |
| 2A7.C11 | 750 pM | 519 pM to 1 nM |
| 1G11.H11-FITC | 1.69 nM | 1.4 to 2.0 nM |
| 12E1.G9* | 19.8 pM | 14 to 27.6 nM |

*BOTTOM and TOP values adjusted as constants to compensate for incomplete curve.

Example 6

Internalization of Anti-O8E Monoclonal Antibody

This Example demonstrates the testing of anti-O8E HuMAbs for the ability to internalize into O8E-expressing CHO and breast carcinoma cells using a Hum-Zap internalization assay. The Hum-Zap assay tests for internalization of a primary human antibody through binding of a secondary antibody with affinity for human IgG conjugated to the toxin saporin.

The O8E-expressing breast carcinoma cancer cell line SKBR3 was seeded at $1.25 \times 10^4$ cells/well in 100 µl wells overnight. The anti-O8E HuMAb antibodies 1G11, 2F9, 2A7, 12E1 or 13D12 were added to the wells at a concentration of 10 µM. An isotype control antibody that is non-specific for O8E was used as a negative control. The Hum-Zap (Advanced Targeting Systems, San Diego, Calif., IT-22-25) was added at a concentration of 11 nM and plates were allowed to incubate for 72 hours. The plates were then pulsed with 1.0 µCi of $^3$H-thymidine for 24 hours, harvested and read in a Top Count Scintillation Counter (Packard instruments, Meriden, Conn.). The results are presented below in Table 3 and in FIGS. 14-15. The anti-O8E antibodies 1G11, 2F9, 2A7, 12E1 and 13D12 showed an antibody concentration dependent decrease in $^3$H-thymidine incorporation in O8E-expressing SKBR3 breast carcinoma cancer cells.

These data demonstrate that the anti-O8E antibodies 1G11, 2F9, 2A7, 12E1 and 13D12 internalize into a breast carcinoma cancer cell line.

TABLE 3

| | Assay No. 1 % internalization | | Assay No. 2 % internalization | | Assay No. 3 % internalization | |
|---|---|---|---|---|---|---|
| Anti-O8E | mean | sd | mean | sd | mean | sd |
| 2A7/C11 | 29 | 12 | 17.5 | 3.5 | 40.7 | 2.7 |
| 2F9.E6 | 37 | 17 | NT | NT | NT | NT |
| 1G11.H1 | 18 | 8 | NT | NT | NT | NT |
| 13D12.G10 | NT | NT | 12.1 | 2.5 | 12.2 | 2.8 |
| 12E1.G9 | NT | NT | 10.4 | 18.5 | 4.3 | 2.7 |

The ranking for internalization efficiency was averaged over three experiments in SKBR3 and two experiments in CHO-O8E. The internalization rankings, along with EC50s for binding to CHO-O8E, are presented in Tables 4 and 5. Results show that internalization efficiency does not directly correlate with binding affinity, which suggests that internalization is epitope dependant.

TABLE 4

Internalization Efficiency Sorted by Internalization in the SBKR3 Breast Carcinoma Cell Line

| | Internalization | | EC50 |
|---|---|---|---|
| Anti-O8E | SKBR3 | CHO-O8E | CHO-O8E binding |
| 2F9.E6 | 1 | 3 | 407 pM |
| 2A7.C11 | 2 | 1 | 750 pM |
| 1G11.H1 | 3 | 4 | 1.69 nM |
| 13D12.G10 | 4 | 2 | 746 pM |
| 12E1.G9 | 5 | 5 | 19.8 pM |

TABLE 5

Internalization Efficiency Sorted by Internalization in the CHO-O8E Cell Line

| | Internalization | | EC50 |
|---|---|---|---|
| Anti-O8E | SKBR3 | CHO-O8E | CHO-O8E binding |
| 2A7.C11 | 2 | 1 | 750 pM |
| 13D12.G10 | 4 | 2 | 746 pM |
| 2F9.E6 | 1 | 3 | 407 pM |

TABLE 5-continued

Internalization Efficiency Sorted by Internalization in the CHO-O8E Cell Line

| Anti-O8E | Internalization | | EC50 |
|---|---|---|---|
| | SKBR3 | CHO-O8E | CHO-O8E binding |
| 1G11.H1 | 3 | 4 | 1.69 nM |
| 12E1.G9 | 5 | 5 | 19.8 pM |

The internalization activity of the saporin conjugates in CHO-O8E was measured with a dose response through a ~500 pM to 1 pM range using human monoclonal antibodies 2A7, 2F9 and 1G11. As illustrated in FIG. 14, internalization was very efficient with EC50s in the low pM range. A CHO parental cell line and Hu IgG-SAP were used as negative controls and showed no significant background toxicity or non-specific internalization. Direct anti-O8E conjugates to SAP were used with SKBR3 cells. The percentage of internalization (vs control) as a function of Ig-SAP dose is presented in FIG. 15.

Example 7

Assessment of Cell Killing of a Toxin-Conjugated Anti-O8E Antibody on Breast Cell Carcinoma Canines This Example discloses the testing of anti-O8E monoclonal antibodies conjugated to a toxin for the ability to kill an O8E$^+$ breast cell carcinoma cell line in a cell proliferation assay.

The anti-O8E HuMAb antibodies 1G11, 2F9, 2A7, 12E1 or 13D12 may be conjugated to a toxin via a linker, such as a peptidyl, hydrazone or disulfide linker. An O8E-expressing breast carcinoma cancer cell line, such as SKBR3, is seeded at between about 1 and $3 \times 10^4$ cells/wells in 100 µl wells for 3 hours. An anti-O8E antibody-toxin conjugate is added to the wells at a starting concentration of 30 nM and titrated down at 1:3 serial dilutions. An isotype control antibody that is non-specific for O8E is used as a negative control. Plates are allowed to incubate for 69 hours. The plates are then pulsed with 1.0 gel of $^3$H-thymidine for 24 hours, harvested and read in a Top Count Scintillation Counter (Packard Instruments, Meriden, Conn.). Anti-O8E antibodies are expected to show an antibody-toxin concentration dependent decrease in $^3$H-thymidine incorporation in O8E-expressing breast carcinoma cancer cells. This data demonstrates that the anti-O8E antibodies 1G11, 2F9, 2A7, 12E1 and 13D12 are potentially cytotoxic to breast carcinoma cancer cells when conjugated to a toxin.

Example 8

Assessment of ADCC Activity of Anti-O8E Antibody

This Example discloses the testing of anti-O8E monoclonal antibodies for the ability to kill O8E$^+$ cell lines in the presence of effector cells via antibody dependent cellular cytotoxicity (ADCC) in a fluorescence cytotoxicity assay.

Human effector cells were prepared from whole blood as follows. Human peripheral blood mononuclear cells were purified from heparinized whole blood by standard Ficoll-paque separation. The cells were resuspended in RPMI1640 media containing 10% FBS and 200 U/ml of human IL-2 and incubated overnight at 37° C. The following day, the cells were collected and washed four times in culture media and resuspended at $2 \times 10^7$ cells/ml. Target O8E$^+$ cells were incubated with BATDA reagent (Perkin Elmer, Wellesley, Mass.) at 2.5 µl BATDA per $1 \times 10^6$ target cells/mL for 20 minutes at 37° C. The target cells were washed four times, spun down and brought to a final volume of $1 \times 10^5$ cells/ml.

The O8E$^+$ cell line SKBR3 as well as an O8E transfected SKOV3 cell-line were tested for antibody specific ADCC to the human anti-O8E monoclonal antibodies using the Delfia fluorescence emission analysis as follows. Each target cell line (100 µl of labeled target cells) was incubated with 50 µl of effector cells and 50 µl of antibody. A target to effector ratio of 1:50 was used throughout the experiments. In all studies, a human IgG1 isotype control was used as a negative control. Following a 2000 rpm pulse spin and one hour incubation at 37° C., the supernatants were collected, quick spun again and 20 µl of supernatant was transferred to a flat bottom plate, to which 180 µl of Eu solution (Perkin Elmer, Wellesley, Mass.) was added and read in a RubyStar reader (BMG Labtech). The % lysis was calculated as follows: (sample release−spontaneous release*100)/(maximum release−spontaneous release), where the spontaneous release is the fluorescence from wells which only contain target cells and maximum release is the fluorescence from wells containing target cells and have been treated with 2% Triton-X. Cell cytotoxicity % lysis for the SKBR3 cells with anti-O8E antibodies 1G11, 2F9 and 2A7 are presented in FIG. 17; cell cytotoxicity % lysis for the SKOV3-O8E transfected cell line with anti-O8E antibodies 1G11, 2F9 and 2A7 are presented in FIG. 18; and concentration-dependent cell cytotoxicity % lysis for the SKBR3 cells with anti-O8E antibodies 2F9 and 2A7 are presented in FIG. 19. Both of the O8E$^+$-expressing cell lines SKBR3 and SKOV3-O8E showed antibody mediated cytotoxicity with the HuMAb anti-O8E antibodies 1G11, 2F9 and 2A7. These data demonstrate that HuMAb anti-O8E antibodies show specific cytotoxicity to O8E$^+$ expressing cells.

Example 9

Treatment of In Vivo Tumor Xenograft Model Using Naked and Cytotoxin-Conjugated Anti-O8E Antibodies This Example discloses the in vivo treatment of mice implanted with a breast cell carcinoma tumor with toxin-conjugated anti-O8E antibodies to examine the in vivo effect of the antibodies on tumor growth.

SKBR3 or other suitable breast cell carcinoma cells are expanded in vitro using standard laboratory procedures. Male Ncr athymic nude mice (Taconic, Hudson, N.Y.) between 6-8 weeks of age are implanted subcutaneously in the right flank with $7.5 \times 10^6$ ACHN or A-498 cells in 0.2 ml of PBS/Matrigel (1:1) per mouse. Mice are weighed and measured for tumors three dimensionally using an electronic caliper twice weekly after implantation. Tumor volumes are calculated as height× width×length. Mice with ACHN tumors averaging 270 mm$^3$ or A498 tumors averaging 110 mm$^3$ are randomized into treatment groups. The mice are dosed intraperitoneally with PBS vehicle, toxin-conjugated isotype control antibody or toxin-conjugated anti-O8E HuMAb on Day 0. Examples of toxin compounds that may be conjugated to the antibodies of the current disclosure are described in pending U.S. patent application designated MEDX-0034US4. The mice receiving anti-O8E HuMAb are tested with three different toxin compounds. Mice are monitored for tumor growth for 60 days post dosing. Mice are euthanized when the tumors reached tumor end point (2000 mm³). Suitable anti-O8E antibodies conjugated to a toxin extend the mean time to reaching the tumor end point volume (2000 mm³) and slow tumor growth progression. Thus, treatment with such an anti-O8E antibody-toxin conjugate has a direct in vivo inhibitory effect on tumor growth.

Example 10

Immunohistochemistry with Anti-O8E HuMAb 2A7

This Example discloses that the anti-O8E HuMAb 2A7 to recognize O8E by immunohistochemistry using normal mouse tissue arrays (IMGENEX Histo-Array; Imgenex Corp., San Diego, Calif.).

For immunohistochemistry, 2,000 µm tissue cores were used. After drying for 30 minutes, sections were fixed with acetone (at room temperature for 10 minutes) and air-dried for 5 minutes. Slides were rinsed in PBS and then pre-incubated with 10% normal goat serum in PBS for 20 min and subsequently incubated with 10 µg/ml fitcylated 2A7 in PBS with 10% normal goat serum for 30 min at room temperature. Next, slides were washed three times with PBS and incubated for 30 min with mouse anti-FITC (10 µg/ml DAKO) at room temperature. Slides were washed again with PBS and incubated with Goat anti-mouse HRP conjugate (DAKO) for 30 minutes at room temperature. Slides were washed again 3× with PBS. Diaminobenzidine (Sigma) was used as substrate, resulting in brown staining. After washing with distilled water, slides were counter-stained with hematoxylin for 1 min. Subsequently, slides were washed for 10 secs in running distilled water and mounted in glycergel (DAKO). The results of these studies are presented in Table 6.

TABLE 6

| Immunoreactivity of O8E in Normal Mouse Tissue Array | | | |
|---|---|---|---|
| | 2A7.C11-FITC | | Hu-IgG1-FITC |
| Tissue Types | 2 µg/ml | 5 µg/ml | 5 µg/ml |
| Skin, ear lobe | | | |
| Epidermis | − | ± | − |
| Sabaceous gland | − | ± | − |
| Other elements | − | − | − |
| Colon | | | |
| Surface epithelium | ±, 1+ | 1+ | ± |
| Other elements | − | − | − |
| Small Intestine | | | |
| Crypt epithelium | ±, 1+ | 1+, 2+ | ± |
| Other elements | − | − | − |
| Stomach | | | |
| Surface & glandular epithelial cells | 1+, 2+, ocas | 1+, 2+, freq | 1+, 2+. ocas |
| Nerve plexus | − | ±, 1+ | − |
| Other elements | − | − | − |
| Pancreas | | | |
| Acinar epithelium | 1+ | 2+ | ±, 1+ |
| Islets | − | ± | − |
| Other elements | − | − | − |
| Salivary gland | | | |
| Acinar epithelium | ± | 1+ | − |
| Other elements | − | − | − |

TABLE 6-continued

| Immunoreactivity of O8E in Normal Mouse Tissue Array | | | |
|---|---|---|---|
| | 2A7.C11-FITC | | Hu-IgG1-FITC |
| Tissue Types | 2 µg/ml | 5 µg/ml | 5 µg/ml |
| Liver | | | |
| Hepatocytes | − | ±, − | − |
| Other elements | − | − | − |
| Cerebrum | | | |
| Neurons | ± | 2+, 1+, freq | ±, − |
| Neuropil/fibers | −, ± | 2+, 1+, ocas | − |
| Pons | | | |
| Neurons | ± | ± | ± |
| Neuropil/fibers | ± | 2+, 1+, freq | − |
| Cerebelleum | | | |
| Purkinje cells | ±, 1+ | 1+ | ±, − |
| White matter | − | 1+, 2+ | − |
| Other elements | − | − | − |
| Spleen | | | |
| Large lymphoid cells in red pulp | − | 1+, 2+, rare | − |
| Other elements | − | −, ± | − |
| Thymus | − | − | − |
| Skeletal muscle | − | − | − |
| Tongue | − | − | − |
| Heart | − | −, ± | − |
| Lung | − | − | − |
| Kidney cortex | − | −, ± | − |
| Kidney medulla | − | − | − |
| Urinary bladder | | | |
| Transitional epithelium | − | ±, 1+ | − |
| Other elements | − | − | − |
| Seminal vesicle | | | |
| Epithelium | ±, − | ± | − |
| Fluid in the lumen | 1+ | 3+ | ± |
| Other elements | − | − | − |
| Testis | | | |
| Primary Spermotocytes | − | ±, 1+ | − |
| Other elements | − | − | − |
| Epididymis | − | − | − |
| Uterus | | | |
| Endometrium/gland epithelium | −, ± | ± | − |
| Other elements | − | − | − |
| Ovary | − | ± | − |

Intensity of immunoreactivity:
+− (equivocal);
+ (weak);
2+ (moderate);
3+ (strong);
4+ (intense);
− (negative).
Freq: frequent;
Ocas: occasional These data and corresponding data collected for anti-O8E antibodies 1G11 and 2F9, demonstrate that strong to intense O8E immunoreactivity (3+, 4+) was present in enteroendocrine-like cells in colon and small intestine, as well as in the lumen fluid of seminary vesicle; weak to moderate O8E immunoreactivity (1+, 2+) was revealed in neurons of cerebrum, in neuropils and fibers of cerebrum and pons, in the white matter of cerebellum, in the crypt epithelial cells of small intestine and in a small number of large lymphoid cells in the spleen; weak O8E immunoreactivity (1+) was demonstrated in colon surface epithelium, Purkinje cells in cerebellum and acinar epithelium of salivary gland and pancreas;

equivocal to weak O8E immunoreactivity was shown in transitional epithelium of urinary bladder, primary spermotocytes of testis and nerve plexus in stomach; and all other organs exhibit negative to equivocal staining, which include skin, liver, heart, lung, thymus, kidney, uterus, ovary, epididymis, tongue and skeletal muscles.

Example 11

Production of Defucosylated HuMAbs

This Example demonstrates the production of anti-O8E HuMAbs lacking in fucosyl residues.

Antibodies with reduced amounts of fucosyl residues have been demonstrated to increase the ADCC ability of the antibody. The CHO cell line Ms704-PF, which lacks the fucosyltransferase gene FUT 8 (Biowa, Inc., Princeton, N.J.), is electroporated with a vector that expresses the heavy and light chains of an anti-O8E HuMAb. Drug-resistant clones are selected by growth in Ex-Cell 325-PF CHO media (JRH Biosciences, Lenexa, Kans.) with 6 mM L-glutamine and 500 µg/ml G418 (Invitrogen, Carlsbad, Calif.). Clones are screened for IgG expression by standard ELISA assay. Two separate clones are produced, B8A6 and B8C11, which has production rates ranging from 1.0 to 3.8 picograms per cell per day.

Example 12

Assessment of ADCC Activity of Defucosylated Anti-O8E Antibody

This Example discloses the testing of defucosylated and non-defucosylated anti-O8E monoclonal antibodies for the ability to kill O8E$^+$ cells in the presence of effector cells via antibody dependent cellular cytotoxicity (ADCC) in a fluorescence cytotoxicity assay.

Human anti-O8E monoclonal antibodies are defucosylated as described above. Human effector cells are prepared from whole blood as follows, Human peripheral blood mononuclear cells are purified from heparinized whole blood by standard Ficoll-paque separation. The cells are resuspended in RPMI1640 media containing 10% FBS (culture media) and 200 U/ml of human IL-2 and incubated overnight at 37° C. The following day, the cells are collected and washed once in culture media and resuspended at $2 \times 10^7$ cells/ml. Target O8E+ cells are incubated with BATDA reagent (Perkin Elmer, Wellesley, Mass.) at 2.5 µl BATDA per $1 \times 10^6$ target cells/mL in culture media supplemented with 2.5 mM probenecid (assay media) for 20 minutes at 37° C. The target cells are washed four times in PBS with 20 mM HEPES and 2.5 mM probenecid, spun down and brought to a final volume of $1 \times 10^5$ cells/ml in assay media.

The O8E+ cell line ARH-77 (human B lymphoblast leukemia; ATCC Accession No. CRL-1621) is tested for antibody specific ADCC to the defucosylated and non-defucosylated human anti-O8E monoclonal antibody using the Delfia fluorescence emission analysis as follows. The target cell line ARH77 (100 µl of labeled target cells) is incubated with 50 µl of effector cells and 50 µl of either 1G11 or defucosylated 1G11 antibody. A target to effector ratio of 1:100 is used throughout. A human IgG1 isotype control is used as a negative control. Following a 2100 rpm pulse spin and one hour incubation at 37° C., the supernatants are collected, quick spun again and 20 µl of supernatant is transferred to a flat bottom plate, to which 180 µl of Eu solution (Perkin Elmer, Wellesley, Mass.) is added and read in a Fusion Alpha TRF plate reader (Perkin Elmer). The % lysis is calculated as follows: (sample release−spontaneous release*100)/(maximum release−spontaneous release), where the spontaneous release is the fluorescence from wells which only contain target cells and maximum release is the fluorescence from wells containing target cells and have been treated with 3% Lysol. The O8E+expressing cell line ARH-77 will show an antibody mediated cytotoxicity with the HuMAb anti-O8E antibody 1G11 and an increased percentage of specific lysis associated with the defucosylated form of the anti-O8E antibody 1G11. Thus, defucosylated HuMAb anti-O8E antibodies increase specific cytotoxicity to O8E+ expressing cells.

Example 13

Internalization of HuMab Anti-08E Antibodies by Immuno Fluorescence Staining Analysis The target cell lines, 08E$^+$ SKBR3 (human breast cancer, ATCC# HTB-30) and ZR-75 (human breast cancer, ATCC# CRL-1500) were used to test for internalization of HuMab anti-08E antibodies 2A7C11, 1G11H1 and 2F9E6 upon binding to the cells using immuno-fluorescence staining.

SKBR3 and ZR-75 cells ($10^4$ per 100 µl per well in 96-well plate), harvested from tissue culture flask by treatment with 0.25% Trypsin/EDTA, were incubated with each of HuMab anti-08E antibodies at 5 µg/ml in FACS buffer (PBS+5% PBS, media) for 30 minutes on ice. A human IgG1 isotype control was used as a negative control. Following 2× washes with the media, the cells were re-suspended in the media (100 µl per well) and then incubated with goat anti-human secondary antibody conjugated with PE (Jackson ImmunoResearch Lab) at 1:00 dilution on ice for 30 minutes. Following washed with the media, the cells were either immediately imaged under a fluorescent microscope (Nikon) at 0 min or incubated at 37° C. for various times. The images of cell morphology and immuno-fluorescence intensity of the stained cells were taken at different time points as indicated in the figures below. The fluorescence was only observed in the cells stained with HuMab anti-08E antibodies, No fluorescence was detected with the IgG1 control antibody. Similar results were also obtained with FITC-direct conjugated HuMab anti-08E antibodies in the assays.

The imaging data showed the appearance of the fluorescence on cell surface membrane with all three HuMab anti-08E antibodies at 0 min. In 30 min incubation, the membrane fluorescence intensity significantly decreased while staining increased inside of the cells. At the 120 min point, the fluorescence on the membrane disappeared and instead appeared to be present in intracellular compartments. The data demonstrates that HuMab anti-08E antibodies can be specifically internalized upon binding to 08E-expressing endogenous tumor cells.

Example 14

Efficacy of Anti-O8E Antibodies on HEK-B7H4 Tumors in SCID Mice

In this Example, SCID mice implanted with HEK-B7H4 tumors are treated in vivo with naked anti-O8E antibodies to examine the in vivo effect of the antibodies on tumor growth.

Severe combined immune deficient (SCID) mice, which lack functional B and T lymphocytes were used to study tumor growth. Cells from the HEK tumor cell line transfected with B7H4 were implanted subcutaneously at 5 million cells/mouse in matrigel (50% v/v). Each mouse received an inoculum of 0.2 ml of cells on day 0. The mice were checked for tumor growth starting at day 10 and monitored twice weekly for tumor growth for approximately 6 weeks. When tumors reached about 130 mm$^3$, the mice were randomized by tumor volume into 3 groups. The mice were treated either with 10 mg/kg naked anti-O8E antibody 2A7, an isotype control antibody or formulation buffer as a negative control. The animals were dosed by intraperitoneal injection every 5 days for 5 injections. Using an electronic caliper, the tumors were measured three dimensionally (height×width×length) and tumor volume was calculated. Mice were euthanized when tumors reached a volume of 1500 mm$^3$ or showed greater than 15% weight loss. The results are shown in FIG. 20. Tumor growth was inhibited by treatment with the anti-O8E antibody 2A7. The median tumor growth inhibition for the group treated with 2A7 was 63% on day 34. The tumors resumed growth after the dosing was stopped. These results show that anti-O8E antibodies are effective in treating tumors that express O8E in vivo.

Example 15

Immunohistochemistry Using an Anti-O8E Antibody

The ability of the anti-B7H4 HuMAb 2A7 to recognize B7H4 by immunohistochemistry was examined using clinical biopsies from ovarian cancer, lung cancer, breast cancer, and head & neck cancer For immunohistochemistry, 5 μm frozen sections were used (Ardais Inc, USA). After drying for 30 minutes, sections were fixed with acetone (at room temperature for 10 minutes) and air-dried for 5 minutes, Slides were rinsed in PBS and then pre-incubated with 10% normal goat serum in PBS for 20 min and subsequently incubated with 10 μg/ml fitcylated antibody in PBS with 10% normal goat serum for 30 min at room temperature. Next, slides were washed three times with PBS and incubated for 30 min with mouse anti-FITC (10 μg/ml DAKO) at room temperature. Slides were washed again with PBS and incubated with Goat anti-mouse HRP conjugate (DAKO) for 30 minutes at room temperature. Slides were washed again 3× with PBS. Diaminobenzidine (Sigma) was used as substrate, resulting in brown staining. After washing with distilled water, slides were counterstained with hematoxylin for 1 min. Subsequently, slides were washed for 10 secs in running distilled water and mounted in glycergel (DAKO). Clinical biopsy immunohistochemical staining displayed positive staining in the lung cancer, breast cancer, ovarian cancer, and head & neck cancer samples.

Example 16

Quantitative RT-PCR on Normal and Cancer Tissues

Various normal and cancerous tissue samples were screened for O8E mRNA expression using quantitative reverse transcriptase PCR(RT-PCR). Expression of mRNA is indicative of O8E protein expression.

For quantitative RT-PCR, the following O8E primers were used: B7-H4.3: AGGATGGAATCCTGAGCTGCACTT (SEQ ID NO:57); B7-H4.4: TCCGACAGCTCATCTTTGC-CTTCT (SEQ ID NO:58) as provided by Operon (Huntsville, Ala.). Standard reaction conditions were used (5 μl cDNA template at 1 ng/μl, 0.1 μl upstream primer at 40 μM, 0.1 μl downstream primer at 40 μM, 6 μl 2×SYBR Green PCR mix (Applied Biosystems #4367659), and 0.8 μl water). The cDNA was amplified for 40 cycles using standard PCR conditions in an ABI Prism 7900HT (Applied Biosystems, Foster City, Calif.). The quantitative RT-PCR results are shown in Table 7 below. Samples with undetermined counts represent values that were below a fluorescence threshold. Breast, ovarian and head and neck tumors were shown to express O8E, with the highest levels of expression seen in some ovarian and head and neck cancer samples. This demonstrates that there is increased expression of O8E in breast, ovarian and head and neck tumor samples relative to normal tissue.

TABLE 7

Quantitative RT-PCR expression in normal and cancer tissues

| Tissue | Count | Quantity |
| --- | --- | --- |
| N.Adipose (#301) | 28.953062 | 25.57793 |
| N.Artery (#303) | 31.856901 | 3.0423617 |
| N.Bladder (#257) | 30.620392 | 7.5326214 |
| N.Bone Marrow (#342) | Undetermined | 0 |
| N.Brain (#258) | 34.33955 | 0.49280354 |
| N.Breast (#259) | 25.63064 | 292.28528 |
| N.Colon (#261) | Undetermined | 0 |
| N.Esophagus (#262) | 32.27514 | 2.2388945 |
| N.Heart (#125) | Undetermined | 0 |
| N.Kidney (#264) | 33.599422 | 0.8479082 |
| N.Liver (#266) | Undetermined | 0 |
| N.Lung (#268) | 32.44523 | 1.9763907 |
| N.Lymph Node (#315) | Undetermined | 0 |
| N.Ovary (#270) | 35.045704 | 0.29364112 |
| N.Pancreas (#271) | 28.446985 | 37.06916 |
| N.Peripheral Blood Leukocytes (#302) | 34.652363 | 0.39180183 |
| N.Prostate (#272) | 32.635994 | 1.7184163 |
| N.Retina (#256) | 34.70426 | 0.37717298 |
| N.Skeletal Muscle (#119) | Undetermined | 0 |
| N.Skeletal Muscle (#126) | Undetermined | 0 |
| N.Skin (#273) | Undetermined | 0 |
| N.Spinal Cord (#129) | 39.383526 | 0.01220525 |
| N.Spleen (#274) | Undetermined | 0 |
| N.Stomach (#275) | Undetermined | 0 |
| N.Tongue (#324) | 30.956758 | 5.886249 |
| N.Tonsil (#325) | Undetermined | 0 |
| N.Trachea (#314) | 29.771343 | 14.03797 |
| Breast T. (#176) | 33.798374 | 0.7328206 |
| Breast T. (#177) | 25.759022 | 266.02777 |
| Breast T. (#178) | 28.572468 | 33.81085 |
| Breast T. (#179) | 25.31508 | 368.374 |
| Breast T. (#180) | 29.323488 | 19.494516 |
| Head/Neck T. (Larynx, #402) | 28.116425 | 47.23582 |
| Head/Neck T. (Pharynx, #403) | 25.776083 | 262.72076 |
| Head/Neck T. (Tongue, #403) | 26.950275 | 111.07142 |
| Head/Neck T. (Tonsil, #404) | 23.03704 | 1957.3722 |
| Kidney T. (#167) | 27.029814 | 104.77927 |
| Ovary T. (#187) | 25.321087 | 366.75625 |
| Ovary T. (#188) | 22.846964 | 2250.0833 |
| Ovary T. (#189) | 25.079527 | 437.81958 |
| Ovary T. (#190) | 27.964441 | 52.80399 |
| Ovary T. (#191) | 22.686525 | 2530.9656 |

The present disclosure is not to be limited in scope by the specific embodiments described herein. Indeed, various modifications of this disclosure in addition to those described herein will become apparent to those skilled in the art from the foregoing description and the accompanying figures. Such modifications are intended to fall within the scope of the appended claims.

Patents, patent applications, publications, product descriptions and protocols are cited throughout this application, the disclosures of which are incorporated herein by reference in their entireties for all purposes.

What is claimed is:

1. A method of treating a disease characterized by growth of tumor cells expressing O8E in a subject, comprising administering to the subject an isolated monoclonal antibody or an antigen-binding portion thereof, in an amount effective to treat the disease, wherein the antibody or antigen binding portion thereof comprises a heavy chain variable region comprising CDR1, CDR2, and CDR3 domains; and a light chain variable region comprising CDR1, CDR2, and CDR3 domains, wherein the heavy chain variable region and light chain variable region CDR1, CDR2, and CDR3 domains are selected from the group consisting of:

(a) a heavy chain variable region CDR1 comprising amino acids having the sequence set forth in SEQ ID NO:11; a heavy chain variable region CDR2 comprising amino acids having the sequence set forth in SEQ ID NO:16; a heavy chain variable region CDR3 comprising amino acids having the sequence set forth in SEQ ID NO:21; a light chain variable region CDR1 comprising amino acids having the sequence set forth in SEQ ID NO:26; a light chain variable region CDR2 comprising amino acids having the sequence set forth in SEQ ID NO:31; and a light chain variable region CDR3 comprising amino acids having the sequence set forth in SEQ ID NO:36;

(b) a heavy chain variable region CDR1 comprising amino acids having the sequence set forth in SEQ ID NO:12; a heavy chain variable region CDR2 comprising amino acids having the sequence set forth in SEQ ID NO:17; a heavy chain variable region CDR3 comprising amino acids having the sequence set forth in SEQ ID NO:22; a light chain variable region CDR1 comprising amino acids having the sequence set forth in SEQ ID NO:27; a light chain variable region CDR2 comprising amino acids having the sequence set forth in SEQ ID NO:32; and a light chain variable region CDR3 comprising amino acids having the sequence set forth in SEQ ID NO:37;

(c) a heavy chain variable region CDR1 comprising amino acids having the sequence set forth in SEQ ID NO:13; a heavy chain variable region CDR2 comprising amino acids having the sequence set forth in SEQ ID NO:18; a heavy chain variable region CDR3 comprising amino acids having the sequence set forth in SEQ ID NO:23; a light chain variable region CDR1 comprising amino acids having the sequence set forth in SEQ ID NO:28; a light chain variable region CDR2 comprising amino acids having the sequence set forth in SEQ ID NO:33; and a light chain variable region CDR3 comprising amino acids having the sequence set forth in SEQ ID NO:38;

(d) a heavy chain variable region CDR1 comprising amino acids having the sequence set forth in SEQ ID NO:14; a heavy chain variable region CDR2 comprising amino acids having the sequence set forth in SEQ ID NO:19; a heavy chain variable region CDR3 comprising amino acids having the sequence set forth in SEQ ID NO:24; a light chain variable region CDR1 comprising amino acids having the sequence set forth in SEQ ID NO:29; a light chain variable region CDR2 comprising amino acids having the sequence set forth in SEQ ID NO:34; and a light chain variable region CDR3 comprising amino acids having the sequence set forth in SEQ ID NO:39; and (e) a heavy chain variable region CDR1 comprising amino acids having the sequence set forth in SEQ ID NO:15; a heavy chain variable region CDR2 comprising amino acids having the sequence set forth in SEQ ID NO:20; a heavy chain variable region CDR3 comprising amino acids having the sequence set forth in SEQ ID NO:25; a light chain variable region CDR1 comprising amino acids having the sequence set forth in SEQ ID NO:30; a light chain variable region CDR2 comprising amino acids having the sequence set forth in SEQ ID NO:35; and a light chain variable region CDR3 comprising amino acids having the sequence set forth in SEQ ID NO:40; and wherein the antibody or antigen-binding portion thereof specifically binds to human O8E, and wherein the antigen-binding portion thereof is conjugated to a therapeutic agent.

2. The method of claim 1, wherein the antibody or antigen-binding portion thereof comprises:
a) a heavy chain variable region CDR1 comprising amino acids having the sequence set forth in SEQ ID NO: 11;
b) a heavy chain variable region CDR2 comprising amino acids having the sequence set forth in SEQ ID NO: 16;
c) a heavy chain variable region CDR3 comprising amino acids having the sequence set forth in SEQ ID NO: 21;
d) a light chain variable region CDR1 comprising amino acids having the sequence set forth in SEQ ID NO: 26;
e) a light chain variable region CDR2 comprising amino acids having the sequence set forth in SEQ ID NO: 31; and
f) a light chain variable region CDR3 comprising amino acids having the sequence set forth in SEQ ID NO: 36.

3. The method of claim 1, wherein the antibody or antigen-binding portion thereof comprises:
a) a heavy chain variable region CDR1 comprising amino acids having the sequence set forth in SEQ ID NO: 12;
b) a heavy chain variable region CDR2 comprising amino acids having the sequence set forth in SEQ ID NO: 17;
c) a heavy chain variable region CDR3 comprising amino acids having the sequence set forth in SEQ ID NO: 22;
d) a light chain variable region CDR1 comprising amino acids having the sequence set forth in SEQ ID NO: 27;
e) a light chain variable region CDR2 comprising amino acids having the sequence set forth in SEQ ID NO: 32; and
f) a light chain variable region CDR3 comprising amino acids having the sequence set forth in SEQ ID NO: 37.

4. The method of claim 1, wherein the antibody or antigen-binding portion thereof comprises:
a) a heavy chain variable region CDR1 comprising amino acids having the sequence set forth in SEQ ID NO: 13;
b) a heavy chain variable region CDR2 comprising amino acids having the sequence set forth in SEQ ID NO: 18;
c) a heavy chain variable region CDR3 comprising amino acids having the sequence set forth in SEQ ID NO: 23;
d) a light chain variable region CDR1 comprising amino acids having the sequence set forth in SEQ ID NO: 28;
e) a light chain variable region CDR2 comprising amino acids having the sequence set forth in SEQ ID NO: 33; and
f) a light chain variable region CDR3 comprising amino acids having the sequence set forth in SEQ ID NO: 38.

5. The method of claim 1, wherein the antibody or antigen-binding portion thereof comprises:
a) a heavy chain variable region CDR1 comprising amino acids having the sequence set forth in SEQ ID NO: 14;
b) a heavy chain variable region CDR2 comprising amino acids having the sequence set forth in SEQ ID NO: 19;
c) a heavy chain variable region CDR3 comprising amino acids having the sequence set forth in SEQ ID NO: 24;
d) a light chain variable region CDR1 comprising amino acids having the sequence set forth in SEQ ID NO: 29;
e) a light chain variable region CDR2 comprising amino acids having the sequence set forth in SEQ ID NO: 34; and
f) a light chain variable region CDR3 comprising amino acids having the sequence set forth in SEQ ID NO: 39.

6. The method of claim 1, wherein the antibody or antigen-binding portion thereof comprises:
a) a heavy chain variable region CDR1 comprising amino acids having the sequence set forth in SEQ ID NO: 15;
b) a heavy chain variable region CDR2 comprising amino acids having the sequence set forth in SEQ ID NO: 20;
c) a heavy chain variable region CDR3 comprising amino acids having the sequence set forth in SEQ ID NO: 25;
d) a light chain variable region CDR1 comprising amino acids having the sequence set forth in SEQ ID NO: 30;
e) a light chain variable region CDR2 comprising amino acids having the sequence set forth in SEQ ID NO: 35; and
f) a light chain variable region CDR3 comprising amino acids having the sequence set forth in SEQ ID NO: 40.

7. The method of claim 1, wherein the antibody or antigen-binding portion thereof comprises:
a) a heavy chain variable region comprising amino acids having the sequence set forth in SEQ ID NO: 1; and
b) a light chain variable region comprising amino acids having the sequence set forth in SEQ ID NO: 6.

8. The method of claim 1, wherein the antibody or antigen-binding portion thereof comprises:
a) a heavy chain variable region comprising amino acids having the sequence set forth in SEQ ID NO: 2; and
b) a light chain variable region comprising amino acids having the sequence set forth in SEQ ID NO: 7.

9. The method of claim 1, wherein the antibody or antigen-binding portion thereof comprises:
a) a heavy chain variable region comprising amino acids having the sequence set forth in SEQ ID NO: 3; and
b) a light chain variable region comprising amino acids having the sequence set forth in SEQ ID NO: 8.

10. The method of claim 1, wherein the antibody or antigen-binding portion thereof comprises:
a) a heavy chain variable region comprising amino acids having the sequence set forth in SEQ ID NO: 4; and
b) a light chain variable region comprising amino acids having the sequence set forth in SEQ ID NO: 9.

11. The method of claim 1, wherein the antibody or antigen-binding portion thereof comprises:
a) a heavy chain variable region comprising amino acids having the sequence set forth in SEQ ID NO: 5; and b) a light chain variable region comprising amino acids having the sequence set forth in SEQ ID NO: 10.

12. A method of treating a disease characterized by growth of tumor cells expressing O8E in a subject, comprising administering to the subject an isolated monoclonal antibody or an antigen-binding portion thereof, in an amount effective to treat the disease, wherein the antibody or antigen-binding portion thereof cross-competes for binding to human O8E with a reference antibody or reference antigen-binding portion thereof comprising:
   (a) a heavy chain variable region comprising amino acids having the sequence set forth in SEQ ID NO: 1 and a light chain variable region comprising amino acids having the sequence set forth in SEQ ID NO: 6;
   (b) a heavy chain variable region comprising amino acids having the sequence set forth in SEQ ID NO: 2 and a light chain variable region comprising amino acids having the sequence set forth in SEQ ID NO: 7;
   (c) a heavy chain variable region comprising amino acids having the sequence set forth in SEQ ID NO: 3 and a light chain variable region comprising amino acids having the sequence set forth in SEQ ID NO: 8;
   (d) a heavy chain variable region comprising amino acids having the sequence set forth in SEQ ID NO: 4 and a light chain variable region comprising amino acids having the sequence set forth in SEQ ID NO: 9; or
   (e) a heavy chain variable region comprising amino acids having the sequence set forth in SEQ ID NO: 5 and a light chain variable region comprising amino acids having the sequence set forth in SEQ ID NO: 10;
   wherein the antigen-binding portion of the cross-competing antibody is conjugated to a therapeutic agent.

13. The method of claim 12, wherein the reference antibody or reference antigen-binding portion thereof comprises:
   (a) a heavy chain variable region comprising amino acids having the sequence set forth in SEQ ID NO: 1; and
   (b) a light chain variable region comprising amino acids having the sequence set forth in SEQ ID NO: 6.

14. The method of claim 12, wherein the reference antibody or reference antigen-binding portion thereof comprises:
   (a) a heavy chain variable region comprising amino acids having the sequence set forth in SEQ ID NO: 2; and
   (b) a light chain variable region comprising amino acids having the sequence set forth in SEQ ID NO: 7.

15. The method of claim 12, wherein the reference antibody or reference antigen-binding portion thereof comprises:
   (a) a heavy chain variable region comprising amino acids having the sequence set forth in SEQ ID NO: 3; and
   (b) a light chain variable region comprising amino acids having the sequence set forth in SEQ ID NO: 8.

16. The method of claim 12, wherein the reference antibody or reference antigen binding portion thereof comprises:
   (a) a heavy chain variable region comprising amino acids having the sequence set forth in SEQ ID NO: 4; and
   (b) a light chain variable region comprising amino acids having the sequence set forth in SEQ ID NO: 9.

17. The method of claim 12, wherein the reference antibody or reference antigen binding portion thereof comprises:
   (a) a heavy chain variable region comprising amino acids having the sequence set forth in SEQ ID NO: 5; and
   (b) a light chain variable region comprising amino acids having the sequence set forth in SEQ ID NO: 10.

18. The method of claim 12, wherein the monoclonal antibody or antigen-binding portion thereof is internalized upon binding to its antigen.

19. The method of claim 12, wherein the monoclonal antibody or antigen-binding portion thereof binds to a breast cell carcinoma tumor cell line, the breast cell carcinoma tumor cell line being SKBR3 cell line.

20. The method of claim 12, wherein the monoclonal antibody or antigen-binding portion thereof lacks fucose residues.

21. A method of treating a disease characterized by growth of tumor cells expressing O8E in a subject, comprising administering to the subject an isolated monoclonal antibody or an antigen-binding portion thereof, in an amount effective to treat the disease, wherein the antibody or antigen-binding portion thereof comprises (a) a heavy chain variable region CDR1 comprising amino acids having the sequence set forth in SEQ ID NO: 12; (b) a heavy chain variable region CDR2 comprising amino acids having the sequence set forth in SEQ ID NO: 17; (c) a heavy chain variable region CDR3 comprising amino acids having the sequence set forth in SEQ ID NO: 22; (d) a light chain variable region CDR1 comprising amino acids having the sequence set forth in SEQ ID NO: 27; (e) a light chain variable region CDR2 comprising amino acids having the sequence set forth in SEQ ID NO: 32; and (f) a light chain variable region CDR3 comprising amino acids having the sequence set forth in SEQ ID NO: 37, wherein the antibody or antigen-binding portion thereof specifically binds to human O8E, and wherein the antigen-binding portion thereof is conjugated to a therapeutic agent.

22. A method of treating a disease characterized by growth of tumor cells expressing O8E in a subject, comprising administering to the subject an isolated monoclonal antibody or antigen-binding portion thereof, in an amount effective to treat the disease, wherein the antibody or antigen-binding portion thereof comprises (a) a heavy chain variable region comprising amino acids having the sequence set forth in SEQ ID NO: 2; and (b) a light chain variable region comprising amino acids having the sequence set forth in SEQ ID NO: 7, wherein the antibody or antigen-binding portion thereof specifically binds to human O8E, and wherein the antigen-binding portion thereof is conjugated to a therapeutic agent.

23. The method of any one of claims 1, 12, 21 and 22, wherein the disease is cancer.

24. The method of claim 23, wherein the cancer is selected from the group consisting of breast cell carcinoma, ovarian cancer, kidney cancer, and head and neck cancer.

25. The method of any one of claims 1, 12, 21, and 22, wherein the therapeutic agent is a cytotoxin.

26. The method of any one of claims 1, 12, 21 and 22, wherein the therapeutic agent is a radioactive isotope.

* * * * *